US009314458B2

(12) United States Patent
Aylward et al.

(10) Patent No.: US 9,314,458 B2
(45) Date of Patent: Apr. 19, 2016

(54) TOPICAL USE OF INGENOL-3-ANGELATE OR A SALT THEREOF TO TREAT SKIN CANCER

(75) Inventors: James Harrison Aylward, Indooroopilly (AU); Peter Gordon Parsons, St. Lucia (AU); Andreas Suhrbier, Bunya (AU); Kathleen Anne Turner, Endeavour Hills (AU)

(73) Assignee: LEO Laboratories Limited, Dublin (IE)

( * ) Notice: Subject to any disclaimer, the term of this patent is extended or adjusted under 35 U.S.C. 154(b) by 0 days.

(21) Appl. No.: 13/034,172

(22) Filed: Feb. 24, 2011

(65) Prior Publication Data

US 2011/0213002 A1    Sep. 1, 2011

Related U.S. Application Data

(60) Continuation of application No. 12/543,087, filed on Aug. 18, 2009, now abandoned, which is a division of application No. 10/315,318, filed on Dec. 9, 2002, now Pat. No. 7,838,555, which is a continuation-in-part of application No. PCT/AU01/00680, filed on Jun. 7, 2001.

(30) Foreign Application Priority Data

Jun. 7, 2000    (AU) ..................................... PQ8017

(51) Int. Cl.
| | |
|---|---|
| *A61P 35/00* | (2006.01) |
| *A61P 17/04* | (2006.01) |
| *A61P 31/22* | (2006.01) |
| *A61K 31/455* | (2006.01) |
| *A61K 31/22* | (2006.01) |
| *A61K 36/47* | (2006.01) |

(52) U.S. Cl.
CPC ............... *A61K 31/455* (2013.01); *A61K 31/22* (2013.01); *A61K 36/47* (2013.01)

(58) Field of Classification Search
USPC ........................................................ 514/183
See application file for complete search history.

(56) References Cited

U.S. PATENT DOCUMENTS

| | | | |
|---|---|---|---|
| 3,809,749 | A | 5/1974 | Persinos |
| 4,418,064 | A | 11/1983 | Powell et al. |
| 4,560,774 | A | 12/1985 | Pettit et al. |
| 4,716,179 | A | 12/1987 | Hecker et al. |
| 5,145,842 | A | 9/1992 | Driedger et al. |
| 5,317,009 | A | 5/1994 | Lee-Huang |
| 5,643,948 | A | 7/1997 | Driedger et al. |
| 5,716,968 | A | 2/1998 | Driedger et al. |
| 5,750,568 | A | 5/1998 | Driedger et al. |
| 5,874,464 | A | 2/1999 | Marquez |
| 5,886,017 | A | 3/1999 | Driedger et al. |
| 5,886,019 | A | 3/1999 | Driedger et al. |
| 5,891,870 | A | 4/1999 | Driedger et al. |
| 5,891,906 | A | 4/1999 | Driedger et al. |
| 5,932,613 | A | 8/1999 | Jiang et al. |
| 5,962,498 | A | 10/1999 | Driedger et al. |
| 6,268,395 | B1 | 7/2001 | Hattori |
| 6,432,452 | B1 | 8/2002 | Aylward |
| 6,593,371 | B1 | 7/2003 | Staggs |
| 6,787,161 | B2 | 9/2004 | Aylward |

(Continued)

FOREIGN PATENT DOCUMENTS

| | | |
|---|---|---|
| CN | 1077129 | 10/1993 |
| CN | 1105246 | 7/1995 |

(Continued)

OTHER PUBLICATIONS

Kupchan et al. Antileukemic Principles Isolated from Euphorbiaceae Plants, Science, 191:571-572, 1976.*
Marco et al., Ingenane and lathyrane diterpenes from the latex of Euphorbia canariensis, Phytochemistry, 45(3):563-570, 1997.*
Hohmann, et al. "Jatrophane diterpenoids from Euphorbia peplus", *Phytochemistry* 51: 673-677 (1999).
Hohmann, et al. "Diterpenoids from Euphorbia peplus", *Planta Med.* 66: 291-294 (2000).

(Continued)

*Primary Examiner* — Jeffrey S Lundgren
*Assistant Examiner* — Zenab Olabowale
(74) *Attorney, Agent, or Firm* — Fish & Richardson P.C.

(57) ABSTRACT

The present invention relates generally to chemical agents useful in the treatment and prophylaxis of inflammatory conditions or in the amelioration of symptoms resulting from or facilitated by an inflammatory condition in a mammalian animal including human and primate, non-mammalian animal and avian species. More particularly, the present invention provides a chemical agent of the macrocyclic diterpene family obtaining from a member of the Euphorbiaceae family of plants or botanical or horticultural relatives thereof or derivatives or chemical analogs or chemically synthetic forms of the agents for use in the treatment or prophylaxis of an inflammatory condition or in the amelioration of symptoms resulting from or facilitated by an inflammatory condition in a mammal, animal or avian species. The present invention further contemplates a method for the prophylaxis or treatment of mammalian, animal or avian subjects for inflammatory conditions including chronic or transitory inflammatory conditions or for ameliorating the symptoms of an inflammatory condition by the topical or systemic administration of a macrocyclic diterpene obtainable from a member of the Euphorbiaceae family or botanical or horticultural relatives thereof or a derivative, chemical analog or chemically synthetic form of the agent. The chemical agent of the present invention may be in the form of a purified compound, mixture of compounds, a precursor form of one or more of the compounds capable of chemical transformation into a therapeutically active agent or be in the form of a chemical fraction, sub-fraction or preparation or extract of the plant.

5 Claims, 21 Drawing Sheets

(56) References Cited

U.S. PATENT DOCUMENTS

| | | | |
|---|---|---|---|
| 6,844,013 | B2 | 1/2005 | Aylward |
| 6,923,993 | B2 | 8/2005 | Donato |
| 7,378,455 | B2 | 5/2008 | Lu et al. |
| 7,410,656 | B2 | 8/2008 | Aylward |
| 7,449,492 | B2 | 11/2008 | Aylward |
| 7,838,555 | B2 | 11/2010 | Aylward et al. |
| 2001/0051644 | A1 | 12/2001 | Aylward |
| 2003/0166613 | A1 | 9/2003 | Aylward |
| 2003/0171334 | A1 | 9/2003 | Aylward |
| 2003/0171337 | A1 | 9/2003 | Aylward |
| 2003/0195168 | A1 | 10/2003 | Aylward |
| 2005/0003031 | A1 | 1/2005 | Aylward |
| 2005/0209192 | A1 | 9/2005 | Aylward |
| 2006/0105994 | A1 | 5/2006 | Aylward |
| 2007/0020297 | A1 | 1/2007 | Wheeler |
| 2008/0279885 | A1 | 11/2008 | Mrue |

FOREIGN PATENT DOCUMENTS

| | | | | |
|---|---|---|---|---|
| CN | | 1112011 | 11/1995 | |
| CN | | 1131037 | 9/1996 | |
| DE | | 29 02 506 | 1/1979 | |
| DE | | 4102054 | A1 7/1992 | |
| EP | | 0 330 094 | 8/1989 | |
| EP | | 0 455 271 | 11/1991 | |
| EP | | 0 310 622 | 4/1992 | |
| HU | | 208790 | B 1/1994 | |
| JP | | 8-13571 | 1/1996 | |
| JP | | 8-176002 | 7/1996 | |
| JP | | 1996-176004 | 7/1996 | |
| JP | | 8-245505 | 9/1996 | |
| JP | | 2002-179581 | 6/2002 | |
| JP | | 2003-212781 | 7/2003 | |
| WO | WO 87/07599 | | 12/1987 | |
| WO | WO 97/15575 | | 5/1997 | |
| WO | WO 99/08994 | | * 2/1999 | C07C 69/78 |
| WO | WO 99/08994 | A1 | * 2/1999 | C07C 69/78 |
| WO | WO 01/93885 | | 12/2001 | |
| WO | 0211743 | A2 | 2/2002 | |
| WO | WO 2005/065696 | | 7/2005 | |
| WO | WO 2006/063382 | A | 6/2006 | |
| WO | 2007059584 | A1 | 5/2007 | |
| WO | WO 2007/053912 | A | 5/2007 | |
| WO | WO 2007/068963 | A | 6/2007 | |
| WO | 2008131491 | A2 | 11/2008 | |

OTHER PUBLICATIONS

Uemura D. et al., "New Diterpene, 13-Oxyingenol, Derivative Isolated From *Euphorbia Kansui* Liou", *Tetrahedron Letters* 29:2529-2532 (1974).
Kupchan S.M. et al., "Antileukemic Principles Isolated From Euphorbiaceae Plants", *Science* 191:571-572 (1975).
Kupchan S.M. et al., "Gnidimacrin and Gnidimacrin 20-Palmitate, Novel Macrocyclic Antileukemic Diterpenoid Esters From Gnidia Subcordata", *Communications to the Editor* 5719-5720 (1976).
Evans F.J. et al., The Tigliane, Daphnane and Ingenane Diterpenes, Their Chemistry, Distribution and Biological Activities, A Review, *Lloydia* 41(3):193-233 (1978).
Hecker E., "Structure-Activity Relationships in Diterpene Esters Irritant and Cocarcinogenic to Mouse Skin", *Carcinogenesis* 2:11-48 (1978).
Seip E.H. et al., "Skin Irritant Ingenol Esters From Euphorbia Esula", *Planta Medica* 46:215-218 (1982).
Nishizuka Y., "The Role of Protein Kinase C in Cell Surface Signal Transduction and Tumour Promotion", *Nature* 308:693-698 (1984).
Schmidt R.J., "The Ingenane Polyol Esters", *Naturally Occurring Phorbol Esters, Boca Raton: CRC Press* 245-269 (1986).
Inoue S. et al., "Ingenane Synthetic Studies. Sterocontrolled Introduction of All Oxygenated and Unsaturated Centers in an Ingenol Prototype", *J. Org. Chem.* 52:5497-5498 (1987).
Hamamoto Y. et al., "Comparison of Effects of Protein Kinase C Inhibitors on Phorbol Ester-Induced CD4 Down-Regulation and Augmentation of Human Immunodeficiency Virus Replication in Human T Cell Lines", *Biochemical and Biophysical Research Communications* 164(1):339-344 (1989).
Chowdhury I.H. et al., "The Phorbol Ester TPA Strongly Inhibits HIV-1-Induced Syncytia Formation But Enhances Virus Production: Possible Involvement of Protein Kinase C Pathway", *Virology* 176:126-132 (1990).
Laurence J. et al., "Phorbol Ester-Mediated Induction of HIV-1 From a Chronically Infected Promonocyte Clone: Blockade by Protein Kinase Inhibitors and Relationship to *Tat*-Directed *Trans*-Activation", *Biochemical and Biophysical Research Communications* 166(1):349-357 (1990).
Krauter, et al., "Structure/activity relationships of polyfunctional diterpenes of tigliane type", Eur. J. Biochem., 242, pp. 417-427 (1996).
El-Merzabani, et al., Planta Med. 1979 vol. 36, pp. 150-155.
M. Belkin,et al. "Tumor-Damaging Capacity of Plant Materials. I. Plants Used as Cathartics", *National Cancer Institute*: 13, Apr. 1952, pp. 139-149.
D. Weedon, et al. "Home Treatment of Basil Cell Carcinoma", Med. J. Aust., 1, Jun. 1976, p. 928.
Zayed, et al. J. Cancer Res. Clin. Oncol. 1998. vol. 124, pp. 301-308.
Benjamini, et al. Immunology—A Short Course. 1988, Publ: Allan R. Liss, Inc. NY. pp. 15-18.
Abo, K.A. Fitoterapia, 1988. vol. LIX, No. 3, pp. 244-246.
Alastair Aitken, et al., "The Activation of Protein Kinase C by Daphnane, Ingenane and Tigliane Diterpenoid Esters", *Botanical Journal of the Linnean Society*, vol. 94 pp. 247-263 (1987).
Sahar El-Mekkawy, et al., "Anti-HIV-1 Phorbol Esters from the Seed of *Croton Tiglium"*, *Phytochemistry*, vol. 53 pp. 457-464, (2000).
F.J. Evans et al, "Pro-Inflammatory, Tumor-Promoting and Anti-Tumor Diterpenes of the Plant Families Euphoribiaceae and Thymelaeaceae" Department of Pharmacognosy, The School of Pharmacy, University of London, References, vol. 44, pp. 90-99.
Tian-Shung Wu, et al., "Antitumor Agents, 119[1] Kansuiphorins A and B, Two Novel Antileukemic Diterpene Esters From Euphorbia Kansui", Journal of Natural Products, May-Jun. 1991, vol. 54, No. 3, pp. 823-829.
Salah M.A.D. Zayed, et al., "Dietary cancer risk from conditional cancerogens in produce of livestock fed on species of spruge (Euphorbiaceae) I. Skin irritant and tumor promoters of the ingenane diterpene ester type", Cancer Res. Clin. Ocol, 1998, 124: pp. 131-140.
B D Curti "Physical barriers to drug delivery in tumors", Critical Reviews in Oncology/Hematology, 1993; 14: pp. 29-39.
G B Dermer, Another Anniversary for the War on Cancer, Bio/Technology, Mar. 1994, vol. 12, p. 320.
T. Gura, "Systems for Identifying New Drugs are Often Faulty", Science, Nov. 1997, vol. 278, pp. 1041-1042.
R.I. Freshney "Culture of Animal Cells, A Manual of Basic Technique", Department of Clinical Oncology, Cancer Research Campaign Laboratories, University Glasgow.
L H Hartwell, et al. Integrating Genetic Approaches in the Discovery of Anticancer Drugs, Science, vol. 278, Nov. 7, 1997, pp. 1064-1068.
R K Jain, "Barriers to Drug Delivery in Solid Tumors", Scientific American, Jul. 1994, pp. 58-65.
Extract from Endocrinology, Proceedings of the American Association for Cancer Research, vol. 36, Mar. 1995, p. 256.
Derwent Abstract Accession No. 1992-206104/32, Class B04 C03, DE 4102054 A dated Jul. 30, 1992.
Biswas T.K. et al., "Plant Medicines of Indian Origin for Would Healing Activity: A Review" *Lower Extremity Wounds* 2(1):25-39 (2003).
Natrajan D. et al., "Anti-bacterial activity of *Euphoria fusiformis*—a rare medicinal herb" *Journal of Enthopharmacology* 102: 123-126 (2005).
Betancur-Galvis LA et al., "Cytotoxic and Antiviral Activities of Colombian Medicinal Plant Extracts of the *Euphorbia* genus" *Memorias do Instituto Oswaldo Cruz* 97(4): 541-546 (2002).
Guarrera Paolo Maria, "Traditional pytotherapy in Central Italy" *Fitoterapia* 76(1): 1-25 (2005).

(56) References Cited

OTHER PUBLICATIONS

Tropical Plant Database, Database File for AVELOZ (Euphorbia tirucalli) http://web.archive.org/web/20041030080015/http://www.rain-tree.com/aveloz.htm.
Ogbourne S. et al., "Proceedings of the First International Conference of PEP005", *Anti-Cancer Drugs* 18(3):357-362 (2007).
Kaminsky A. et al., "Eoforbia y Cantaridina en el Tratamiento Topico de las Verrugas" *El Dia Medico* 31:1374-1380 (1959).
Weedon D. et al., "Home treatment of basal cell carcinoma" *The Medical Journal of Australia* 1(24):928 (1976).
Jeeva S. et al., "Weeds of Kanyakumari district and their value in rural life" *Indian Journal of Traditional Knowledge* 5(4):501-509 (2006).
Bhatt V.P. et al., "Ethnomedical plant recourses of *Jaunsari* tribe of Garhwal Himalaya Uttaranchal" *Indian Journal of Traditional Knowledge* 5(3):331-335 (2006).
Jadeja B.A. et al., "Indigenous animal healthcare practices in district Porbandar Gujarat" *Indian Journal of Traditional Knowledge* 5(2):268-270 (2006).
Jain S.K. et al., "Traditional uses of some Indian plants amount islanders of the Indian Ocean" *Indian Journal of Traditional Knowledge* 4(4): 345-357 (2005).
Katewa S.S. et al., "Traditional herbal medicines from Shekhawati region of Rajasthan" *Indian Journal of Traditional Knowledge* 4(3):237-245 (2005).
Hampson P. et al. "PEP005, a selective small-molecule activator of protein kinase C, has potent antileukemic activity mediated via the delta isoform of PKC" *Blood* 106(4):1362-1368 (2005).
Sorg et al., "Structure/activity relationships of polyfunctional diterpenes of the ingenane type. I. Tumor-promoting activity of homologous, aliphatic 3-esters of ingenol and of $\Delta^{7,8}$-isolingenol-3-tetradecanoate", Carcinogenesis, vol. 8, No. 1, pp. 1-4, (1987).
Fujiwara et al., "Upregulation of HIV-1 replication in chronically infected cells by ingenol derivatives", Arch Viro 143: 2003-2010 (1998).
Sayed et al., "Constituents of Egyptian Euphorbiaceae. IX. Irritant and cytotoxic ingenane esters from *Euphorbia paralias* L.", Experientia 36, pp. 1206-1207 (1980).
Adolf et al., 3-O-Angeloylingenol, The Toxic and Skin Irritant Factor from Latex of *Euphorbia Anitiquorum* L. (Euphorbiaceae) and from a Derived Thai Purgative and Anthelminthic (Vermifuge) Drug, J. Sci. Soc. Thailand, 9, 81-88 (1983).
Wiriyachitra, et al., Investigations of Medicinal Plants of Euphorbiaceae and Thymelaeaceae Occurring and Used in Thailand; II. Cryptic Irritants of the Diterpene Ester Type from Three *Excoecaria* species, Planta Med, 51:5, 368-71 (1985).
Marco et al., Ingenane and Lathyrane Diterpenes from the Latex of *Euphorbia canariensis*, Phytochemistry, vol. 45, No. 3, 563-570 (1997).
Zayed et al., Dietary cancer risk conditional cancerogens in produce of livestock fed on species of spurge (*Euphorbiaceae*), J. Cancer Res. Clin Oncol, 124, 131-140 (1998).
Berkow, R., Editor-in-Chief, The Merck Manual of Diagnosis and Therapy, 14th Edition, 200-203 (1982).
Berkow, R., Editor-in-Chief, The Merck Manual of Diagnosis and Therapy, 14th Edition, 2046-2049 (1982).
Byers, T. "What Can Randomized Controlled Trials Tell Us About Nutrition and Cancer Prevention", A Cancer Journal for Clinicians, 49(6):353-361 (1999).
Challacombe, J.M. et al. "Neutrophils are a Key Component of the Antitumor Efficacy of Topical Chemotherapy with Ingenol-3-Angelate", The Journal of Immunology, 177(11): 8123-8132 (2006).
Cheever, M.A. et al. "Potential Uses of Interleukin-2 in Cancer Therapy", Immunobiology, 172(3-5): 365-382 (1986).
De Clercq, E. "In Search of a Selective Antiviral Chemotherapy", Clinical Microbiology Reviews, 10(4): 674-693 (1997).
Ghorbani, A. Studies on Pharmaceutical Ethnobotany in the Region of Turkmen Sahra, North of Iran (Part 1): General Results, Journal of Ethnopharmacology, 102(1): 58-68 (2005).
Gillespie, S.K. et al. "Ingenol 3-Angelate Induces Dual Modes of Cell Death and Differentially Regulates Tumor Necrosis Factor—Related Apoptosis Inducing Ligand-Induced Apoptosis in Melanoma Cells", Molecular Cancer Therapeutics 3(12):1651-1658 (2004).
Granziero, L. et al. "Adoptive Immunotherapy Therapy Prevents Prostate Cancer in a Transgenic Animal Model", Eur. J. Immunol. 29: 1127-1138 (1999).
Hampson, P. et al. "PEP-005", Drugs of the Future 30(10):1003-1005 (2005).
Jakupovic, J. et al. "Diterpenes From Euphorbia Peplus", Phytochemistry 47(8):1601-1609 (1998).
Le, T.T.T. et al. "Immunostimulatory Cancer Chemotherapy Using Local Ingenol-3-Angelate and Synergy with Immunotherapies", Vaccine 27(23): 3053-3062 (2009).
Mandell, G.L. et al. Douglas and Bennett's Principles and Practice of Infectious Diseases, 4th Edition, 1314-1323,1330-1335, and 1590-1603 (1995).
Mutschler, E. et al. Drug Actions—Basic Principles and Therapeutic Aspects, 515-580 (1995).
Nickel, A. et al. "Total Synthesis of Ingenol", Journal of the American Chemical Society 126: 16300-16301 (2004).
Ogbourne, S.M. et al. "Antitimor Activity of 3-Ingenol Angelate: Plasma Membrane and Mitochondrial Disruption and Necrotic Cell Death", Cancer Research 64: 2833-2839 (2004).
Rasik, A.M. et al. "Wound Healing Activity of Latex of Euphorbia Neriifolia Linn", Indian Journal of Pharmacology 28 (2):107-109 (1996).
Samuelsson, G. et al. "Inventory of Plants Used in Traditional Medicine in Somalia. II. Plants of the Families Combretaceae to Labiatae", Journal of Ethnopharmacology 37: 47-70 (1992).
Shimizu, K. et al. "Potentiation of Immunologic Responsiveness to Dendritic Cell-Based Tumor Vaccines by Recombinant Interleukin-2", Cancer Journal 6(1):S67-S75 (2000).
Sillier, G. et al. "PEP005 (Ingenol Mebutate) Gel, a Novel Agent for the Treatment of Actinic Keratosis: Results of a Randomized, Double-Blind, Vehicle-Controlled, Multicentre, Phase IIa Study", Australasian Journal of Dermatology 50: 16-22 (2001).
Timmerman, J.M. and Levy, R. "Dendritic Cell Vaccines for Cancer Immunotherapy", Annual Review of Medicine 50: 507-529 (1999).
Third Party Observation dated Mar. 2, 2011 issued in Canadian Application No. CA 2411726.
Third Party Observation dated May 25, 2011 issued in European Application No. EP 01937873.6.
Third Party Observation dated May 23, 2011 issued in European Application No. EP 01940015.9.
Third Party Observation dated Jul. 11, 2011 issued in Canadian Application No. CA 2411596.
Valente, C. et al. "Three New Jatrophane-Type Diterpenes from Euphorbia Pubescens", Planta Medicine 69: 361-366 (2003).
European Search Report, dated Mar. 8, 2013, in corresponding European Patent Application No. 01 937 873.6.
Third Party Observation under Article 115 of the EPC in corresponding European Patent Application No. 01 937 873.6, dated May 10, 2011.
"Danti Dravanti Guna", Traditional Knowledge Digital Library, Jan. 1, 1979 (Exhibit 1).
"Kuppi", Traditional Knowledge Digital Library, Jan. 1, 1899 (Exhibit 2).
"Harpa-rewadi", Traditional Knowledge Digital Library, Jan. 1, 1926 (Exhibit 3).
"Sankara Kiranikku Kudineer", Traditional Knowledge Digital Library, undated (Exhibit 4).
"Tadbeer-e-Hab-ul-Mulook", Traditional Knowledge Digital Library, Jan. 1, 1930 (Exhibit 5).
"Patoladi Curna", Traditional Knowledge Digital Library, Jan. 1, 2003 (Exhibit 6).
"Vathakaduppukku Vethu", Traditional Knowledge Digital Library, Jan. 1, 1879 (Exhibit 7).
"Thalaka Mezhugu-3", Traditional Knowledge Digital Library, Jan. 1, 1975 (Exhibit 8).

(56) References Cited

OTHER PUBLICATIONS

"Velli Mezhugu", Traditional Knowledge Digital Library, Jan. 1, 1975 (Exhibit 9).
"Paranghi Choornam", Traditional Knowledge Digital Library, Jan. 1, 1956 (Exhibit 10).
"Vathathirku Ennai", undated, Traditional Knowledge Digital Library (Exhibit 11).
"Linga Chenduram-20", Traditional Knowledge Digital Library, Jan. 1, 1975 (Exhibit 12).
"Dravanti Guna", Traditional Knowledge Digital Library, Jan. 1, 1998 (Exhibit 13).

* cited by examiner

Normal Skin (24 hour)

Vehicle Only

PEP010

B16 SC (24 hour)

Vehicle Only

PEP010

Normal Skin (48 hour)

Vehicle Only        PEP010

B16 SC (48 hour)

Vehicle Only        PEP010

TOPICAL USE OF INGENOL-3-ANGELATE OR A SALT THEREOF TO TREAT SKIN CANCER

CROSS REFERENCE TO RELATED APPLICATIONS

This is a continuation of copending U.S. patent application Ser. No. 12/543,087 filed Aug. 18, 2009 which is a divisional of copending U.S. patent application Ser. No. 10/315,318 filed Dec. 9, 2002 which is a continuation in part of copending PCT application PCT/AU01/00680, filed on Jun. 7, 2001.

FIELD OF THE INVENTION

The present invention relates generally to chemical agents useful in the treatment and prophylaxis of inflammatory conditions or in the amelioration of symptoms resulting from or facilitated by an inflammatory condition in a mammalian animal including human and primate, non-mammalian animal and avian species. More particularly, the present invention provides a chemical agent of the macrocyclic diterpene family obtaining from a member of the Euphorbiaceae family of plants or botanical or horticultural relatives thereof or derivatives or chemical analogues or chemically synthetic forms of the agents for use in the treatment or prophylaxis of an inflammatory condition or in the amelioration of symptoms resulting from or facilitated by an inflammatory condition in a mammal, animal or avian species. The present invention further contemplates a method for the prophylaxis or treatment of mammalian, animal or avian subjects for inflammatory conditions including chronic or transitory inflammatory conditions or for ameliorating the symptoms of an inflammatory condition by the topical or systemic administration of a macrocyclic diterpene obtainable from a member of the Euphorbiaceae family or botanical or horticultural relatives thereof or a derivative, chemical analogue or chemically synthetic form of the agent. The chemical agent of the present invention may be in the form of a purified compound, mixture of compounds, a precursor form of one or more of the compounds capable of chemical transformation into a therapeutically active agent or be in the form of a chemical fraction, sub-fraction or preparation or extract of the plant.

BACKGROUND OF THE INVENTION

Bibliographic details of the publications referred to by author in this specification are collected at the end of the description.

Reference to any prior art in this specification is not, and should not be taken as, an acknowledgment or any form of suggestion that this prior art forms part of the common general knowledge in Australia or any other country.

Natural product screening is a term applied to the screening of natural environments for bioactive molecules. Particularly sought after bioactive molecules are those having potential as useful therapeutic agents. Natural environments include plants, microorganisms, coral and marine animals. The search for potential therapeutic agents for the treatment of cancer and infection by pathogenic organisms remains an important focus.

The Euphorbiaceae family of plants covers a wide variety of plants including weeds and other types of plants of *Euphorbia* species. There have been a variety of inconclusive reports on the potential effects of the sap of these plants on a range of conditions as well as promoting tumorigenesis and causing skin and ocular irritation.

The most intensively studied species of this group is *Euphorbia pilulifera* L (synonyms *E. hirta* L., *E. capitata* Lam.), whose common names include pill-bearing spurge, snakeweed, cat's hair, Queensland asthma weed and flowery-headed spurge. The plant is widely distributed in tropical countries, including India, and in Northern Australia, including Queensland.

A recent report describes selective cytotoxicity of a number of tiglilane diterpene esters from the latex of *Euphorbia poisonii*, a highly toxic plant found in Northern Nigeria, which is used as a garden pesticide. One of these compounds has a selective cytotoxicity for the human kidney carcinoma cell line A-498 more than 10,000 times greater than that of adriamycin (Fatope et al., 1996).

*Euphorbia hirta* plants and extracts thereof have been considered for a variety of purposes, including tumor therapy (EP 0 330 094), AIDS-related complex and AIDS (HU-208790) and increasing immunity and as an anti-fungoid agent for treatment of open wounds (DE-4102054).

Thus, while there are isolated reports of anti-cancer activity of various *Euphorbia* preparations (see Fatope et al., 1996; Oksuz et al., 1996), not only are the compounds present in at least one *Euphorbia* species reported to be carcinogenic (Evans and Osman, 1974; Stavric and Stolz, 1976; Hecker, 1970), but at least one species has a skin-irritant and tumor-promoting effect (Gundidz et al., 1993) and another species reduces EBV-specific cellular immunity in Burkitt's lymphoma (Imai, 1994).

In accordance with the present invention, the inventors have identified chemical agents and fractions comprising these agents which are useful in the treatment and prophylaxis of inflammatory conditions in mammalian, animal and avian subjects.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The present invention is predicated in part on the identification of chemical agents and fractions comprising same from plants of the Euphorbiaceae family which are useful in the treatment and prophylaxis of inflammatory conditions and potentially inflammatory conditions. Such conditions include autoimmune conditions, conditions associated with infection by pathogenic conditions, conditions associated with an inflammatory immune response or proliferation of cells of the immune system and conditions requiring immunopotentiation. The inventors have further identified that the chemical agents of the present invention are capable of modulating protein kinase C (PKC) activity thus providing a basis for the treatment of conditions where PKC activity is required to be up-regulated or down-regulated.

Accordingly, one aspect of the present invention contemplates a method for the treatment or prophylaxis of an inflammatory condition in an subject, said method comprising the administration to said subject of a symptom-ameliorating effective amount of a chemical agent obtainable from a plant of the Euphorbiaceae family or a derivative or chemical analogue thereof which chemical agent is a macrocyclic diterpene selected from compounds of the ingenane, pepluane and jatrophane families and which chemical agent or derivative or chemical analogue is represented by any one of the general formulae (I)-(V) as defined herein and which chemical agent or derivative or chemical analogue thereof is capable of modulating PKC activity, PKC-dependent gene expression or PKC enzyme turnover and wherein said chemical agent or its derivatives or chemical analogues is administered for a time and under conditions sufficient to ameliorate one or more symptoms associated with said inflammatory condition.

Another aspect of the present invention contemplates a method for the immunopotentiation of a subject in the treatment and prophylaxis of said subject for infection by a pathogenic organism or a potential pathogenic organism, said method comprising the administration to said subject of a symptom-ameliorating effective amount of a macrocyclic diterpene, or a chemical fraction comprising same from a plant of the family Euphorbiaceae or a derivative or chemical analogue of said macrocyclic diterpene having the structures as defined above wherein said macrocyclic diterpene or its derivative or chemical analogue modulates PKC activity, synthesis or enzyme turnover, said administration being for a time and under conditions sufficient to potentiate components of the immune system.

Yet another aspect of the present invention provides a method for the treatment or prophylaxis of an inflammatory condition in a subject, said method comprising the administration to said subject of a symptom-ameliorating effective amount of a macrocyclic diterpene or chemical fraction comprising same from a plant of the family Euphorbiaceae or a derivative or chemical analogue of said macrocyclic diterpene having the structures as defined above wherein said macrocyclic diterpene or its derivative or chemical analogue modulates PKC activity, synthesis or enzyme turnover, said administration being for a time and under conditions sufficient to treat said inflammatory condition.

Still another aspect of the present invention contemplates a method of assessing the suitability of a chemical agent from Euphorbiaceae for the practice of the present invention. Numerical values are assigned to chemical agents including fractions comprising the chemical agents as set forth, for example, in Table A:—

TABLE A

| Feature | Value |
|---|---|
| An ability to modulate PKC activity or effect | +1 |
| An ability to induce bipolar dendritic activity | +1 |
| An ability to displace phorbol dibutyrate from binding to PKC | +1 |
| An ability to induce respiratory burst in leucocytes | +1 |
| An ability to stimulate phagocytosis in peripheral blood mononuclear cells | +1 |
| Derived from a member of the Euphorbiacea family | +1 |
| Derived from *E. peplus* | +3 |
| Water extractible from the sap of *Euphorbia* sp. | +2 |
| An ability to activate latent virus | +4 |
| A lower tumor promotion activity than TPA/PMA | +2 |

Still even another aspect of the present invention contemplates a method for the treatment or prophylaxis of an inflammatory condition in a subject, said method comprising administration to said subject of a symptom-ameliorating effective amount of a macrocyclic diterpene obtainable from a Euphorbiaceae plant or its botanical or horticultural relative, said macrocyclic diterpene being selected from an ingenane, pepluane or jatrophane, or a derivative or chemical analogue thereof, having the structure represented by any one of the general formulae (I)-(V) as defined below and wherein said chemical agent exhibits a potency of agent $(P_A)$ of >10, wherein the $P_A = \Sigma I_V$ where $I_V$ is a numerical value associated with a particular feature as defined in Table A or pharmaceutically acceptable salts of these, said chemical agent being administered for a time and under conditions sufficient to ameliorate at least one symptom caused by or associated with inflammation.

Even yet another aspect the invention contemplates a method for immunopotentiating a subject, said method comprising administration to said subject of a potentiating effective amount of a macrocyclic diterpene obtainable from a Euphorbiaceae plant or its botanical or horticultural relative, said macrocyclic diterpene being selected from an ingenane, pepluane or jatrophane, or a derivative or chemical analogue thereof, having the structure represented by any one of the general formulae (I)-(V) as defined below and wherein said chemical agent exhibits a potency of agent $(P_A)$ of >10, wherein the $P_A = \Sigma I_V$ where $I_V$ is a numerical value associated with a particular feature as defined above or pharmaceutically acceptable salts of these, said chemical agent being administered for a time and under conditions sufficient to immunopotentiate said subject.

A further aspect of the present invention contemplates a computer program product for assessing the likely usefulness of a candidate compound or group of compounds for the treatment or prophylaxis of inflammation or to immunopotentiate a subject, said product comprising:—
(1) code that receives as input index values for at least two features associated with said compound(s), wherein said features are selected from:
   (a) the ability to modulate PKC activity or effect;
   (b) the ability to induce bipolar dendritic activity;
   (c) the ability to be derived from a member of the Euphorbiaceae family;
   (d) the ability to be derived from *E. peplus;*
   (e) the ability to be water extractable from the sap of a *Euphorbia* species; or
   (f) the ability to activate latent virus;
   (g) less tumor promoting capacity than TPA or MPA;
(2) code that adds said index values to provide a sum corresponding to a potency value for said compound(s); and
(3) a computer readable medium that stores the codes.

Another aspect of the present invention extends to a computer for assessing the likely usefulness of a candidate compound or group of compounds for the treatment of inflammation or to immunopotentiate a subject, wherein said computer comprises:—
(1) a machine-readable data storage medium comprising a data storage material encoded with machine-readable data, wherein said machine-readable data comprise index values for at least two features associated with said compound(s), wherein said features are selected from:
   (a) the ability to modulate PKC activity or effect;
   (b) the ability to induce bipolar dendritic activity;
   (c) the ability to be derived from a member of the Euphorbiaceae family;
   (d) the ability to be derived from *E. peplus;*
   (e) the ability to be water extractable from the sap of a *Euphorbia* species; or
   (f) the ability to activate latent virus;
   (g) less tumor promoting capacity than TPA or PMA.
(2) a working memory for storing instructions for processing said machine-readable data;
(3) a central-processing unit coupled to said working memory and to said machine-readable data storage medium, for processing said machine readable data to provide a sum of said index values corresponding to a potency value for said compound(s); and (4) an output hardware coupled to said central processing unit, for receiving said potency value.

BRIEF DESCRIPTION OF THE FIGURES

FIG. 18 is a graphical representation showing survival of Jam cells after treatment with saps from various Euphorbiaceae, expressed as percentage cell survival determined by sulfurhodamine B staining of cells. FIG. 18A shows the cytotoxicity of the saps alone on the Jam cells, while

Figure 1:
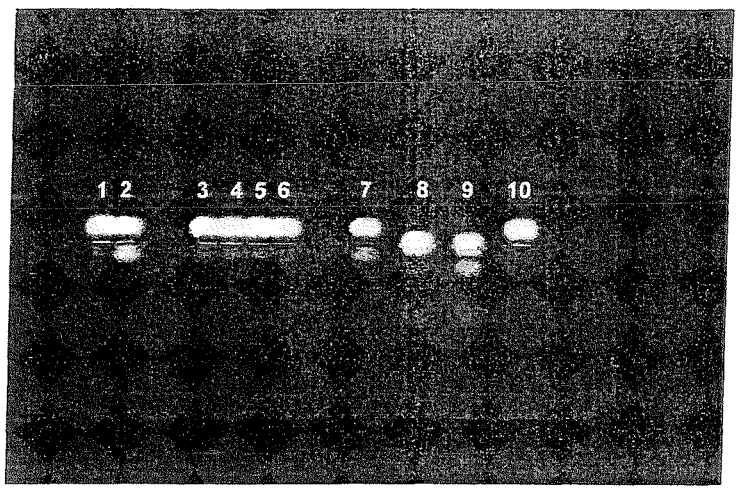
FIG. 1 shows the activation of PKC, using a fluorescent peptide assay ("PepTag" non-radioactive protein kinase kit, Promega). Lane 1, PKC and substrate alone; lane 2, plus positive control activator; lane 3, plus 100 ng/ml TPA; lane 4, plus 0.1 ng/ml TPA; lane 5, plus 0.01 ng/ml TPA; lane 6, plus 0.001 ng/ml TPA; lane 7, ether extract of *E. peplus* sap in DEM, diluted 1 in 5; lane 8, aqueous layer from ether extraction, diluted 1/25; lane 9, crude sap diluted 1/25; lane 10, DME alone.

Compounds may be referred to in the subject specification by a compound code. These are defined as below:—

| TABLE OF COMPOUND CODES | |
|---|---|
| COMPOUND CODE | DESCRIPTION |
| PEP001 | Crude sap |
| PEP002 | Methanol and ether extract of *E. peplus* sap prepared according to Example 7 of PCT/AU98/00656 |
| PEP003 | Ingenane enriched fraction prepared according to Examples 21 and 23 |
| PEP004 | Jatrophane/Pepluane enriched fraction prepared according to Example 7 of PCT/AU98/00656 |
| PEP005 | ingenol-3-angelate |
| PEP006 | 20-deoxy-ingenol-3-angelate |
| PEP008 | 20-O-acetyl-ingenol-3-angelate |
| PEP009 | Acetone Extract of XAD prepared according to Example 21 |
| PEP010 | Ingenane enriched fraction prepared according to Examples 22 and 23 |

DETAILED DESCRIPTION OF THE PREFERRED EMBODIMENTS

The present invention is predicated in part on the identification of biologically useful properties of chemical agents and chemical fractions comprising these agents obtainable from a member of the Euphorbiaceae family of plants or their botanical or horticultural relatives. These biologically useful properties include their use in the prophylaxis and/or treatment of inflammatory conditions including facilitating potentiation of the immune system or of cells or other compounds of the immune system as well as the amelioration of symptoms associated with inflammation.

The term "treatment" is used in its broadest sense and includes the prevention of a disease condition as well as facilitating the amelioration of the effects of symptoms of inflammation in addition to or alternatively stimulating components of the immune system.

The term "prophylaxis" is also used herein in its broadest sense to encompass a reduction in the risk of development of inflammation. In certain conditions, an agent may act to treat a subject prophylactically. Furthermore, the prophylactic administration of an agent may result in the agent becoming involved in the treatment of a pathological condition. Use of the terms "treatment" or "prophylaxis" is not to be taken as limiting the intended result which is to reduce the adverse effects of inflammation or to potentiate the immune system or components therein and/or to ameliorate the symptoms or risk of development of symptoms caused or facilitated by inflammation.

The present invention is particularly directed to the use of one or more macrocyclic diterpenes from a member of the Euphorbiaceae family of plants or botanical or horticultural relatives of such plants. Reference herein to a member of the Euphorbiaceae family includes reference to species from the genera *Acalypha, Acidoton, Actinostemon, Adelia, Adenocline, Adenocrepis, Adenophaedra, Adisca, Agrostistachys, Alchornea, Alchorneopsis, Alcinaeanthus, Alcoceria, Aleurites, Amanoa, Andrachne, Angostyles, Anisophyllum, Antidesma, Aphora, Aporosa, Aporosella, Argythamnia, Astrococcus, Astrogyne, Baccanrea, Baliospermum, Bernardia, Beyeriopsis, Bischofia, Blachia, Blumeodondron, Bonania, Bradleia, Breynia, Breyniopsis, Briedelia, Buraeavia, Caperonia, Caryodendron, Celianella, Cephalocroton, Chaenotheca, Chaetocarpus, Chamaesyce, Cheilosa, Chiropetalum, Choriophyllum, Cicca, Chaoxylon, Cleidon, Cleistanthus, Cluytia, Cnesmone, Cnidoscolus, Coccoceras, Codiaeum, Coelodiscus, Conami, Conceveiba, Conceveibastrum, Conceveibum, Corythea, Croizatia, Croton, Crotonopsis, Crozophora, Cubanthus, Cunuria, Dactylostemon, Dalechampia, Dendrocousinsia, Diaspersus, Didymocistus, Dimorphocalyx, Discocarpus, Ditaxis, Dodecastingma, Drypetes, Dysopsis, Elateriospermum, Endadenium, Endospermum, Erismanthus, Erythrocarpus, Erythrochilus, Eumecanthus, Euphorbia, Euphorbiodendron, Excoecaria, Flueggea, Calearia, Garcia, Gavarretia, Gelonium, Giara, Givotia, Glochidion, Clochidionopsis, Glycyclendron, Gymnanthes, Gymnosparia, Haematospermum, Hendecandra, Hevea, Hieronima, Hieronyma, Hippocrepandra, Homalanthus, Hymenocardia, Janipha, Jatropha, Julocroton, Lasiocroton, Leiocarpus, Leonardia, Lepidanthus, Leucocroton, Mabea, Macaranga, Mallotus, Manihot, Mappa, Maprounea, Melanthesa, Mercurialis, Mettenia, Micrandra, Microdesmis, Microelus, Microstachy, Maocroton, Monadenium, Mozinna, Neoscortechinia, Omalanthus, Omphalea, Ophellantha, Orbicularia, Ostodes, Oxydectes, Palenga, Pantadenia, Paradrypeptes, Pausandra, Pedilanthus, Pera, Peridium, Petalostigma, Phyllanthus, Picrodendro, Pierardia, Pilinophytum, Pimeleodendron, Piranhea, Platygyna, Plukenetia, Podocalyx, Poinsettia, Poraresia, Prosartema, Pseudanthus, Pycnocoma, Quadrasia, Reverchonia, Richeria, Richeriella, Ricinella, Ricinocarpus, Rottlera, Sagotia, Sanwithia, Sapium, Savia, Sclerocroton, Sebastiana, Securinega, Senefeldera, Senefilderopsis, Serophyton, siphonia, Spathiostemon, Spixia, Stillingia, Strophioblachia, Synadenium, Tetracoccus, Tetraplandra, Tetrorchidium, Thyrsanthera, Tithymalus, Trageia, Trewia, Trigonostemon, Tyria* and *Xylophylla.*

The most preferred genus and most suitable for the practice of the present invention is the genus *Euphorbia*. Particularly useful species of this genus include *Euphorbia aaron-rossii, Euphorbia abbreviata, Euphorbia acuta, Euphorbia alatocaulis, Euphorbia albicaulis, Euphorbia algomarginata, Euphorbia aliceae, Euphorbia alta, Euphorbia anacampseros, Euphorbia andromedae, Euphorbia angusta, Euphorbia anthonyi, Euphorbia antiguensis, Euphorbia apocynifolia, Euphorbia arabica, Euphorbia ariensis, Euphorbia arizonica, Euphorbia arkansana, Euphorbia arteagae, Euphorbia arundelana, Euphorbia astroites, Euphorbia atrococca, Euphorbia baselicis, Euphorbia batabanensis, Euphorbia bergeri, Euphorbia bermudiana, Euphorbia bicolor, Euphorbia biformis, Euphorbia bifurcata, Euphorbia bilobata, Euphorbia biramensis, Euphorbia biuncialis, Euphorbia blepharostipula, Euphorbia blodgetti, Euphorbia boerhaavioides, Euphorbia boliviana, Euphorbia bracei, Euphorbia brachiata, Euphorbia brachycera, Euphorbia brandegee, Euphorbia brittonii, Euphorbia caesia, Euphorbia calcicola, Euphorbia campestris, Euphorbia candelabrum, Euphorbia capitellata, Euphorbia carmenensis, Euphorbia carunculata, Euphorbia cayensis, Euphorbia celastroides, Euphorbia chalicophila, Euphorbia chamaerrhodos, Euphorbia chamaesula, Euphorbia chiapensis, Euphorbia chiogenoides, Euphorbia cinerascens, Euphorbia clarionensis, Euphorbia colimae, Euphorbia colorata, Euphorbia commutata, Euphorbia consoquitlae, Euphorbia convolvuloides, Euphorbia corallifera, Euphorbia creberrima, Euphorbia crenulata, Euphorbia cubensis, Euphorbia cuspidata, Euphorbia cymbiformis, Euphorbia darlingtonii, Euphorbia defoliata, Euphorbia degeneri, Euphorbia deltoidea, Euphorbia dentata, Euphorbia depressa Euphorbia dictyosperma, Euphorbia dictyosperma, Euphorbia dioeca, Euphorbia discoidalis, Euphorbia dorsiventralis, Euphorbia drumondii, Euphorbia duclouxii, Euphorbia dussii, Euphorbia eanophylla, Euphorbia eggersii, Euphorbia eglandulosa, Euphorbia elata, Euphorbia enalla, Euphorbia eriogonoides, Euphorbia eriophylla, Euphorbia esculaeformis, Euphorbia espirituensis, Euphorbia esula, Euphorbia excisa, Euphorbia exclusa, Euphorbia exstipitata, Euphorbia exstipulata, Euphorbia fendleri, Euphorbia filicaulis, Euphorbia filiformis, Euphorbia florida, Euphorbia fruticulosa, Euphorbia garber, Euphorbia gaumerii, Euphorbia gerardiana, Euphorbia geyeri, Euphorbia glyptosperma, Euphorbia gorgonis, Euphorbia gracilior, Euphorbia gracillima, Euphorbia gradyi, Euphorbia graminea, Euphorbia graminiea Euphorbia grisea, Euphorbia guadalajarana, Euphorbia guanarensis, Euphorbia gymnadenia, Euphorbia haematantha, Euphorbia hedyotoides, Euphorbia heldrichii, Euphorbia helenae, Euphorbia helleri, Euphorbia helwigii, Euphorbia henricksonii, Euphorbia heterophylla, Euphorbia hexagona, Euphorbia hexagonoides, Euphorbia hinkleyorum, Euphorbia hintonii, Euphorbia hirtula, Euphorbia hirta, Euphorbia hooveri, Euphorbia humistrata, Euphorbia hypericifolia, Euphorbia inundata, Euphorbia involuta, Euphorbia jaliscensis, Euphorbia jejuna, Euphorbia johnston, Euphorbia juttae, Euphorbia knuthii, Euphorbia lasiocarpa, Euphorbia lata, Euphorbia latazi, Euphorbia latericolor, Euphorbia laxiflora Euphorbia lecheoides, Euphorbia ledienii, Euphorbia leucophylla, Euphorbia lineata, Euphorbia linguiformis, Euphorbia longecornuta, Euphorbia longepetiolata, Euphorbia longeramosa, Euphorbia longinsulicola, Euphorbia longipila, Euphorbia lupulina, Euphorbia lurida, Euphorbia lycioides, Euphorbia macropodoides, macvaughiana, Euphorbia manca, Euphorbia mandoniana, Euphorbia mangleti, Euphorbia mango, Euphorbia marylandica, Euphorbia mayana, Euphorbia melanadenia, Euphorbia melanocarpa, Euphorbia meridensis, Euphorbia mertonii, Euphorbia mexiae, Euphorbia* microcephala, Euphorbia microclada, Euphorbia micromera, Euphorbia misella, Euphorbia missurica, Euphorbia montana, Euphorbia montereyana, Euphorbia multicaulis, Euphorbia multiformis, Euphorbia multinodis, Euphorbia multiseta, Euphorbia muscicola, Euphorbia neomexicana, Euphorbia nephradenia, Euphorbia niqueroana, Euphorbia oaxacana, Euphorbia occidentalis, Euphorbia odontodenia, Euphorbia olivacea, Euphorbia olowaluana, Euphorbia opthalmica, Euphorbia ovata, Euphorbia pachypoda, Euphorbia pachyrhiza, Euphorbia padifolia, Euphorbia palmeri, Euphorbia paludicola, Euphorbia parciflora, Euphorbia parishii, Euphorbia parryi, Euphorbia paxiana, Euphorbia pediculifera, Euphorbia peplidion, Euphorbia peploides, Euphorbia peplus, Euphorbia pergamena, Euphorbia perlignea, Euphorbia petaloidea, Euphorbia petaloidea, Euphorbia petrina, Euphorbia picachensis, Euphorbia pilosula, Euphorbia pilulifera, Euphorbia pinariona, Euphorbia pinetorum, Euphorbia pionosperma, Euphorbia platysperma, Euphorbia plicata, Euphorbia poeppigii, Euphorbia poliosperma, Euphorbia polycarpa, Euphorbia polycnemoides, Euphorbia polyphylla, Euphorbia portoricensis, Euphorbia portulacoides Euphorbia portulana, Euphorbia preslii, Euphorbia prostrata, Euphorbia pteroneura, Euphorbia pycnanthema, Euphorbia ramosa, Euphorbia rapulum, Euphorbia remyi, Euphorbia retroscabra, Euphorbia revoluta, Euphorbia rivularis, Euphorbia robusta, Euphorbia romosa, Euphorbia rubida, Euphorbia rubrosperma, Euphorbia rupicola, Euphorbia sanmartensis, Euphorbia saxatilis M. Bieb, Euphorbia schizoloba, Euphorbia sclerocyathium, Euphorbia scopulorum, Euphorbia senilis, Euphorbia serpyllifolia, Euphorbia serrula, Euphorbia setiloba Engelm, Euphorbia sonorae, Euphorbia soobyi, Euphorbia sparsiflora, Euphorbia sphaerosperma, Euphorbia syphilitica, Euphorbia spruceana, Euphorbia subcoerulea, Euphorbia stellata, Euphorbia submammilaris, Euphorbia subpeltata, Euphorbia subpubens, Euphorbia subreniforme, Euphorbia subtrifoliata, Euphorbia succedanea, Euphorbia tamaulipasana, Euphorbia telephioides, Euphorbia tenuissima, Euphorbia tetrapora, Euphorbia tirucalli, Euphorbia tomentella, Euphorbia tomentosa, Euphorbia torralbasii, Euphorbia tovariensis, Euphorbia trachysperma, Euphorbia tricolor, Euphorbia troyana, Euphorbia tuerckheimii, Euphorbia turczaminowii, Euphorbia umbellulata, Euphorbia undulata, Euphorbia vermiformis, Euphorbia versicolor, Euphorbia villifera, Euphorbia violacea, Euphorbia whitei, Euphorbia xanti Engelm, Euphorbia xylopoda Greenm, Euphorbia yayalesia Urb., Euphorbia yungasensis, Euphorbia zerayschanica and Euphorbia zinniiflora.

Particularly preferred species of the genus *Synadenium* include *Synadenium grantii* and *Synadenium compactum*.

Particularly preferred species of the genus *Monadenium* include *Monadenium lugardae* and *Monadenium guentheri*.

A preferred species of the genus *Endadenium* is *Endadenium gossweileni*.

*Euphorbia peplus* is particularly useful in the practice of the present invention. Reference herein to "*Euphorbia peplus*" or its abbreviation "*E. peplus*" includes various varieties, strains, lines, hybrids or derivatives of this plant as well as its botanical or horticultural relatives. Furthermore, the present invention may be practiced using a whole Euphorbiaceae plant or parts thereof including sap or seeds or other reproductive material may be used. Generally, for seeds or reproductive material to be used, a plant or plantlet is first required to be propagated.

Reference herein to a Euphorbiaceae plant, a *Euphorbia* species or *E. peplus* further encompasses genetically modified plants. Genetically modified plants include trangenic plants or plants in which a trait has been removed or where an endogenous gene sequence has been down-regulated, mutated or otherwise altered including the alteration or introduction of genetic material which exhibits a regulatory effect on a particular gene. Consequently, a plant which exhibits a character not naturally present in a Euphorbiaceae plant or a species of *Euphorbia* or in *E. peplus* is nevertheless encompassed by the present invention and is included within the scope of the above-mentioned terms.

The macrocyclic diterpenes are generally in extracts of the Euphorbiaceae plants. An extract may comprise, therefore, sap or liquid or semi-liquid material exuded from, or present in, leaves, stem, flowers, seeds, bark or between the bark and the stem. Most preferably, the extract is from sap. Furthermore, the extract may comprise liquid or semi-liquid material located in fractions extracted from sap, leaves, stems, flowers, bark or other plant material of the Euphoriaceae plant. For example, plant material may be subject to physical manipulation to disrupt plant fibres and extracellular matrix material and inter- and intra-tissue extracted into a solvent including an aqueous environment. All such sources of the macrocyclic diterpenes are encompassed by the present invention including macrocyclic diterpenes obtained by synthetic routes.

The preferred macrocyclic diterpenes are selected from compounds of the ingenane, pepluane and jatrophane families. A compound is stated to be a member of the ingenane, pepulane or jatrophane families on the basis of chemical structure and/or chemical or physical properties. A compound which is a derivative of an ingenane, pepluane or jatrophane is nevertheless encompassed by the present invention through use of the terms "ingenane", "pepluane" or "jatrophane" since these terms include derivatives, chemical analogues and chemically synthetic forms of these families of compounds. One particularly preferred derivative is an angeloyl derivative of ingenane.

The preferred chemical agent of the present invention is one which exhibits an effect on a protein kinase C (PKC) enzyme. Such an effect may be a direct activation or inhibition of PKC activity or a direct effect on the levels of PKC enzyme in a cell or exported from a cell. Furthermore, the effect may be transitory or may involve an initial activation of PKC activity or PKC enzyme synthesis or induction of a functional conformation followed by a down-regulation of PKC activity, enzyme levels or formation of a deactivated conformation. Consequently, an effect on PKC is regarded herein as a modulatory effect and is conveniently determined by consequential events such as resulting from altered signal transduction. For example, activation of immune mechanisms or activation of a gene promoter may occur and this is regarded herein as a modulatory effect on PKC.

The chemical agents of the present invention may be in purified or isolated form meaning that the preparation is substantially devoid of other compounds or contaminating agents other than diluent, solvent or carrier or isoforms of the agents. Furthermore, the term "chemical agent" includes preparations of two or more compounds either admixed together or co-purified from a particular source. The chemical agent may also be a chemical fraction, extract or other preparation from the Euphorbiaceace plant.

Consequently, reference herein to a "chemical agent" includes a purified form of one or more compounds or a chemical fraction or extract such as from the sap of a Euphorbiaceace plant, and in particular a species of *Euphorbia*, and most preferably from *E. peplus* or botanical or horticultural relatives or variants thereof.

Accordingly, one aspect of the present invention contemplates a method for the treatment or prophylaxis of an inflammatory condition in an subject, said method comprising the administration to said subject of a symptom-ameliorating effective amount of a chemical agent obtainable from a plant of the Euphorbiaceae family or a derivative or chemical analogue thereof which chemical agent is a macrocyclic diterpene selected from compounds of the ingenane, pepluane and jatrophane families and which chemical agent or derivative or chemical analogue is represented by any one of the general formulae (I)-(V)

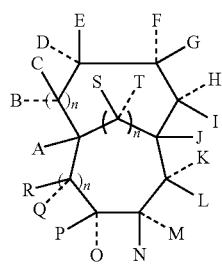

I wherein:

n is 0-10 atoms selected from carbon, oxygen, nitrogen, sulfur, phosphorus, silicon, boron, arsenic and selenium, wherein the ring defined by said atoms is saturated or unsaturated, including epoxides and thioepoxides;

A-T are independently selected from hydrogen, $R_1$, $R_2$, $R_3$, F, Cl, Br, I, CN, $OR_1$, $SR_1$, $NR_1R_2$, $N(=O)_2$, $NR_1OR_2$, $ONR_1R_2$, $SOR_1$, $SO_2R_1$, $SO_3R_1$, $SONR_1R_2$, $SO_2NR_1R_2$, $SO_3NR_1R_2$, $P(R_1)_3$, $P(=O)(R_1)_3$, $Si(R_1)_3$, $B(R_1)_2$, $(C=X)R_3$ or $X(C=X)R_3$ where X is selected from sulfur, oxygen and nitrogen;

$R_1$ and $R_2$ are each independently selected from $C_1$-$C_{20}$ alkyl (branched and/or straight chained), $C_1$-$C_{20}$ arylalkyl, $C_3$-$C_8$ cycloalkyl, $C_6$-$C_{14}$ aryl, $C_1$-$C_{14}$ heteroaryl, $C_1$-$C_{14}$ heterocycle, $C_2$-$C_{10}$ alkenyl (branched and/or straight chained), $C_2$-$C_{10}$ alkynyl (branched and/or straight chained), $C_1$-$C_{10}$ heteroarylalkyl, $C_1$-$C_{10}$ alkoxyalkyl, $C_1$-$C_{10}$ haloalkyl, dihaloalkyl, trihaloalkyl, haloalkoxy, $C_1$-$C_{10}$ [CN, $OR_1$, $SR_1$, $NR_1R_2$, $N(=O)_2$, $NR_1OR_2$, $ONR_1R_2$, $SOR_1$, $SO_2R_1$, $SO_3R_1$, $SONR_1R_2$, $SO_2NR_1R_2$, $SO_3NR_1R_2$, $P(R_1)_3$, $P(=O)(R_1)_3$, $Si(R_1)_3$, $B(R_1)_2$]alkyl;

$R_3$ is selected from $R_1$, $R_2$, CN, $COR_1$, $CO_2R_1$, $OR_1$, $SR_1$, $NR_1R_2$, $N(=O)_2$, $NR_1OR_2$, $ONR_1R_2$, $SOR_1$, $SO_2R_1$, $SO_3R_1$, $SONR_1R_2$, $SO_2NR_1R_2$, $SO_3NR_1R_2$, $P(R_1)_3$, $P(=O)(R_1)_3$, $Si(R_1)_3$, $B(R_1)_2$;

A connected to B (or C), D (or E), R (or Q), P (or O) or S (or T) is a selection of $C_1$-$C_8$ disubstituted (fused) saturated or unsaturated carbocyclic or heterocyclic rings further substituted by $R_3$, $(C=X)R_3$ and $X(C=X)R_3$, including epoxides and thioepoxides;

J connected to I (or H), G (or F), K (or L), M (or N) or S (or T) is a selection of $C_1$-$C_8$ disubstituted (fused) saturated and unsaturated carbocyclic or heterocyclic rings further substituted by $R_3$, $(C=X)R_3$ and $X(C=X)R_3$, including epoxides and thioepoxides;

D (or E) connected to B (or C) or G (or F); I (or H) connected to G (or F); P (or O) connected to R (or Q) or M (or N); K (or L) connected to N (or M) is a selection of $C_1$-$C_8$ disubstituted (fused) saturated or unsaturated carbocyclic or heterocyclic rings substituted by $R_3$, $(C=X)R_3$ and $X(C=X)R_3$, including epoxides and thioepoxides;

B and C, D and E, R and Q, P and O, I and H, G and F, K and L, M and N or S and T are =X where X is selected from sulfur, oxygen, nitrogen, $NR_1R_2$, and $=CR_1R_2$

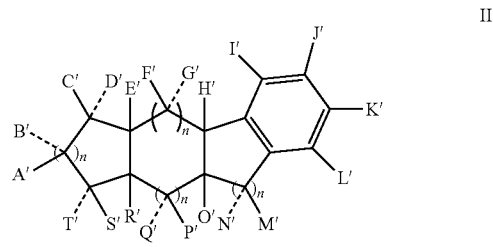

II wherein:

n is 0-10 atoms selected from carbon, oxygen, nitrogen, sulfur, phosphorus, silicon, boron, arsenic and selenium, wherein the ring defined by said atoms is saturated or unsaturated, including epoxides and thioepoxides;

A'-T' are independently selected from hydrogen, $R_4$, $R_5$, $R_6$, F, Cl, Br, I, CN, $COR_4$, $CO_2R_4$, $OR_4$, $SR_4$, $NR_4R_5$, $CONR_4R_5$, $N(=O)_2$, $NR_4OR_5$, $ONR_4R_5$, $SOR_4$, $SO_2R_4$, $SO_3R_4$, $SONR_4R_5$, $SO_2NR_4R_5$, $SO_3NR_4R_5$, $P(R_4)_3$, $P(=O)(R_4)_3$, $Si(R_4)_3$, $B(R_4)_2$, $(C=X)R_6$ or $X(C=X)R_6$ where X is selected from sulfur, oxygen and nitrogen;

$R_4$ and $R_5$ are each independently selected from $C_1$-$C_{20}$ alkyl (branched and/or straight chained), $C_1$-$C_{20}$ arylalkyl, $C_3$-$C_8$ cycloalkyl, $C_6$-$C_{14}$ aryl, $C_1$-$C_{14}$ heteroaryl, $C_1$-$C_{14}$ heterocycle, $C_2$-$C_{10}$ alkenyl (branched and/or straight chained), $C_2$-$C_{10}$ alkynyl (branched and/or straight chained), $C_1$-$C_{10}$ heteroarylalkyl, $C_1$-$C_{10}$ alkoxyalkyl, $C_1$-$C_{10}$ haloalkyl, dihaloalkyl, trihaloalkyl, haloalkoxy, $C_1$-$C_{10}$ [CN, $OR_4$, $SR_4$, $NR_4R_5$, $N(=O)_2$, $NR_4OR_5$, $ONR_4R_5$, $SOR_4$, $SO_2R_4$, $SO_3R_4$, $SONR_4R_5$, $SO_2NR_4R_5$, $SO_3NR_4R_5$, $P(R_4)_3$, $P(=O)(R_4)_3$, $Si(R_4)_3$, $B(R_4)_2$]alkyl;

$R_6$ is selected from $R_4$, $R_5$, CN, $COR_4$, $CO_2R_4$, $OR_4$, $SR_4$, $NR_4R_5$, $N(=O)_2$, $NR_4OR_5$, $ONR_4R_5$, $SOR_4$, $SO_2R_4$, $SO_3R_4$, $SONR_4R_5$, $SO_2NR_4R_5$, $SO_3NR_4R_5$, $P(R_4)_3$, $P(=O)(R_4)_3$, $Si(R_4)_3$, $B(R_4)_2$;

E' and R' or H' and O' is a $C_2$-$C_8$ saturated or unsaturated carbocyclic or heterocyclic ring system further substituted by $R_6$, including epoxides and thioepoxides;

O' connected to M' (or N') or Q (or P'); R' connected to Q' (or P') or S' (or T'); S' (or T') connected to A' (or B'); A' (or B') connected to C' (or D'); E' connected to C' (or D') or F' (or G'); H' connected to I'; I' connected to J'; J' connected to K'; K' connected to L'; L' connected to M' (or N') are $C_1$-$C_8$ disubstituted (fused) saturated or unsaturated carbocyclic or heterocyclic ring systems further substituted by $R_6$, $(C=X)R_6$ and $X(C=X)R_6$, including epoxides and thioepoxides;

A', B' and C', D' and F', G' and M', N' and P', Q and S', T' are =X where X is selected from sulfur, oxygen, nitrogen, $NR_4R_5$, $(C=X)R_6$, $X(C=X)R_6$, and $=CR_7R_8$;

$R_7$ and $R_8$ are each independently selected from $R_6$, $(C=X)R_6$ and $X(C=X)R_6$

III

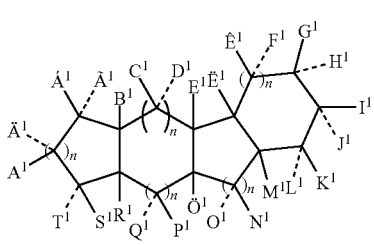

wherein:
n is 0-10 atoms selected from carbon, oxygen, nitrogen, sulfur, phosphorus, silicon, boron, arsenic and selenium, wherein the ring defined by said atoms is saturated or unsaturated, including epoxides and thioepoxides;

$A^1$-$T^1$ are independently selected from hydrogen, $R_9$, $R_{10}$, $R_{11}$, F, Cl, Br, I, CN, $OR_9$, $SR_9$, $NR_9R_{10}$, $N(=O)_2$, $NR_9OR_{10}$, $ONR_9R_{10}$, $SOR_9$, $SO_2R_9$, $SO_3R_9$, $SONR_9R_{10}$, $SO_2NR_9R_{10}$, $SO_3NR_9R_{10}$, $P(R_9)_3$, $P(=O)(R_9)_3$, $Si(R_9)_3$, $B(R_9)_2$, $(C=X)R_{11}$ or $X(C=X)R_{11}$ where X is selected from sulfur, oxygen and nitrogen;

$R_9$ and $R_{10}$ are each independently selected from $C_1$-$C_{20}$ alkyl (branched and straight chained), $C_1$-$C_{20}$ arylalkyl, $C_3$-$C_8$ cycloalkyl, $C_6$-$C_{14}$ aryl, $C_1$-$C_{14}$ heteroaryl, $C_1$-$C_{14}$ heterocycle, $C_2$-$C_{10}$ alkenyl (branched and straight chained), $C_2$-$C_{10}$ alkynyl (branched and straight chained), $C_1$-$C_{10}$ heteroarylalkyl, $C_1$-$C_{10}$ alkoxyalkyl, $C_1$-$C_{10}$ haloalkyl, dihaloalkyl, trihaloalkyl, haloalkoxy, $C_1$-$C_{10}$ [CN, $OR_9$, $SR_9$, $NR_9R_{10}$, $N(=O)_2$, $NR_9OR_{10}$, $ONR_9R_{10}$, $SOR_9$, $SO_2R_9$, $SO_3R_9$, $SONR_9R_{10}$, $SO_2NR_9R_{10}$, $SO_3NR_9R_{10}$, $P(R_9)_3$, $P(=O)(R_9)_3$, $Si(R_9)_3$, $B(R_9)_2$]alkyl;

$R_{11}$ is selected from $R_9$, $R_{10}$, CN, $COR_9$, $CO_2R_9$, $OR_9$, $SR_9$, $NR_9R_{10}$, $N(=O)_2$, $NR_9OR_{10}$, $ONR_9R_{10}$, $SOR_9$, $SO_2R_9$, $SO_3R_9$, $SONR_9R_{10}$, $SO_2NR_9R_{10}$, $SO_3NR_9R_{10}$, $P(R_9)_3$, $P(=O)(R_9)_3$, $Si(R_9)_3$, $B(R_9)_2$;

$B^1$ and $R^1$, $E^1$ and $Ö^1$ and $Ë^1$ and $M^1$ are selected from a $C_2$-$C_8$ saturated or unsaturated carbocyclic or heterocyclic ring system further substituted by $R_{11}$, including epoxides and thioepoxides;

$A^1$ (or $Ä^1$) connected to $Á^1$ (or $Ã^1$) or $T^1$ (or $S^1$); $B^1$ connected to $Á^1$ (or $Ã^1$) or $C^1$ (or $D^1$). $E^1$ connected to $Ë^1$ or $C^1$ (or $D^1$); $Ë^1$ connected to $É^1$ (or $F^1$); $G^1$ (or $H^1$) connected to $É^1$ (or $F^1$) or $I^1$ (or $J^1$); $K^1$ (or $L^1$) connected to $I^1$ (or $J^1$) or $M^1$; $M^1$ connected to $O^1$ (or $N^1$); $Ö^1$ connected $O^1$ (or $N^1$) or $P^1$ (or $Q^1$); $R^1$ connected $P^1$ (or $Q^1$) or $S^1$ (or $T^1$) are $C_1$-$C_8$ disubstituted (fused) saturated or unsaturated carbocyclic or heterocyclic ring systems further substituted by $R_H$, $(C=X)R_{11}$ and $X(C=X)R_{11}$, including epoxides and thioepoxides;

$A^1$, $Ä$ and $Á$, $Ã$ and $C^1$, $D^1$ and $F^1$, $E$ and $G^1$, $H^1$ and h $J^1$ and $K^1$, $L^1$ and $N^1$, $O^1$ and $P^1$, $Q^1$ and $S^1$, $T^1$ are $=X$ where X is selected from sulfur, oxygen, nitrogen, $NR_9R_{10}$, including $(C=X)R_{11}$ and $X(C=X)R_{11}$, and $=CR_{12}R_{13}$;

$R_{12}$ and $R_{13}$ are independently selected from $R_{11}$, $(C=X)R_{11}$ and $X(C=X)R_{11}$

IV

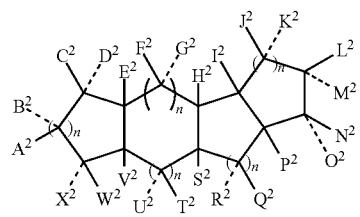

wherein:
n is 0-10 atoms selected from carbon, oxygen, nitrogen, sulfur, phosphorus, silicon, boron, arsenic and selenium, wherein the ring defined by said atoms is saturated or unsaturated, including epoxides and thioepoxides;

$A^2$-$X^2$ are independently selected from hydrogen, $R_{14}$, $R_{15}$, $R_{16}$, F, Cl, Br, I, CN, $OR_{14}$, $SR_{14}$, $NR_{14}R_{15}$, $N(=O)_2$, $NR_{14}OR_{15}$, $ONR_{14}R_{15}$, $SOR_{14}$, $SO_2R_{14}$, $SO_3R_{14}$, $SONR_{14}R_{15}$, $SO_2NR_{14}R_{15}$, $SO_3NR_{14}R_{15}$, $P(R_{14})_3$, $P(=O)(R_{14})_3$, $Si(R_{14})_3$, $B(R_{14})$, $(C=Y)R_{16}$ or $Y(C=Y)R_{16}$ where Y is selected from sulfur, oxygen and nitrogen;

$R_{14}$ and $R_{15}$ are each independently selected from $C_1$-$C_{20}$ alkyl (branched and/or straight chained), $C_1$-$C_{20}$ arylalkyl, $C_3$-$C_8$ cycloalkyl, $C_6$-$C_{14}$ aryl, $C_1$-$C_{14}$ heteroaryl, $C_1$-$C_{14}$ heterocycle, $C_2$-$C_{10}$ alkenyl (branched and/or straight chained), $C_2$-$C_{10}$ alkynyl (branched and/or straight chained), $C_1$-$C_{10}$ heteroarylalkyl, $C_1$-$C_{10}$ alkoxyalkyl, $C_1$-$C_{10}$ haloalkyl, dihaloalkyl, trihaloalkyl, haloalkoxy, $C_1$-$C_{10}$ [CN, $OR_{14}$, $SR_{14}$, $NR_{14}R_{10}$, $N(=O)_2$, $NR_{14}OR_{15}$, $ONR_{14}R_{15}$, $SOR_{14}$, $SO_2R_{14}$, $SO_3R_{14}$, $SONR_{14}R_{15}$, $SO_2NR_{14}R_{15}$, $SO_3NR_{14}R_{15}$, $P(R_{14})_3$, $P(=O)(R_{14})_3$, $Si(R_{14})_3$, $B(R_{14})_2$]alkyl;

$R_{16}$ is selected from $R_{14}$, $R_{15}$, CN, $COR_{14}$, $CO_2R_{15}$, $OR_{14}$, $SR_{14}$, $NR_{14}R_{15}$, $N(=O)_2$, $NR_{14}OR_{15}$, $ONR_{14}R_{15}$, $SOR_{14}$, $SO_2R_{14}$, $SO_3R_{14}$, $SONR_{14}R_{15}$, $SO_2NR_{14}R_{15}$, $SO_3NR_{14}R_{15}$, $P(R_{14})_3$, $P(=O)(R_{14})_3$, $Si(R_{14})_3$, $B(R_{14})_2$;

$E^2$ and $V^2$, $H^2$ and $S^2$, and $I^2$ and $P^2$ are $C_2$-$C_8$ saturated or unsaturated carbocyclic or heterocyclic ring system further substituted by $R_{16}$, including epoxides and thioepoxides;

$A^2$ (or $B^2$) connected to $C^2$ (or $D^2$) or $W^2$ (or $X^2$); $E^2$ connected to $C^2$ (or $D^2$) or $F^2$ (or $G^2$); $H^2$ connected to $F^2$ (or $G^2$) or $I^2$; $I^2$ connected to $J^2$ (or $K^2$); $L^2$ (or $M^2$) connected to $J^2$ (or $K^2$) or $N^2$ (or $O^2$); $R^2$ (or $Q^2$) connected to $P^2$ or $S^2$; $V^2$ connected to $U^2$ (or $T^2$) or $W^2$ (or $X^2$) are $C_1$-$C_8$ disubstituted (fused) saturated or unsaturated carbocyclic or heterocyclic ring systems further substituted by $R_{16}$, $(C=Y)R_{16}$ and $Y(C=Y)R_{16}$, including epoxides and thioepoxides;

$A^2$, $B^2$; $C^2$, $D^2$; $F^2$ $G^2$; $J^2$, $K^2$; $L^2$, $M^2$; $N^2$, $O^2$; $Q^2$, $R^2$; $U^2$, $T^2$ and $X^2$, $W^2$ are $=Y$ where Y is selected from sulfur, oxygen, nitrogen, $NR_{14}R_{15}$ and $=CR_{17}R_{18}$;

$R_{17}$ and $R_{18}$ are independently selected from $R_{16}$, $(C=Y)R_{16}$ and $Y(C=Y)R_{16}$

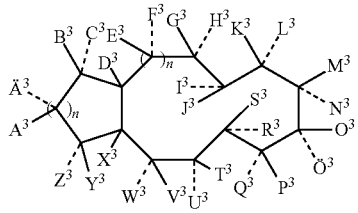

V wherein:
n is 0-10 atoms selected from carbon, oxygen, nitrogen, sulfur, phosphorus, silicon, boron, arsenic and selenium, wherein the ring defined by said atoms is saturated or unsaturated, including epoxides and thioepoxides;

$A^3$-$Z^3$ are independently selected from hydrogen, $R_{19}$, $R_{20}$, $R_{21}$, F, Cl, Br, I, CN, $OR_{19}$, $SR_{19}$, $NR_{19}OR_{20}$, $N(=O)_2$, $NR_{19}OR_{20}$, $ONR_{19}R_{20}$, $SOR_{19}$, $SO_2R_{19}$, $SO_3R_{19}$, $SONR_{19}R_{20}$, $SO_2NR_{19}R_{20}$, $SO_3NR_{19}R_{20}$, $P(R_{19})_3$, $P(=O)(R_{19})_3$, $Si(R_{19})_3$, $B(R_{19})_2$, $(C=\emptyset)R_{21}$ or $\emptyset(C=\emptyset)R_{21}$ where $\emptyset$ is sulfur, oxygen and nitrogen;

$R_{19}$ and $R_{20}$ are each independently selected from $C_1$-$C_{20}$ alkyl (branched and/or straight chained), $C_1$-$C_{20}$ aralkyl, $C_3$-$C_8$ cycloalkyl, $C_6$-$C_{14}$ aryl, $C_1$-$C_{14}$ heteroaryl, $C_1$-$C_{14}$ heterocycle, $C_2$-$C_{10}$ alkenyl (branched and/or straight chained), $C_2$-$C_{10}$ alkynyl (branched and/or straight chained), $C_1$-$C_{10}$ heteroarylalkyl, $C_1$-$C_{10}$ alkoxyalkyl, $C_1$-$C_{10}$ haloalkyl, dihaloalkyl, trihaloalkyl, haloalkoxy, $C_1$-$C_{10}$ [CN, $OR_{19}$, $SR_{19}$, $NR_{19}OR_{20}$, $N(=O)_2$, $NR_{19}OR_{20}$, $ONR_{19}OR_{20}$, $SOR_{19}$, $SO_2R_{19}$, $SO_3R_{19}$, $SONR_{19}OR_{20}$, $SO_2NR_{19}R_{20}$, $SO_3NR_{19}OR_{20}$, $P(R_{19})_3$, $P(=O)(R_{19})_3$, $Si(R_{19})_3$, $B(R_{19})_2$]alkyl;

$R_{21}$ is selected from $R_{19}$, $R_{20}$, CN, $COR_{19}$, $CO_2R_{19}$, $OR_{19}$, $SR_{19}$, $NR_{19}R_{20}$, $N(=O)_2$, $NR_{19}OR_{20}$, $ONR_{19}R_{20}$, $SOR_{19}$, $SO_2R_{19}$, $SO_3R_{19}$, $SONR_{19}R_{20}$, $SO_2NR_{19}R_{20}$, $SO_3NR_{19}R_{20}$, $P(R_{19})_3$, $P(=O)(R_{19})_3$, $Si(R_{19})_3$, $B(R_{19})_2$;

$D^3$ connected to $X^3$ is a $C_2$-$C_8$ saturated or unsaturated carbocyclic or heterocyclic ring system further substituted by $R_{21}$, including epoxides and thioepoxides;

$A^3$ (or $Ä^3$) connected to $B^3$ (or $C^3$) or $Z^3$ (or $Y^3$); $D^3$ connected to $B^3$ (or $C^3$) or $E^3$ (or $F^3$); $G^3$ (or $H^3$) connected to $E^3$ (or $F^3$) or $I^3$ (or $J^3$); $L^3$ (or $K^3$) connected to $I^3$ (or $J^3$) or $M^3$ (or $N^3$); $O^3$ (or $Ö^3$) connected to $N^3$ (or $M^3$) or $P^3$ (or $Q^3$). $S^3$ (or $R^3$) connected to $Q^3$ (or $P^3$) or $U^3$ (or $T^3$). $W^3$ (or $V^3$) connected to $U^3$ (or $T^3$) or $X^3$; $X^3$ connected to $Y^3$ (or $Z^3$) are $C_1$-$C_8$ disubstituted (fused) saturated or unsaturated carbocyclic or heterocyclic ring systems further substituted by $R_{21}$, $(C=\emptyset)R_{21}$ and $\emptyset(C=\emptyset)R_{21}$, including epoxides and thioepoxides;

$A^3$, $Ä^3$; $B^3$, $C^3$; $E^3$, $F^3$; $G^3$, $H^3$; $I^3$, $J^3$; $K^3$, $L^3$; $M^3$, $N^3$; $O^3$, $Ö^3$; $Q^3$, $P^3$, $S^3$, $R^3$, $U^3$, $T^3$, $W^3$, $V^3$, and $Z^3$, $Y^3$ are =$\emptyset$ where $\emptyset$ is selected from sulfur, oxygen, nitrogen, $NR_{19}R_{20}$, and =$CR_{22}R_{23}$; and $R_{22}$ and $R_{23}$ are selected from $R_{21}$, $(C=\emptyset)R_{21}$ and $\emptyset(C=\emptyset)R_{21}$;

and which chemical agent or derivative or chemical analogue thereof is capable of modulating PKC activity, PKC-dependent gene expression or PKC enzyme turnover and wherein said chemical agent or its derivatives or chemical analogues is administered for a time and under conditions sufficient to ameliorate one or more symptoms associated with said inflammatory condition.

In a related embodiment, the present invention contemplates a method for immunopotentiation of a subject, said method comprising administering to said subject an effective amount of a chemical agent represented by any one of the general formulae (I)-(V) as defined above and which chemical agent or derivative or chemical analogue thereof is capable of modulating PKC activity, PKC-dependent gene expression or PKC enzyme turnover and wherein said chemical agent or its derivatives or chemical analogues is administered for a time and under conditions sufficient to potentiate the immune system or components therein.

Especially preferred chemical agents or derivatives or chemical analogues thereof are represented by the general formula (VI):—

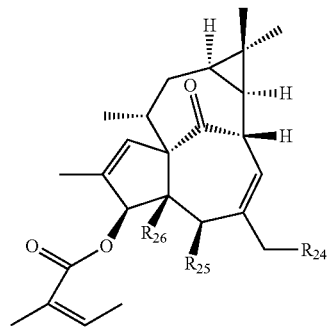

VI wherein:—
$R_{24}$, $R_{25}$ and $R_{26}$ are independently selected from hydrogen, $R_{27}$, $R_{28}$, F, Cl, Br, I, CN, $OR_{27}$, $SR_{27}$, $NR_{27}R_{28}$, $N(=O)_2$, $NR_{27}OR_{28}$, $ONR_{27}R_{28}$, $SOR_{27}$, $SO_2R_{27}$, $SO_3R_{27}$, $SONR_{27}R_{28}$, $SO_3NR_{27}R_{28}$, $SO_3NR_{27}R_{28}$, $P(R_{27})_3$, $P(=O)(R_{27})_3$, $Si(R_{27})_3$, $B(R_{27})_2$, $(C=X)R_{29}$ or $X(C=X)R_{29}$ where X is selected from sulfur, oxygen and nitrogen;

$R_{27}$ and $R_{28}$ are each independently selected from $C_1$-$C_{20}$ alkyl (branched and/or straight chained), $C_1$-$C_{20}$ aralkyl, $C_3$-$C_8$ cycloalkyl, $C_6$-$C_{14}$ aryl, $C_1$-$C_{14}$ heteroaryl, $C_1$-$C_{14}$ heterocycle, $C_2$-$C_{10}$ alkenyl (branched and/or straight chained), $C_2$-$C_{10}$ alkynyl (branched and/or straight chained), $C_1$-$C_{10}$ heteroarylalkyl, $C_1$-$C_{10}$ alkoxyalkyl, $C_1$-$C_{10}$ haloalkyl, dihaloalkyl, trihaloalkyl, haloalkoxy, $C_1$-$C_{10}$ [CN, $OR_{27}$, $SR_{27}$, $NR_{27}R_{28}$, $N(=O)_2$, $NR_{27}OR_{28}$, $ONR_{27}R_{28}$, $SOR_{27}$, $SO_2R_{27}$, $SO_3R_{27}$, $SONR_{27}R_{28}$, $SO_2NR_{27}R_{28}$, $SO_3NR_{27}R_{28}$, $P(R_{27})_3$, $P(=O)(R_{27})_3$, $Si(R_{27})_3$, $B(R_{27})_2$]alkyl;

$R_{29}$ is selected from $R_{27}$, $R_{28}$, CN, $COR_{27}$, $CO_2R_{27}$, $OR_{27}$, $SR_{27}$, $NR_{27}R_{28}$, $N(=O)_2$, $NR_{27}OR_{28}$, $ONR_{27}R_{28}$, $SOR_{27}$, $SO_2R_{27}$, $SO_3R_{27}$, $SONR_{27}R_{28}$, $SO_2NR_{27}R_{28}$, $SO_3NR_{27}R_{28}$, $P(R_{27})_3$, $P(=O)(R_{27})_3$, $Si(R_{27})_3$, $B(R_{27})_2$.

In a preferred embodiment, $R_{24}$ is hydrogen, OAcetyl or OH.

In another preferred embodiment, $R_{25}$ and $R_{26}$ are OH.

As used herein, the term "alkyl" refers to linear or branched chains. The term "haloalkyl" refers to an alkyl group substituted by at least one halogen. Similarly, the term "haloalkoxy" refers to an alkoxy group substituted by at least one halogen. As used herein the term "halogen" refers to fluorine, chlorine, bromine and iodine.

As used herein the term "aryl" refers to aromatic carbocyclic ring systems such as phenyl or naphthyl, anthracenyl, especially phenyl. Suitably, aryl is $C_6$-$C_{14}$ with mono, di- and tri-substitution containing F, Cl, Br, I, $NO_2$, $CF_3$, CN, $OR_1$, $COR_1$, $CO_2R_1$, $NHR_1$, $NR_1R_2$, $NR_1OR_2$, $ONR_1R_2$, $SOR_1$, $SO_2R_1$, $SO_3R_1$, $SONR_1R_2$, $SO_2NR_1R_2$, $SO_3NR_1R_2$, $P(R_1)_3$, $P(=O)(R_1)_3$, $Si(R_1)_3$, $B(R_1)_2$, wherein $R_1$ and $R_2$ are defined above As used herein the terms "heterocycle", "heterocyclic", "heterocyclic systems" and the like refer to a saturated, unsaturated, or aromatic carbocyclic group having a single ring, multiple fused rings (for example, bicyclic, tricyclic, or other similar bridged ring systems or substituents), or multiple condensed rings, and having at least one heteroatom such as nitrogen, oxygen, or sulfur within at least one of the rings. This term also includes "heteroaryl" which refers to a heterocycle in which at least one ring is aromatic. Any heterocyclic or heteroaryl group can be unsubstituted or optionally substituted with one or more groups, as defined above. Further, bi- or tricyclic heteroaryl moieties may comprise at least one ring, which is either completely, or partially, saturated. Suitable heteroaryl moieties include, but are not limited to oxazolyl, thiazaoyl, thienyl, furyl, 1-isobenzofuranyl, 3H-pyrrolyl, 2H-pyrrolyl, N-pyrrolyl, imidazolyl, pyrazolyl, isothiazolyl, isooxazolyl, pyridyl, pyrazinyl, pyrimidinyl, pyradazinyl, indolizinyl, isoindolyl, indoyl, indolyl, purinyl, phthalazinyl, 1,2,3-triazolyl, 1,2,4-triazolyl, 1,2,3-oxadiazoyl, 1,2,4-oxadiazolyl, 1,2,5-oxadiazolyl, 1,3,4-oxadiazolyl, 1,2,3,4-oxatriazolyl, 1,2,3,5-oxatriazolyl, 1,3,5-triazinyl, 1,2,4-triazinyl, 1,2,3-triazinyl, azepinyl, oxepinyl, thiepinyl, benzofuranyl, isobenzofuranyl, thionaphthenyl, isothionaphthenyl, indoleninyl, 2-isobenzazolyl, 1,5-pyrindinyl, pyrano[3,4-b]pyrrolyl, isoindazolyl, indoxazinyl, benzoxazolyl, anthranilyl, quinolinyl, isoquinolinyl, cinnolinyl, quinazolinyl, naphthyridinyl, pyrido[3,4-b]pyridinyl, and pyrido[3,2-b]pyridinyl, pyrido[4,3-b]pyridinyl.

Reference to an inflammatory condition including both therapeutically useful inflammation (e.g. immunopotentiation) and clinically adverse inflammation. Immunopotentiation of the immune system is useful in immune-compromised subjects as well as for treating infection by pathogenic organisms or potentially pathogenic organisms.

According to the latter embodiment, there is provided a method for the immunopotentiation of a subject in the treatment and prophylaxis of said subject for infection by a pathogenic organism or a potential pathogenic organism, said method comprising the administration to said subject of a symptom-ameliorating effective amount of a macrocyclic diterpene, or a chemical fraction comprising same from a plant of the family Euphorbiaceae or a derivative or chemical analogue of said macrocyclic diterpene having the structures as defined above wherein said macrocyclic diterpene or its derivative or chemical analogue modulates PKC activity, synthesis or enzyme turnover, said administration being for a time and under conditions sufficient to potentiate components of the immune system.

A pathogenic organism or a potential pathogenic organism includes prokaryotic microorganism, a lower eukaryotic microorganism, a complex eukaryotic organism or a virus.

A prokaryotic microorganism includes bacteria such as Gram positive, Gram negative and Gram variable bacteria and intracellular bacteria. Examples of bacteria contemplated herein include the species of the genera *Treponema* sp., *Borrelia* sp., *Neisseria* sp., *Legionella* sp., *Bordetella* sp., *Escherichia* sp., *Salmonella* sp., *Shigella* sp., *Klebsiella* sp., *Yersinia* sp., *Vibrio* sp., *Hemophilus* sp., *Rickettsia* sp., *Chlamydia* sp., *Mycoplasma* sp., *Staphylococcus* sp., *Streptococcus* sp., *Bacillus* sp., *Clostridium* sp., *Corynebacterium* sp., *Proprionibacterium* sp., *Mycobacterium* sp., *Ureaplasma* sp. and *Listeria* sp.

Particularly preferred species include *Treponema pallidum*, *Borrelia burgdorferi*, *Neisseria gonorrhea*, *Neisseria meningitidis*, *Legionella pneumophila*, *Bordetella pertussis*, *Escherichia coli*, *Salmonella typhi*, *Salmonella typhimurium*, *Shigella dysenteriae*, *Klebsiella pneumoniae*, *Yersinia pestis*, *Vibrio cholerae*, *Hemophilus influenzae*, *Rickettsia rickettsii*, *Chlamydia trachomatis*, *Mycoplasma pneumoniae*, *Staphylococcus aureus*, *Streptococcus pneumoniae*, *Streptococcus pyogenes*, *Bacillus anthracis*, *Clostridium botulinum*, *Clostridium tetani*, *Clostridium perfringens*, *Corynebacterium diphtheriae*, *Proprionibacterium acnes*, *Mycobacterium tuberculosis*, *Mycobacterium leprae* and *Listeria monocytogenes*.

A lower eukaryotic organism includes a yeast or fungus such as but not limited to *Pneumocystis carinii*, *Candida albicans*, *Aspergillus*, *Histoplasma capsulatum*, *Blastomyces dermatitidis*, *Cryptococcus neoformans*, *Trichophyton* and *Microsporum*.

A complex eukaryotic organism includes worms, insects, arachnids, nematodes, aemobe, *Entamoeba histolytica*, *Giardia lamblia*, *Trichomonas vaginalis*, *Trypanosoma brucei gambiense*, *Trypanosoma cruzi*, *Balantidium coli*, *Plasmodium malariae*, *Plasmodium tropicalis*, *Toxoplasma gondii*, *Cryptosporidium* or *Leishmania*.

The term "viruses" is used in its broadest sense to include viruses of the families adenoviruses, papovaviruses, herpesviruses simplex, varicella-zoster, Epstein-Barr, CMV, pox viruses: smallpox, vaccinia, hepatitis B, rhinoviruses, hepatitis A, poliovirus, rubellavirus, hepatitis C, arboviruses, rabiesvirus, influenzaviruses A and B, measlesvirus, mumpsvirus, HIV, HTLV I and II.

Particularly preferred prokaryotic microorganisms are *Salmonella* sp. and other enteric microorganisms and *Streptococcus* sp. and *Staphylococcus* sp. Particularly preferred lower eukaryotic organisms include species of *Trichophytos*, *Microsporum* and *Epidermophytos*, yeast and *Plasmodium* sp. such as malaria agents.

Preferred complex eukaroytic organisms are insects such as blood-sucking insects.

Preferred viruses are HIV, EBV and CMV.

Another aspect of the present invention provides a method for the treatment or prophylaxis of an inflammatory condition in a subject, said method comprising the administration to said subject of a symptom-ameliorating effective amount of a macrocyclic diterpene or chemical fraction comprising same from a plant of the family Euphorbiaceae or a derivative or chemical analogue of said macrocyclic diterpene having the structures as defined above wherein said macrocyclic diterpene or its derivative or chemical analogue modulates PKC activity, synthesis or enzyme turnover, said administration being for a time and under conditions sufficient to treat said inflammatory condition.

Inflammatory conditions include but are not limited to tissue and/or organ transplant rejection, sepsis, acute respiratory distress syndrome (ARDS), asthma, trauma, oxidative stress, cell death, irradiation damage, ischemia, reperfusion, cancer, viral infection, autoimmune disease, rheumatoid arthritis, psoriasis, inflammatory bowel disease, glomerulonephritis, lupus, uveitis, chronic hepatitis, juvenile diabetes, chronic non-suppurative thyroiditis, tuberculosis, syphilis, actinomycosis, sarcoidosis, amyloidosis, granulomatous thyroiditis, lymphocytic thyroiditis, Hashimoto's thyroiditis, invasive fibrous thyroiditis, Grave's disease, regional enteritis, Crohn's disease, granulomatous ileitis, ulcerative colitis, chorioretinal inflammatory syndrome, pancreatitis, synovitis of the hip, odynophagia, dysphagia, viral and bacterial pharyngitis, infectious mononucleosis, acute tonsillitis, peritonsillar abscess, ulcerative tonsillitis, lingual tonsillitis, Candidiasis, Epiglottitis, tracheobronchial inflammation, Ludwig's angina, idiopathic pulmonary fibrosis, interstitial lung disease, lichen planus, lichen sclerosus, abscess, meningitis, encephalitis, vasculitis, progressive multi-focal leukoencephalopathy, urticaria, spongiotic dermatitis, allergic contact dermatitis, dermatitis, chronic contact dermatitis, lichen simplex chronicus, atopic dermatitis, erythema multiforme, stevens-johnson syndrome, toxic epidermal necrolysis, discoid lupus erythematosus and acne vulgaris.

Particularly useful compounds in accordance with the invention include 5,8,9,10,14-pentaacetoxy-3-benzoyloxy-15-hydroxypepluane (pepluane), derivatives of said pepluane, jatrophanes of Conformation II including 2,3,5,7,15-pentaacetoxy-9-nicotinoyloxy-14-oxojatropha-6(17),11E-diene (jatrophane 1), derivatives of said jatrophane 1, 2,5,7,8,9,14-hexaacetoxy-3-benzoyloxy-15-hydroxy-jatropha-6(17),11E-diene (jatrophane 2), derivatives of said jatrophane 2, 2,5,14-triacetoxy-3-benzoyloxy-8,15-dihydroxy-7-isobutyroyloxy-9-nicotinoyloxy-jatropha-6(17), 11E-diene (jatrophane 3), derivatives of said jatrophane 3, 2,5,9,14-tetraacetoxy-3-benzoyloxy-8,15-dihydroxy-7-isobutyroyloxyjatropha-6(17),11E-diene) (jatrophane 4), derivatives of said jatrophane 4, 2,5,7,14-tetraacetoxy-3-benzoyloxy-8,15-dihydroxy-9-nicotinoyloxyjatropha-6(17), 11E-diene (jatrophane 5), derivatives of said jatrophane 5, 2,5,7,9,14-pentaacetoxy-3-benzoyloxy-8,15-dihydroxyjatropha-6(17),11E-diene (jatrophane 6), derivatives of said jatrophane 6, or pharmaceutically acceptable salts of these.

Even more particularly preferred compounds are angeloyl substituted ingenanes or derivatives thereof such as ingenol-3-angelate, 20-deoxy-ingenol-3-angelate, 20-O-acetyl-ingenol-3-angelate, or derivatives of said angelates, or pharmaceutically acceptable salts of these.

Still a further aspect of the present invention contemplates a method of assessing the suitability of a chemical agent from Euphorbiaceae for the practice of the present invention. Numerical values are assigned to chemical agents including fractions comprising the chemical agents as set forth, for example, in Table A:—

TABLE A

| Feature | Value |
|---|---|
| An ability to modulate PKC activity or effect | +1 |
| An ability to induce bipolar dendritic activity | +1 |
| An ability to displace phorbol dibutyrate from binding to PKC | +1 |
| An ability to induce respiratory burst in leucocytes | +1 |
| An ability to stimulate phagocytosis in peripheral blood mononuclear cells | +1 |
| Derived from a member of the Euphorbiacea family | +1 |
| Derived from E. peplus | +3 |
| Water extractible from the sap of Euphorbia sp. | +2 |
| An ability to activate latent virus | +4 |
| A lower tumor promotion activity than TPA/PMA | +2 |

The value for each feature is referred to as the Index Value ($I_V$).

The sum of $I_V$, i.e. $\Sigma I_V$, provides a potency of agent ($P_A$) value and this enables an analytical approach to screening and selecting compounds from Euphorbiaceae useful in the practice of the present invention.

In one example, 20-acetyl-ingenol-3 angelate exhibits a $P_A=\Sigma I_V=15$.

Accordingly, another aspect of the present invention contemplates a method for the treatment or prophylaxis of an inflammatory condition in a subject, said method comprising administration to said subject of a symptom-ameliorating effective amount of a macrocyclic diterpene obtainable from a Euphorbiaceae plant or its botanical or horticultural relative, said macrocyclic diterpene being selected from an ingenane, pepluane or jatrophane, or a derivative or chemical analogue thereof, having the structure represented by any one of the general formulae (I)-(V) as defined above and wherein said chemical agent exhibits a potency of agent ($P_A$) of >10, wherein the $P_A=\Sigma I_V$ where $I_V$ is a numerical value associated with a particular feature as listed below:—

| Feature | Value |
|---|---|
| An ability to modulate PKC activity or effect | +1 |
| An ability to induce bipolar dendritic activity | +1 |
| An ability to displace phorbol dibutyrate from binding to PKC | +1 |
| An ability to induce respiratory burst in leucocytes | +1 |
| An ability to stimulate phagocytosis in peripheral blood mononuclear cells | +1 |
| Derived from a member of the Euphorbiacea family | +1 |
| Derived from E. peplus | +3 |
| Water extractible from the sap of Euphorbia sp. | +2 |
| An ability to activate latent virus | +4 |
| A lower tumor promotion activity than TPA/PMA | +2 | or pharmaceutically acceptable salts of these, said chemical agent being administered for a time and under conditions sufficient to ameliorate at least one symptom caused by or associated with inflammation.

In another embodiment, the invention contemplates a method for immunopotentiating a subject, said method comprising administration to said subject of a potentiating effective amount of a macrocyclic diterpene obtainable from a Euphorbiaceae plant or its botanical or horticultural relative, said macrocyclic diterpene being selected from an ingenane, pepluane or jatrophane, or a derivative or chemical analogue thereof, having the structure represented by any one of the general formulae (I)-(V) as defined above and wherein said chemical agent exhibits a potency of agent ($P_A$) of >10, wherein the $P_A=\Sigma I_V$ where $I_V$ is a numerical value associated with a particular feature as listed below:—

| Feature | Value |
|---|---|
| An ability to modulate PKC activity or effect | +1 |
| An ability to induce bipolar dendritic activity | +1 |
| An ability to displace phorbol dibutyrate from binding to PKC | +1 |
| An ability to induce respiratory burst in leucocytes | +1 |
| An ability to stimulate phagocytosis in peripheral blood mononuclear cells | +1 |
| Derived from a member of the Euphorbiaceae family | +1 |
| Derived from E. peplus | +3 |
| Water extractible from the sap of Euphorbia sp. | +2 |
| An ability to activate latent virus | +4 |
| A lower tumor promotion activity than TPA/PMA | +2 | or pharmaceutically acceptable salts of these, said chemical agent being administered for a time and under conditions sufficient to immunopotentiate said subject.

Preferred compounds are selected from the list comprising:—

5,8,9,10,14-pentaacetoxy-3-benzoyloxy-15-hydroxypepluane (pepluane);

2,3,5,7,15-pentaacetoxy-9-nicotinoyloxy-14-oxojatropha-6(17),11E-diene (jatrophane 1);

2,5,7,8,9,14-hexaacetoxy-3-benzoyloxy-15-hydroxy-jatropha-6(17),11E-diene (jatrophane 2);

2,5,14-triacetoxy-3-benzoyloxy-8,15-dihydroxy-7-isobutyroyloxy-9-nicotinoyloxy-jatropha-6(17),11E-diene (jatrophane 3);

2,5,9,14-tetraacetoxy-3-benzoyloxy-8,15-dihydroxy-7-isobutyroyloxy-jatropha-6(17),11E-diene) (jatrophane 4);

2,5,7,14-tetraacetoxy-3-benzoyloxy-8,15-dihydroxy-9-nicotinoyloxy-jatropha-6(17),11E-diene (jatrophane 5);
2,5,7,9,14-pentaacetoxy-3-benzoyloxy-8,15-dihydroxyjatropha-6(17),11E-diene (jatrophane 6);
20-O-acetyl-ingenol-3-angelate, derivatives of 20-O-acetyl-ingenol-3-angelate.
20-deoxy-ingenol-3-angelate, derivatives of 20-deoxy-ingenol-3-angelate; and
ingenol-3-angelate, derivatives of ingenol-3-angelate.

Reference herein to a subject includes a human, primate, livestock animal (e.g. sheep, cow, horse, pig, goat, donkey), laboratory test animal (e.g. mouse, rat, guinea pig, hamster), companion animal (e.g. dog, cat) or avian species such as poultry birds (e.g. chicken, ducks, turkeys, geese) or game birds (e.g. arid ducks, pheasants).

The preferred subject is a human or primate or laboratory test animal.

The most preferred subject is a human.

The ability to assign numerical values to certain characteristics enables data processing means to assess the likely usefulness of a particular compound or group of compounds forming a chemical agent.

The assessment of the suitability of a compound or group of compounds for the practice of the present invention is suitably facilitated with the assistance of a computer programmed with software, which inter alia adds index values ($I_V$) for at least two features associated with the compound(s) to provide a potency value ($P_A$) corresponding to the effectiveness of the compound(s) for treating or preventing an inflammatory condition or for promoting stimulation of the immune system or components therein. The compound features can be selected from:—
  (a) the ability to modulate PKC activity or effect;
  (b) the ability to induce bipolar dendritic activity;
  (c) the ability to be derived from a member of the Euphorbiaceae family;
  (d) the ability to be derived from E. peplus;
  (e) the ability to be water extractable from the sap of a Euphorbia species;
  (f) the ability to activate latent virus; or
  (g) lower tumor promoting capacity than TPA or PMA.

Accordingly, in accordance with the present invention, index values for such features are stored in a machine-readable storage medium, which is capable of processing the data to provide a potency value for a compound or group of compounds of interest.

Thus, in another aspect, the invention contemplates a computer program product for assessing the likely usefulness of a candidate compound or group of compounds for the treatment or prophylaxis of inflammation or to immunopotentiate a subject, said product comprising:—
(1) code that receives as input index values for at least two features associated with said compound(s), wherein said features are selected from:
  (a) the ability to modulate PKC activity or effect;
  (b) the ability to induce bipolar dendritic activity;
  (c) the ability to be derived from a member of the Euphorbiaceae family;
  (d) the ability to be derived from E. peplus;
  (e) the ability to be water extractable from the sap of a Euphorbia species;
  (f) the ability to activate latent virus; or
  (g) less tumor promoting capacity than TPA or PMA;
(4) code that adds said index values to provide a sum corresponding to a potency value for said compound(s); and
(5) a computer readable medium that stores the codes.

In a preferred embodiment, the computer program product comprises code that assigns an index value for each feature of a compound or group of compounds. In an especially preferred embodiment, index values are assigned as set forth in Table A above.

In a related aspect, the invention extends to a computer for assessing the likely usefulness of a candidate compound or group of compounds for the treatment of inflammation or to immunopotentiate a subject, wherein said computer comprises:—
(1) a machine-readable data storage medium comprising a data storage material encoded with machine-readable data, wherein said machine-readable data comprise index values for at least two features associated with said compound(s), wherein said features are selected from:
  (a) the ability to modulate PKC activity or effect;
  (b) the ability to induce bipolar dendritic activity;
  (c) the ability to be derived from a member of the Euphorbiaceae family;
  (d) the ability to be derived from E. peplus;
  (e) the ability to be water extractable from the sap of a Euphorbia species;
  (f) the ability to activate latent virus; or
  (g) less tumor promoting capacity than TPA or PMA;
(2) a working memory for storing instructions for processing said machine-readable data;
(3) a central-processing unit coupled to said working memory and to said machine-readable data storage medium, for processing said machine readable data to provide a sum of said index values corresponding to a potency value for said compound(s); and
(4) an output hardware coupled to said central processing unit, for receiving said potency value.

Figure 19:
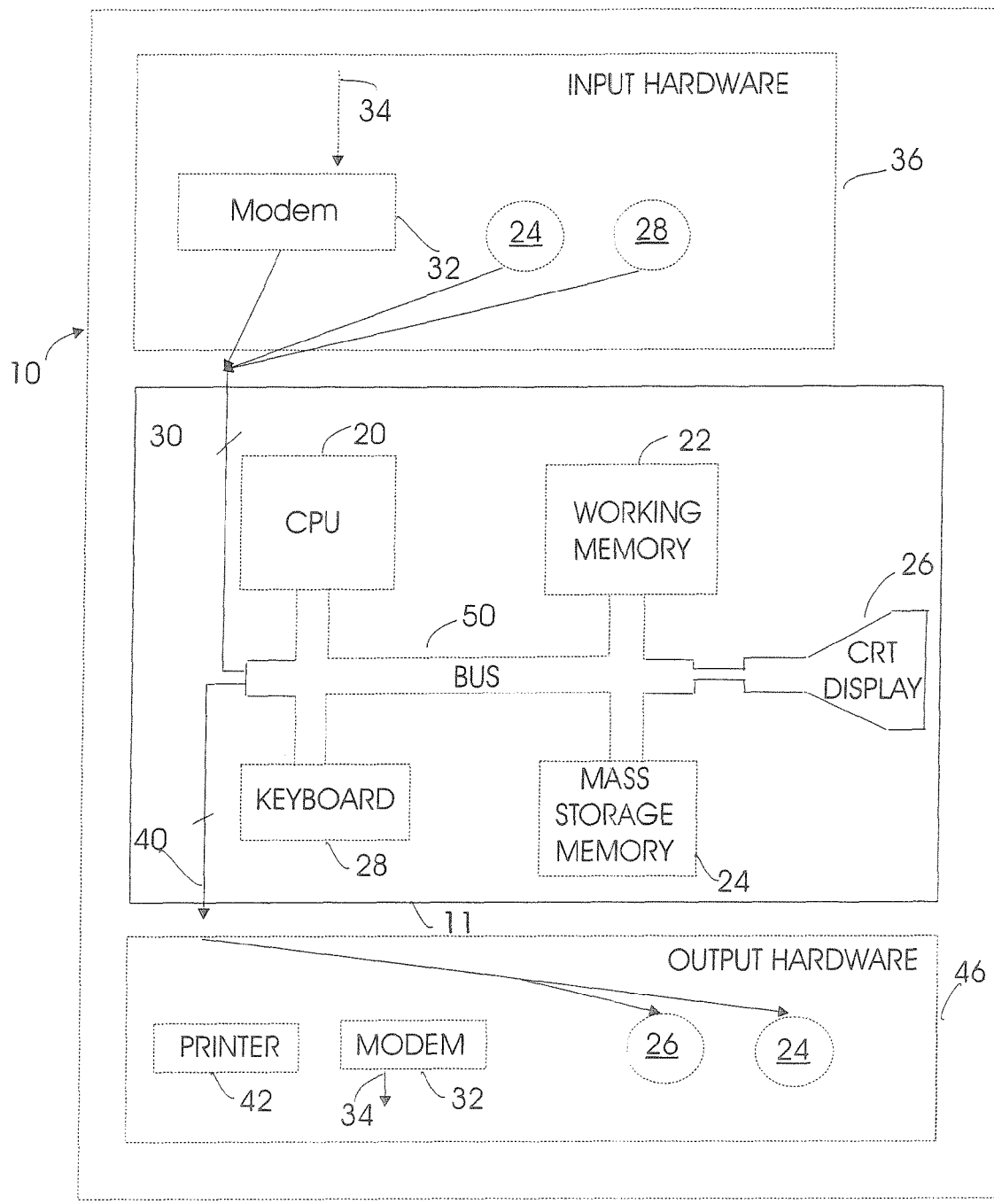
FIG. 19 is a diagrammatic representation of a system used to carry out the instructions encoded by the storage medium of FIGS. 9 and 10.

A version of these embodiments is presented in FIG. 19, which shows a system 10 including a computer 11 comprising a central processing unit ("CPU") 20, a working memory 22 which may be, e.g. RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bidirectional system bus 50.

Input hardware 36, coupled to computer 11 by input lines 30, may be implemented in a variety of ways. For example, machine-readable data of this invention may be inputted via the use of a modem or modems 32 connected by a telephone line or dedicated data line 34. Alternatively or additionally, the input hardware 36 may comprise CD. Alternatively, ROM drives or disk drives 24 in conjunction with display terminal 26, keyboard 28 may also be used as an input device.

Output hardware 46, coupled to computer 11 by output lines 40, may similarly be implemented by conventional devices. By way of example, output hardware 46 may include CRT display terminal 26 for displaying a synthetic polynucleotide sequence or a synthetic polypeptide sequence as described herein. Output hardware might also include a printer 42, so that hard copy output may be produced, or a disk drive 24, to store system output for later use.

In operation, CPU 20 coordinates the use of the various input and output devices 36,46 coordinates data accesses from mass storage 24 and accesses to and from working memory 22, and determines the sequence of data processing steps. A number of programs may be used to process the machine readable data of this invention. Exemplary programs may use for example the following steps:—

(1) inputting input index values for at least two features associated with said compound(s), wherein said features are selected from:—
  (a) the ability to modulate PKC activity or effect;
  (b) the ability to induce bipolar dendritic activity;
  (c) the ability to be derived from a member of the Euphorbiaceae family;
  (d) the ability to be derived from *E. peplus;*
  (e) the ability to be water extractable from the sap of a *Euphorbia* species;
  (f) the ability to activate latent virus;
  (g) less tumor promoting capacity than TPA or PMA; and
(2) adding the index values for said features to provide a potency value for said compound(s); and (3) outputting said potency value.

Figure 20:
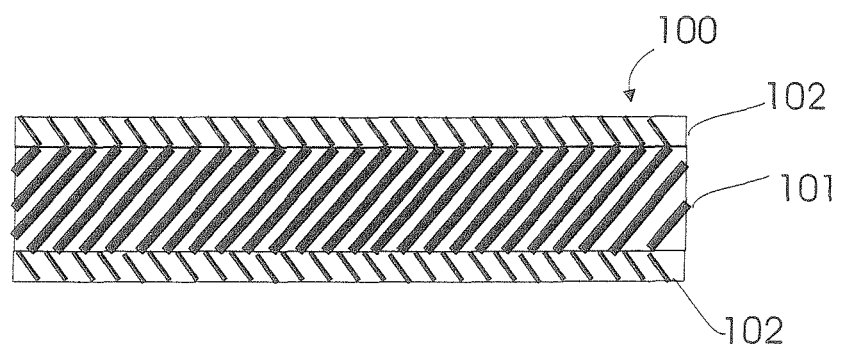
FIG. 20 is a diagrammatic representation of a cross-section of a magnetic storage medium.

FIG. 20 shows a cross section of a magnetic data storage medium 100 which can be encoded with machine readable data, or set of instructions, for designing a synthetic molecule of the invention, which can be carried out by a system such as system 10 of FIG. 10. Medium 100 can be a conventional floppy diskette or hard disk, having a suitable substrate 101, which may be conventional, and a suitable coating 102, which may be conventional, on one or both sides, containing magnetic domains (not visible) whose polarity or orientation can be altered magnetically. Medium 100 may also have an opening (not shown) for receiving the spindle of a disk drive or other data storage device 24. The magnetic domains of coating 102 of medium 100 are polarized or oriented so as to encode in manner which may be conventional, machine readable data such as that described herein, for execution by a system such as system 10 of FIG. 19.

Figure 21:
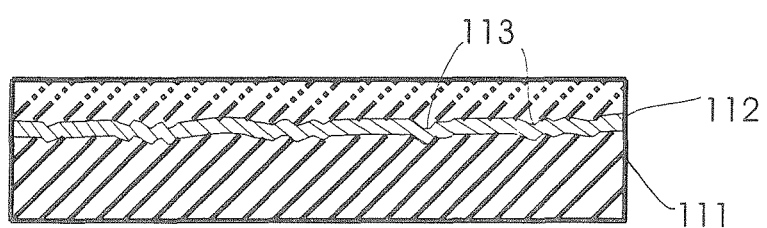
FIG. 21 is a diagrammatic representation of a cross-section of an optically readable data storage system.

FIG. 21 shows a cross section of an optically readable data storage medium 110 which also can be encoded with such a machine-readable data, or set of instructions, for designing a synthetic molecule of the invention, which can be carried out by a system such as system 10 of FIG. 19. Medium 110 can be a conventional compact disk read only memory (CD-ROM) or a rewritable medium such as a magneto-optical disk, which is optically readable and magneto-optically writable. Medium 100 preferably has a suitable substrate 111, which may be conventional, and a suitable coating 112, which may be conventional, usually of one side of substrate 111.

In the case of CD-ROM, as is well known, coating 112 is reflective and is impressed with a plurality of pits 113 to encode the machine-readable data. The arrangement of pits is read by reflecting laser light off the surface of coating 112. A protective coating 114, which preferably is substantially transparent, is provided on top of coating 112.

In the case of a magneto-optical disk, as is well known, coating 112 has no pits 113, but has a plurality of magnetic domains whose polarity or orientation can be changed magnetically when heated above a certain temperature, as by a laser (not shown). The orientation of the domains can be read by measuring the polarization of laser light reflected from coating 112. The arrangement of the domains encodes the data as described above.

The present invention further extends to pharmaceutical compositions useful in treating a pathogenic infection. In this regard, the chemical agents of the invention can be used as actives for the treatment or prophylaxis of a condition associated with the presence of a biological entity or part thereof or toxin or venom therefrom or a genetic event caused thereby in a subject. The chemical agents can be administered to a patient either by themselves, or in pharmaceutical compositions where they are mixed with a suitable pharmaceutically acceptable carrier.

Accordingly, the invention also provides a composition for treatment and/or prophylaxis of an inflammatory condition or to induce immunopotentiation in a subject, comprising one or more chemical agents of the invention, together with a pharmaceutically acceptable carrier and/or diluent.

Depending on the specific conditions being treated, chemical agents may be formulated and administered systemically or locally. Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. For injection, the chemical agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art. Intra-muscular and subcutaneous injection is appropriate, for example, for administration of immunomodulatory compositions and vaccines.

The chemical agents can be formulated readily using pharmaceutically acceptable carriers well known in the art into dosages suitable for oral administration. Such carriers enable the compounds of the invention to be formulated in dosage forms such as tablets, pills, capsules, liquids, gels, syrups, slurries, suspensions and the like, for oral ingestion by a patient to be treated. These carriers may be selected from sugars, starches, cellulose and its derivatives, malt, gelatine, talc, calcium sulphate, vegetable oils, synthetic oils, polyols, alginic acid, phosphate buffered solutions, emulsifiers, isotonic saline, and pyrogen-free water.

Pharmaceutical compositions suitable for use in the present invention include compositions wherein the active ingredients are contained in an effective amount to achieve their intended purpose. The dose of agent administered to a patient should be sufficient to effect a beneficial response in the patient over time such as a reduction in the symptoms associated with the presence of an inflammatory condition in a subject. The quantity of the agent(s) to be administered may depend on the subject to be treated inclusive of the age, sex, weight and general health condition thereof. In this regard, precise amounts of the agent(s) for administration will depend on the judgement of the practitioner. In determining the effective amount of the chemical agent to be administered in the treatment or prophylaxis of a condition associated with the inflammation, the physician may evaluate progression of the disorder. In any event, those of skill in the art may readily determine suitable dosages of the chemical agents of the invention.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as the cross-linked polyvinyl pyrrolidone, agar, or alginic acid or a salt thereof such as sodium alginate. Such compositions may be prepared by any of the methods of pharmacy but all methods include the step of bringing into association one or more chemical agents as described above with the carrier which constitutes one or more necessary ingredients. In general, the pharmaceutical compositions of the present invention may be manufactured in a manner that is itself known, e.g. by means of conventional mixing, dissolving, granulating, dragee-making, levigating, emulsifying, encapsulating, entrapping or lyophilising processes.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Dosage forms of the chemical agents of the invention may also include injecting or implanting controlled releasing devices designed specifically for this purpose or other forms of implants modified to act additionally in this fashion. Controlled release of an agent of the invention may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be effected by using other polymer matrices, liposomes and/or microspheres.

Chemical agents of the invention may be provided as salts with pharmaceutically compatible counterions. Pharmaceutically compatible salts may be formed with many acids, including but not limited to hydrochloric, sulphuric, acetic, lactic, tartaric, malic, succinic, etc. Salts tend to be more soluble in aqueous or other protonic solvents that are the corresponding free base forms.

For any chemical agent used in the method of the invention, the therapeutically effective dose can be estimated initially from cell culture assays such as to reduce inflammation in vitro or to potentiate immune cells in vitro. For example, a dose can be formulated in animal models to achieve a circulating concentration range that includes the IC50 as determined in cell culture (e.g. the concentration of a test agent, which achieves a half-maximal inhibition of inflammation). Such information can be used to more accurately determine useful doses in humans.

Toxicity and therapeutic efficacy of such chemical agents can be determined by standard pharmaceutical procedures in cell cultures or experimental animals, e.g. for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. The data obtained from these cell culture assays and animal studies can be used in formulating a range of dosages for use in humans. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition (see for example Fingl et al., 1975, in "The Pharmacological Basis of Therapeutics", Ch. 1 p1).

Dosage amount and interval may be adjusted individually to provide plasma levels of the active agent which are sufficient to maintain symptom-ameliorating effects. Usual patient dosages for systemic administration range from 1-2000 mg/day, commonly from 1-250 mg/day, and typically from 10-150 mg/day. Stated in terms of patient body weight, usual dosages range from 0.02-25 mg/kg/day, commonly from 0.02-3 mg/kg/day, typically from 0.2-1.5 mg/kg/day. Stated in terms of patient body surface areas, usual dosages range from 0.5-1200 mg/m$^2$/day, commonly from 0.5-150 mg/m$^2$/day, typically from 5-100 mg/m$^2$/day.

Alternately, one may administer the compound in a local rather than systemic manner, for example, via injection of the compound directly into a tissue, often in a depot or sustained release formulation. Furthermore, one may administer the drug in a targeted drug delivery system, for example, in a liposome coated with tissue-specific antibody. The liposomes will be targeted to and taken up selectively by the tissue. In cases of local administration or selective uptake, the effective local concentration of the agent may not be related to plasma concentration.

The chemical agents of the invention can also be delivered topically. For topical administration, a composition containing between 0.001-5% or more chemical agent is generally suitable. Regions for topical administration include the skin surface and also mucous membrane tissues of the vagina, rectum, nose, mouth, and throat. Compositions for topical administration via the skin and mucous membranes should not give rise to signs of irritation, such as swelling or redness.

The topical composition may include a pharmaceutically acceptable carrier adapted for topical administration. Thus, the composition may take the form of a suspension, solution, ointment, lotion, sexual lubricant, cream, foam, aerosol, spray, suppository, implant, inhalant, tablet, capsule, dry powder, syrup, balm or lozenge, for example. Methods for preparing such compositions are well known in the pharmaceutical industry.

In one embodiment, the topical composition is administered topically to a subject, e.g. by the direct laying on or spreading of the composition on the epidermal or epithelial tissue of the subject, or transdermally via a "patch". Such compositions include, for example, lotions, creams, solutions, gels and solids. Suitable carriers for topical administration preferably remain in place on the skin as a continuous film, and resist being removed by perspiration or immersion in water. Generally, the carrier is organic in nature and capable of having dispersed or dissolved therein a chemical agent of the invention. The carrier may include pharmaceutically-acceptable emolients, emulsifiers, thickening agents, solvents and the like.

The invention also features a process for separating macrocyclic diterpenes from a biomass containing same, said process comprising contacting the biomass with an aqueous solvent for a time and under conditions sufficient to extract the macrocyclic diterpenes into said solvent.

The aqueous solvent is preferably water.

Suitably, the biomass is derived from a plant, which is preferably a member of the Euphorbiaceae family of plants or botanical or horticultural relatives of such plants. Matter from the plant (e.g. foliage, stems, roots, seeds, bark, etc.) is preferably cut, macerated or mulched to increase the surface area of the plant matter for aqueous extraction of the macrocyclic diterpenes.

The process preferably further comprises adsorbing the macrocyclic diterpenes to a non-ionic adsorbent, which is suitably a non-ionic porous synthetic adsorbent. Among the non-ionic porous synthetic adsorbents that can be used for the purposes of the present invention include, but are not restricted to, aromatic copolymers mainly composed of styrene and divinylbenzene, and methacrylic copolymers mainly composed of monomethacrylate and dimethacrylate. Such non-ionic porous synthetic adsorbents which comprise, as the basic structure, aromatic copolymers mainly composed of styrene and divinylbenzene include, for example, Diaion HP10, HP20, HP21, HP30, HP40, HP50, SP850, and SP205 (trade names: Mitsubishi Chemical Corp.), and Amberlite XAD-2, XAD4, (trade names: Rohm and Haas Co.). Examples of non-ionic porous synthetic adsorbent which comprise, as the basic structure, methacrylic copolymer mainly composed of monomethacrylate and dimethacrylate are Diaion HP2MG, Amberlite XAD-7, XAD-8 and XAD-16 and others.

Preferably, the process further comprises eluting macrocyclic diterpenes from the non-ionic adsorbent with water and water-soluble organic solvent(s).

The treatment may be conducted by a batch method using water and water-soluble organic solvent(s) which dissolve macrocyclic diterpenes, or may also be conducted continuously or in batch using a column chromatography method.

Examples of a water-soluble organic solvent which may be used in the present invention are alcohols such as methanol, ethanol, n-propyl alcohol, isopropyl alcohol, and tert-butanol, ethers such as dioxane and tetrahydrofuran, ketones such as acetone, amides such as dimethylformamide, sulfur-containing compounds such as dimethylsulfoxide. Two or more of such organic solvents may be mixed for use. In addition, solvents less soluble in water, for example, alcohols such as n-butanol, esters such as methyl formate and methyl acetate, and ketones such as methyl ethyl ketone may also be used to the extent that it does not separate during development. Particularly preferred water-soluble organic solvents are alcohols, in particular, methanol, ethanol, propyl alcohol, and the like. Furthermore, different kinds of solvent may also be used sequentially for development.

Macrocyclic diterpenes can be further purified using media and techniques which separate compounds on the basis of molecular size and/or polarity. In a preferred embodiment of this type, the macrocyclic diterpenes are separated using Sephadex HL-20 resin and preferably using water and water-soluble organic solvent(s) for development.

The present invention is further described by the following non-limiting Examples.

EXAMPLE 1

PKC Activation: Kinase Activity of PKC as Measured by Enzyme Assay

Preparation of Chemical Fractions from E. Peplus

Sap from *E. peplus* plants was collected, stored at −20° C., thawed and stored at 4° C. for 1 week prior to use. The H fraction was prepared from frozen sap by thin layer chromatography (TLC) as described in International Patent Application No. PCT/AU98/00656 and was stored as dried silica-associated material at 4° C. This material was enriched in jatrophanes and pepluanes. One to two months prior to use, the material was dissolved in ethylene glycol dimethyl ether (DME) and stored at 4° C. The concentrations were determined from the dry weight of the material. For PKC assays, crude sap (PEP001) and the PEP004 fraction was ether extracted twice to produce an ether-soluble fraction enriched in diterpenes, namely, ingenanes, jatrophanes and pepluanes. The remaining water soluble fraction was also used. An ingenane fraction was prepared from the ether-soluble extract by TLC as described in International Patent Application No. PCT/AU98/00656, which corresponds to U.S. Pat. No. 6,432,452, the contents of which are incorporated by reference.

PKC Assay

The conventional and novel protein kinase C (PKC) isoforms, in their unstimulated state, are inactive as kinases. The C1 domain of these PKCs contains an autoinhibitory, pseudosubstrate site that binds to the substrate site (C4 domain) and inactivates the kinase functionality of the protein. Activation of PKC results from binding of diacylglycerol (DAG) to the C1 domain, which, via multiple phosphorylation events and conformational changes to the protein, ultimately leads to the release of PKC autoinhibition. TPA and other related compounds have been shown to bind to the C1 domain of various PKC isoforms and presumably by similar means as DAG, lead to their activation.

The kinase activity of rat brain PKC (Promega) was determined using the Peptag™ Non-Radioactive Protein Kinase Kit (Promega). Using agarose gel electrophoresis the technique visualises the opposing electrostatic charge of a fluorescently labeled peptide (PLSRTLSVAAK) compared to the phosphorylated version of the same peptide.

The results of an assay of PKC with the fluorescent substrate (PepTag) are shown in FIG. 1. The reaction mixture was separated by gel electrophoresis, showing migration of the unreacted substrate (a) to the anode (top), and the product (b), which is more negatively charged because of phosphorylation by PKC, moving towards the cathode (bottom). The positive control activator (phosphatidyl serine) supplied by the manufacturer (lane 2) showed strong activation compared with PKC and substrate alone (lane 1). Various dilutions of TPA also showed activation of PKC (lanes 3, 4 and 5).

An ether extract of *E. peplus* sap, reconstituted in dimethoxyethane (DME) and incubated with PKC at a final dilution of 1 in 5 relative to the sap, gave a significant level of action (lane 7), as did the crude sap itself (lane 9). In the latter case, however, both the substrate and product (band c, lane 9) were found further towards the cathode. This result was interpreted as being due to a carboxypeptidase activity in the crude sap, cleaving the C-terminal, positively-charged lysine from the substrate peptide. This was confirmed by the finding that the aqueous layer from ether extraction had minimal PKC-activating ability, but altered migration of the substrate in the same way as the crude sap (lane 8). DME itself had no activity (lane 10).

Figure 2:
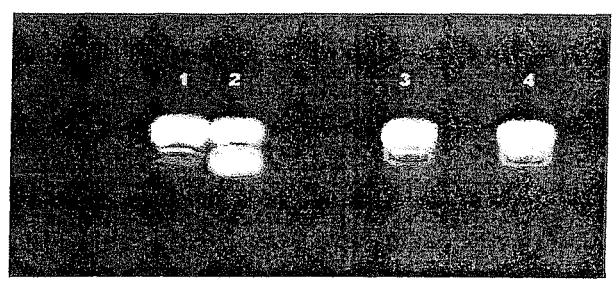
FIG. 2 shows the activation of PKC by *E. peplus* fractions. Lanes 1 and 2, same as FIG. 1; lane 3, 2 mg/ml fraction H; lane 4, 2 mg/ml ingenanes.

FIG. 2 shows the results of testing fractionated materials simultaneously with negative (lane 1) and positive controls (lane 2). Fraction H (mixture of jatrophanes and pepluanes) showed a low activity (lane 3), seen as a halo of product (arrow) moving away from the unreacted substrate. A similar result was found for the ingenane fraction (lane 4).

All of the *E. peplus* fractions are tested for activation of all the available protein kinase enzymes using the peptide-based fluorescent tag test described above. The isoenzymes available for this experiment (Panevera) were $\alpha$, $\beta 1$, $\beta 11$, $\gamma$, $\delta$, $\epsilon$, $\eta$ and $\zeta$.

Figure 3:
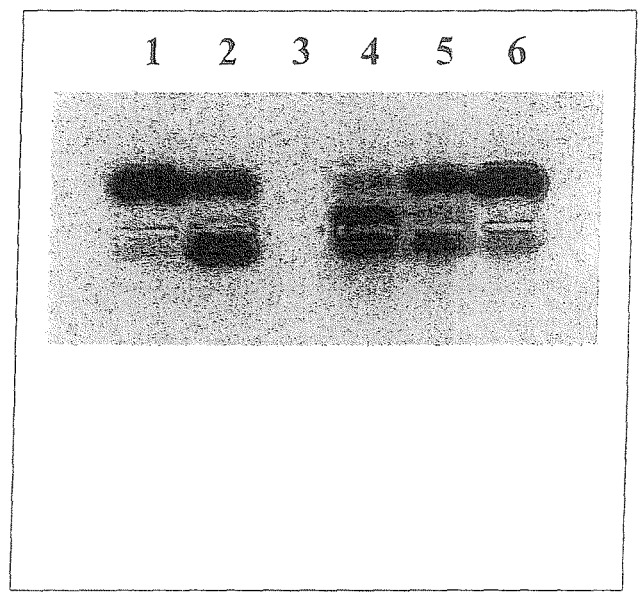
FIG. 3 is photographic representation showing the results of a PKC assay using rat brain PKC. Lane 1, negative control; lane 2, positive control; lane 3, empty; lane 4, PEP001 (1/125 dilution), lane 5, PEP001 (1/500 dilution) and lane 6, TPA (20 µg).

Essentially, the kinase activity of the PKC sample was assessed before stimulation (Negative Control) and after stimulation with PEP001, phosphatidyl serine (an acid-lipid, known to activate PKC, provided by Promega; Positive Control) and TPA (20 µg/mL). The results presented in FIG. 3 indicate that PEP001, at dilutions of 1:125 and 1:500, activates PKC to a similar level as phosphatidyl serine (200 µg/mL) and to a greater level than TPA (20 µg/mL). From this experiment, it is clear that the PEP001 activates PKC.

EXAMPLE 2

PKC Activation: Translocation of PKC

Activation of PKC can also be demonstrated by a simple fluorescence microscopy-based assay. Upon activation, PKC is known to translocate from the cytoplasm to the plasma membrane of the cell. By fusing PKC enzymes to the green fluorescent protein (GFP) or enhanced GFP (EGFP), activation of the PKC can be detected by the movement of diffuse cytoplasmic GFP to a ring of fluorescence associated with the plasma membrane. Using this assay, crude *E. peplus* extract has been shown to activate PKCβ and PKCγ.

Figure 4A:
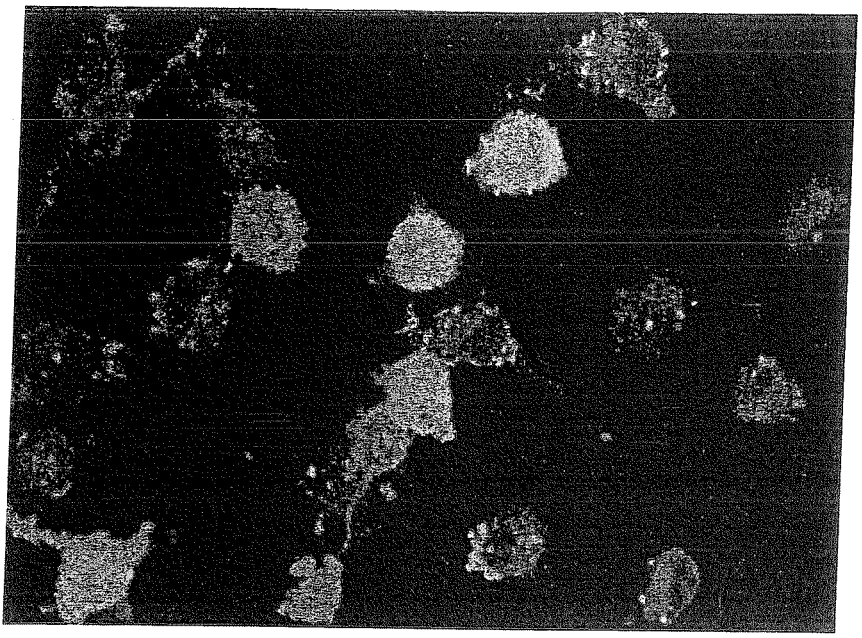
FIG. 4 is a photographic representation showing the activation of PKC in MM96L cells expressing PKC fused to green fluorescent protein (GFP). (A) PKCβ expressed in the nuclei of MM96L human melanoma PKC MM96L cells in the absence of drug. (B) After treatment with crude *E. peplus* extract for 2 hr.
Figure 4B:

MM96L cells were first transfected using a commercially-available kit (Qiagen Effectine Transfection Kit) with a PKC-GFP expression vector (Clontech; http://www.clontech.com/gfp/) and allowed to produce the PKC-GFP protein for 24 hr. The cells were then treated with crude *E. peplus* extract and TPA and observed under a fluorescent microscope (488 nm excitation). Two controls were used—no DNA, which allows for the identification of non-transfected cells, and no drugs, which allows for the calculation of transfection efficiency and the identification of transfected cells without PKC activation. pPKCβ-EGFP and pPKCγ-EGFP were tested, and crude *E. peplus* extract was shown to induce movement of the fluorescence from the cytosol to the plasma membrane, indicating that crude *E. peplus* extract activated these PKC enzymes. The results are illustrated in FIGS. 4A and 4B, which respectively show expression of PKCβ in the absence of any drug and after exposure to crude *E. peplus* extract for 2 hr.

In another experiment, translocation of individual PKC isoforms was observed using fluorescence microscopy and used as an indication of activation by PEP003 and PEP005.

Five EGFP-PKC isoforms (Clontech) were available for this experiment, enabling the screening of the three predominant PKC families (i.e. classical, novel and atypical PKCs). The members of the various PKC families are $\alpha$, $\beta$, and $\gamma$ (classical), $\theta$ (novel) and $\zeta$ (atypical).

Figure 5:
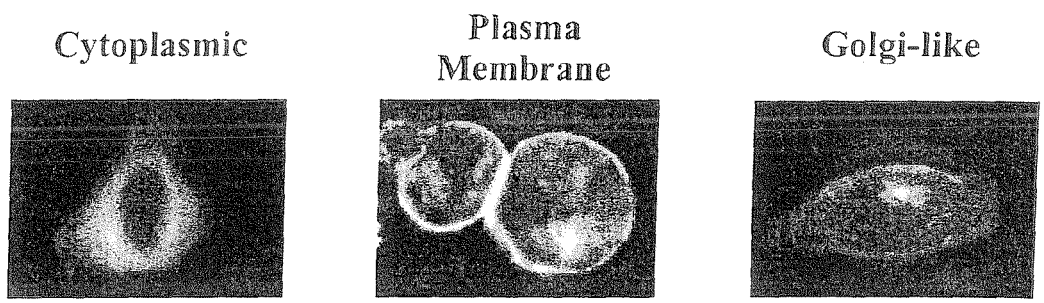
FIG. 5 is a photographic representation showing induction of translocation of activated PKCs by the compounds of the instant invention to the cytoplasm, plasma membrane and to the Golgi or similarly located cellular structure.

HeLa cells were plated out in a 24-well plate containing coverslips and transfected with PKC isoforms fused to EGFP, using a commercially available effectine-transfection kit (QIAGEN, Pty. Ltd.). Cells were exposed to the transfection reagents for 16-24 hr. Subsequently, transfected cells were treated for one hour with TPA (100 ng/mL), bryostatin-1 (5 pg/mL), PEP003 (2.25 µg/mL; 5 µM) or PEP005 (670 µg/mL) 1.5 µM). Following treatment, cells were fixed on coverslips and mounted on glass slides. The slides were subsequently examined visually by fluorescence microscopy, photographed, and over 150 cells were counted/treatment/PKC isoform. Counted cells were classified according to the localisation of the PKC-EGFP fluorescence as either cytoplasmic or plasma membrane using ImagePro™ 4.1 (FIG. 5). Several cells also showed localisation to the Golgi, or similarly located cellular structure (FIG. 5). The number of these cells was also counted. Results are presented as an average and standard deviation of percentages of cells (Table 1).

Figure 6:
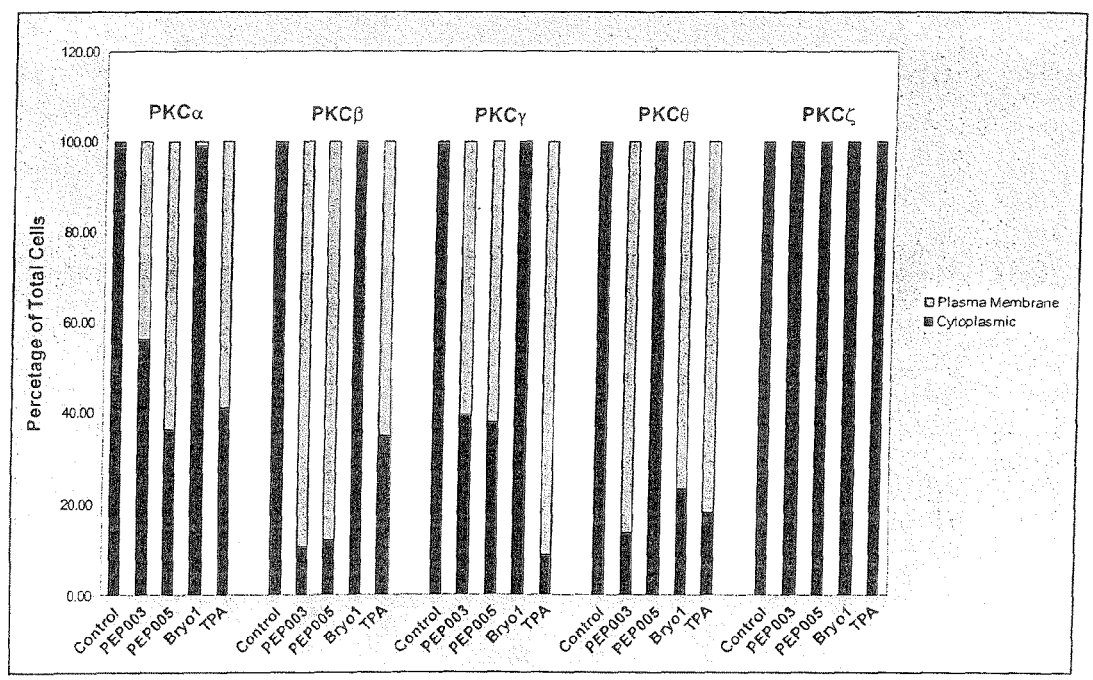
FIG. 6 is a graphical representation showing the induction of translation of the classical and novel PKC isoforms in response to PEP003, PEP005, bryostatin-1 and TPA.

The results presented in FIG. 6 show that PKC $\alpha$, $\beta$ and $\gamma$ are translocated from the cytoplasm to the plasma membrane in response to treatment with PEP003, PEP005 and TPA but not with bryostatin-1. As expected, the diacylglycerol-independent PKCζ is not translocated in response to any treatment. PKCθ is translocated in response to PEP003, TPA and bryostatin-1, however, PEP005 does not induce any change in the isoenzymes localization. The results also show that treatment of PKCα and γ transfected cells with TPA, PEP003 and PEP005 leads to an increase in the number of cells displaying Golgi-like fluorescence. PKCβ transfected HeLa cells treated with TPA also show an increase in Golgi-like fluorescence. In contrast, treatment with PEP005 and bryostatin-1 decreases the number of cells with PKCβ concentrated in the Golgi. The number of PKC transfected HeLa cells with Golgi-like localization is increased in response to all treatments.

The above results indicate that PEP003 and PEP005 induce translocation of the classical and novel PKC isoforms tested, suggesting that these compounds activate members of the classical and novel PKC families. TPA, Bryostatin-1, PEP003 and PEP005 fail to induce translocation of PKCζ, suggesting that PEP003 and PEP005 do not activate members of the atypical PKC family. Furthermore, TPA, Bryostatin-1, PEP003 and PEP005 display differences in their ability to induce translocation of the specific PKC isoforms to the plasma membrane and/or Golgi. These differences may play a role in determining the different biological actions of these compounds.

EXAMPLE 3

Binding of Compounds to PKC

A competition assay was performed to determine whether the diterpene esters of the instant invention bind to the phorbol ester binding site of PKC. This competition assay showed that 23 µg/mL PEP003 displaced >90% [3H]-phorbol dibutyrate from binding to rat brain homogenate, used as a source of PKC (Gonzalez et al., 1999). This binding was not blocked by co-incubation with bisindolylmaleimide. These results show that PEP003 binds to the phorbol ester binding site of PKC, and bisindolylmaleimide does not.

EXAMPLE 4

Activation of Latent HIV Infection

The use of highly active anti-retroviral therapy such as combinations of reverse transcriptase inhibitors and protease inhibitors (HAART) has significantly prolonged the life of individuals infected with HIV. However, the regimen is very burdensome, requiring strict adherence to prevent a recurrence of viraemia. Long-lived cells capable of actively transcribing virus, such as CD4[+] cells, act as a major latent reservoir and enable the virus to avoid anti-retroviral chemotherapy or immune system surveillance. There is, therefore, an urgent need to find an agent which activates latent virus from the infected cells. Activated virus could then be killed by aggressive anti-retroviral chemotherapy and it has been hypothesized that immune system surveillance could also be improved under these conditions. Such an agent could have utility in other disease states in which virus is sequestered in infected cells, e.g. herpes infections. Anti-cancer agents have been widely investigated as potential anti-HIV agents. Several PKC activators have been shown to activate latent retroviruses. For example, PMA has been shown to activate latent HIV in monocytes (Tobiume et al., 1998). However, PMA is a known tumor promoter.

A latently HIV-1 infected cell line (U1), derived from the promonocytic cell line U937 after infection with HIV-1 LAI strain, was used in these experiments. In the absence of activation, no or little virus (measured as p24 production) is produced by the U1 cell line. Phorbol esters are known to activate virus production from these cells (Tobiume et al., 1998) and so TPA/PMA was used as a positive control in these experiments.

U1 cells were cultured in RPM1-1640 medium supplemented with 10% fetal bovine serum, $10^5$ cells/mL were cultured for 20 hr in the presence and absence of various concentrations of either the phorbol ester TPA or crude $E.$ $peplus$ sap (PEP001) or PEP004 (H1) derived therefrom. Supernatants were collected and viral replication monitored by determination of the amounts of HIV p24 gag protein in the culture supernatants by ELISA, using a NEN Life Science HIV-1 p24 ELISA kit. p24 values were calculated from OD values using a standard curve.

Figure 7:
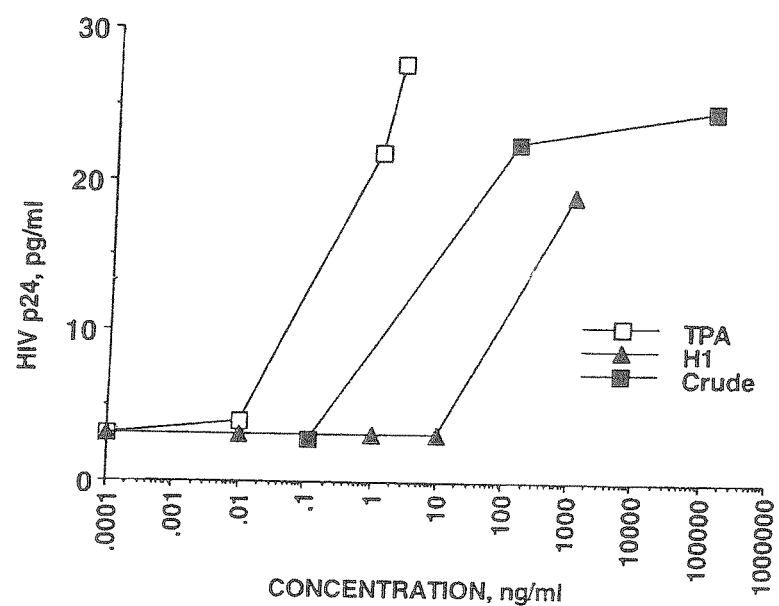
FIG. 7 is a graphical representation showing the activation of HIV from U1 cells.
Figure 8A:
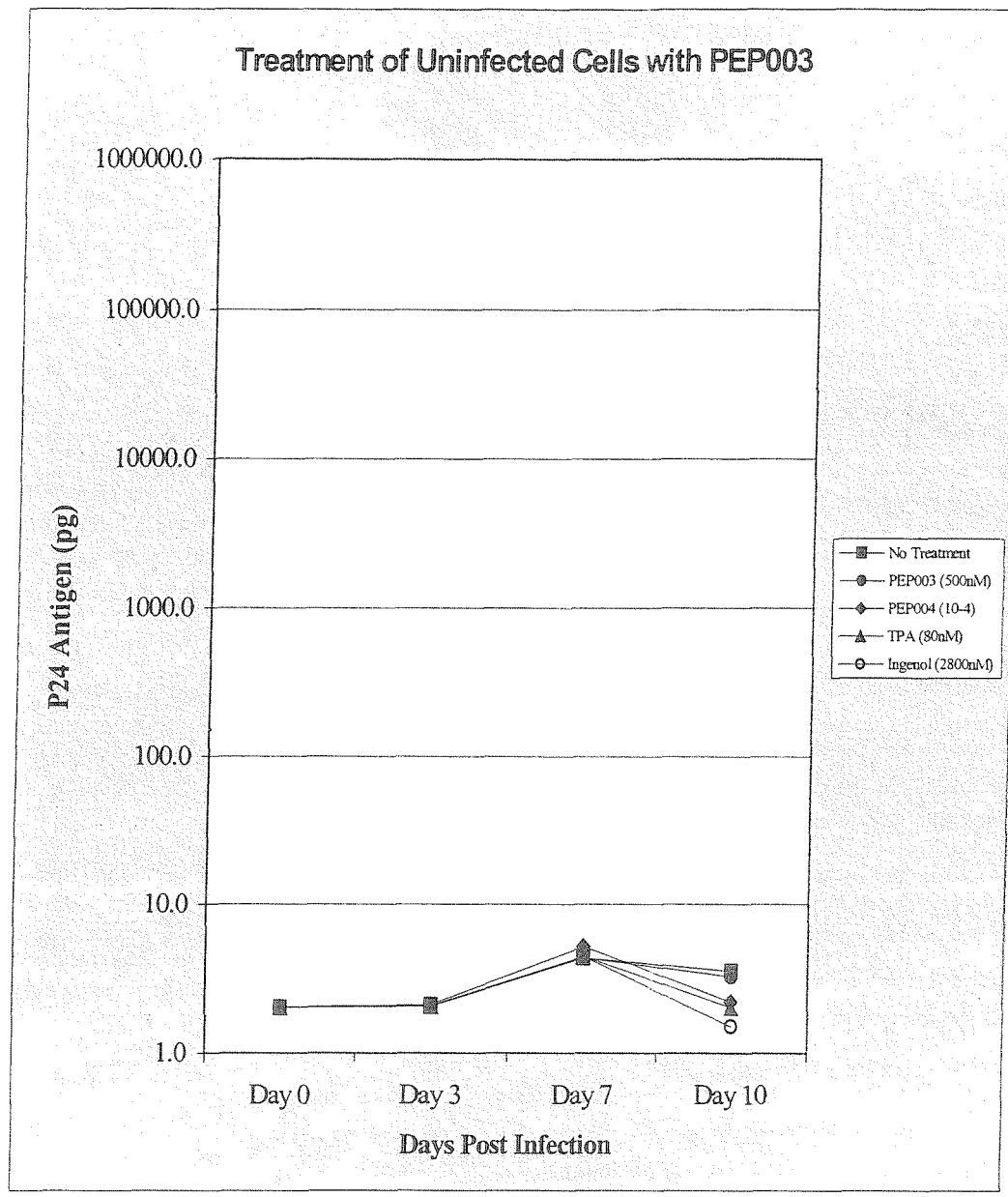
FIG. 8 is a graphical representation showing treatment of lytic HIV infection of peripheral blood mononuclear cells (PBMC) with PEP003, PEP004, TPA and ingenol, expressed as p24 production over a 10 day treatment period. (A) Uninfected cells, (B) low titer infected cells, (C) low titer infected cells represented as p24 production versus drug concentration, (D) same as (C) but high titer infection.
Figure 8B:
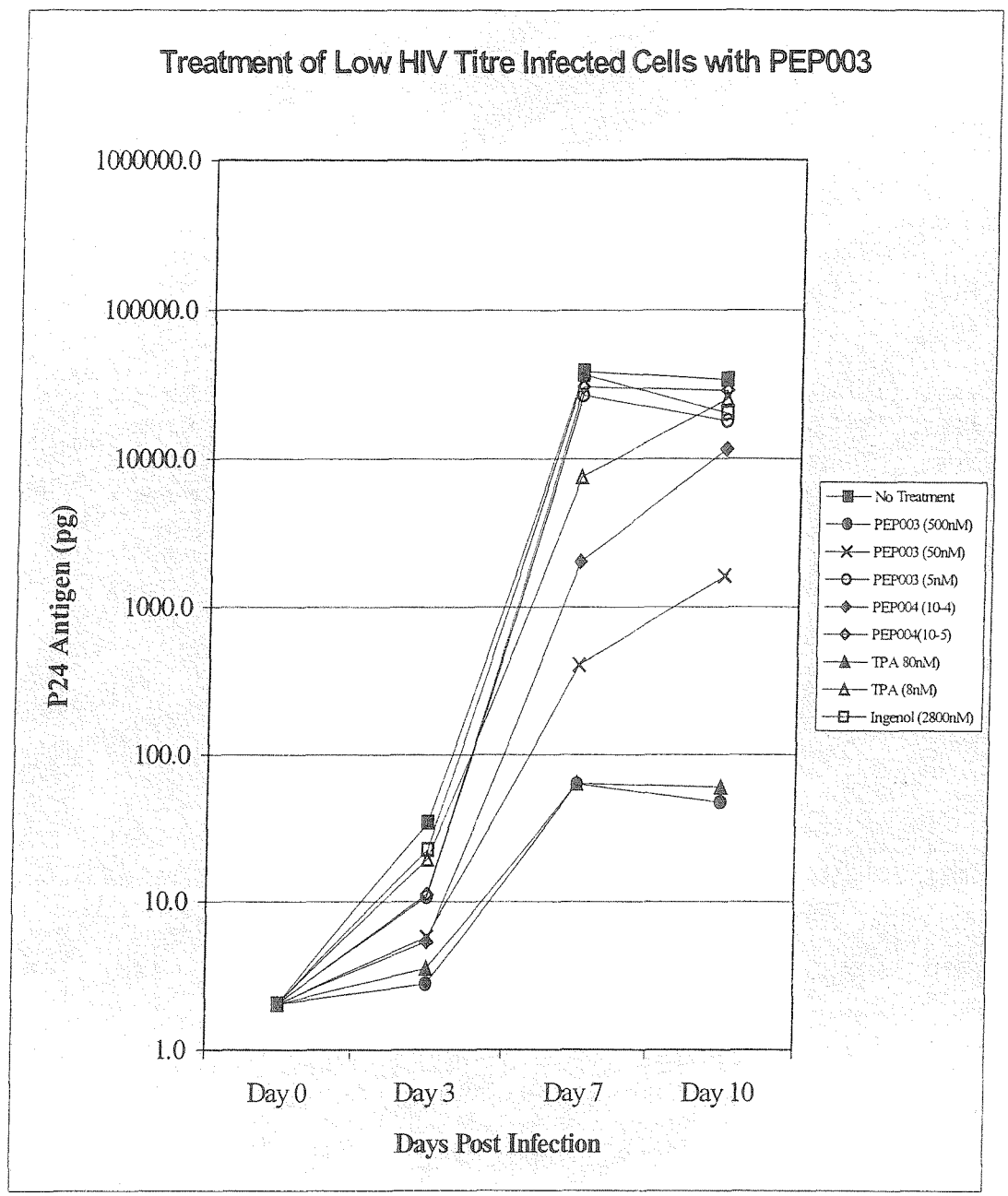
Figure 8C:
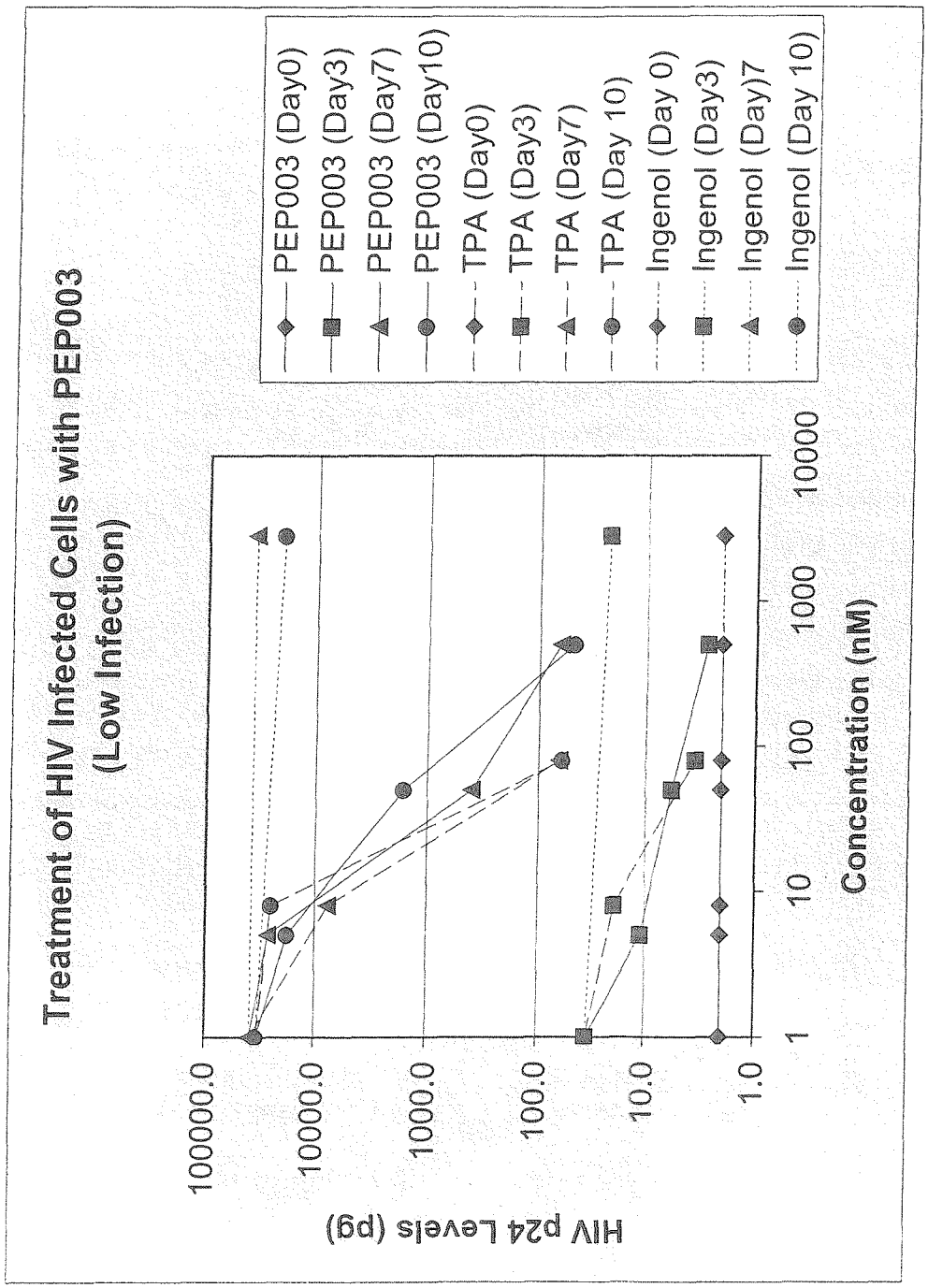
Figure 8D:
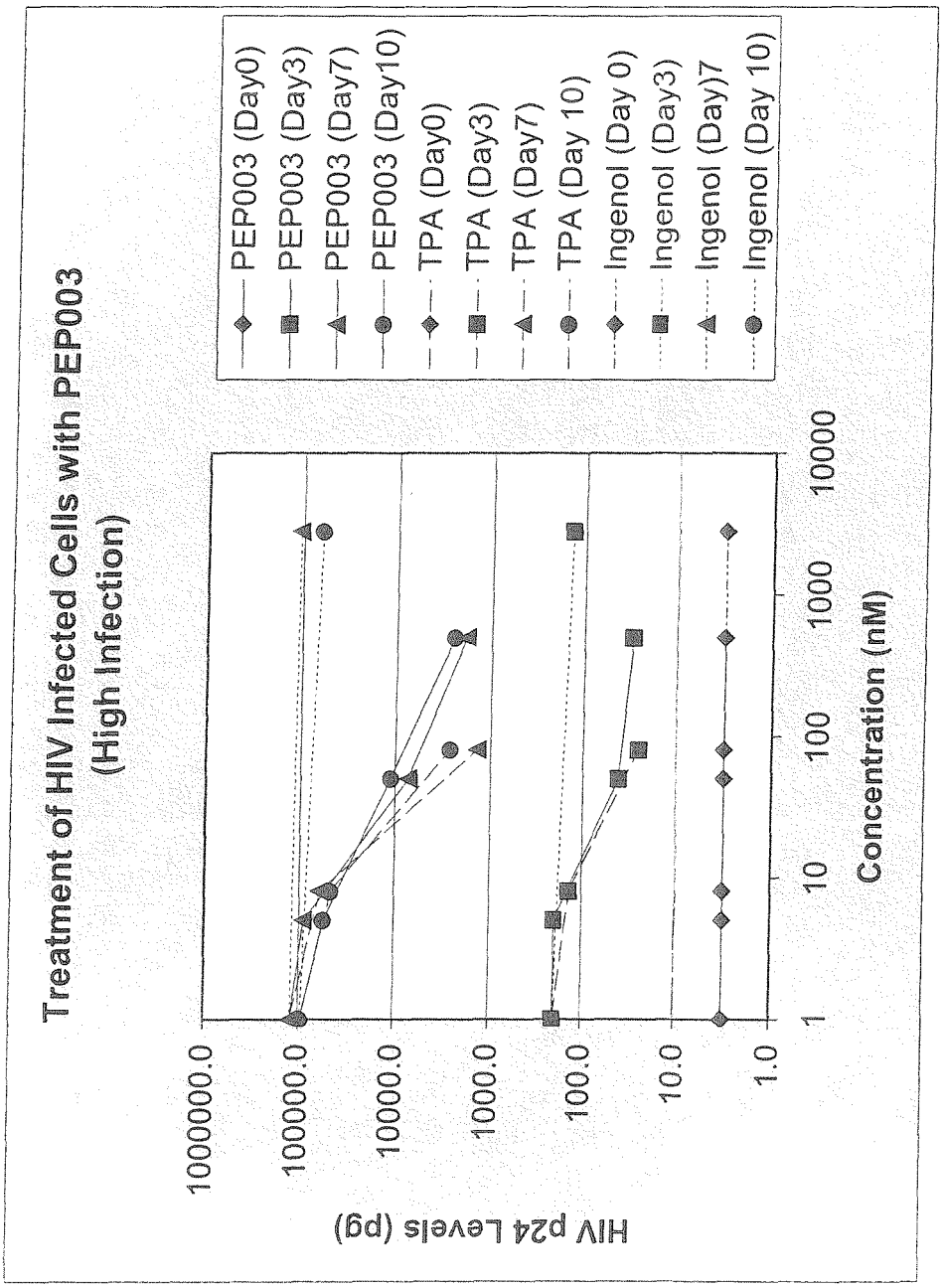

TPA, the crude sap (PEP001) from $E.$ $peplus$ and the PEP004 fraction all activated HIV from U1 cells, as illustrated in FIG. 7. The crude sap (PEP001) was 50 times less active than TPA. The PEP004 fraction was 1000 times less active than TPA.

EXAMPLE 5

Lytic HIV Activity Inhibited by PEP003 and PEP004

The human immunodeficiency virus (HIV), a retrovirus, is the cause of the fourth greatest killing disease in the world, infecting more than 36 million people. A number of anti-retroviral compounds have been approved for clinical use, but many HIV strains have developed resistance to these drugs. There is clear and immediate need for new anti-retroviral compounds.

Experiments were conducted to assess the effect of the compounds of the instant invention on HIV-1 replication in acutely infected T cells. Peripheral blood mononuclear cells (PBMC) were obtained from non-HIV-1, non-HIV-2, non-Hepatitis B/C infected donors, stimulated with phytohemagglutinin-M and grown in culture media supplemented with 10 U/mL interleukin-2. The activated PBMC were infected with 10 g (Low Titre) and 100 ng (High Titre) of CA-p24 equivalents of the HIV-strain pNL4-3. Cells were infected for two hr after which, the virus was removed and the cells were washed with culture media. Equivalent numbers of cells were seeded into 24 well plates and compounds were added to the cultured cells that included: TPA at 8 nM and 80 nM, Ingenol at 280 nM, PEP003 at 500 nM, 50 nM and 5 nM, or PEP004 at dilutions of $1\times10^4$ and $1\times10^5$ from the stock (final concentrations). In addition, uninfected activated PBMC were grown in the presence of TPA (80 nM), Ingenol (280 nM), PEP003 (500 nM) and PEP004 ($1\times10^4$ dilution). Other cultures were neither infected nor treated with any compound, or infected but not treated with any compound. Supernatant was removed from each culture at day 0, 3, 7, and 10. The amount of HIV-1 CA-p24 was determined using a commercially available ELISA assay. Three independent experiments were performed.

The data presented in FIGS. 8A-8D show that PEP003 reduced virus replication kinetics in a dose-dependent manner. PEP003 at concentrations of 500 nM, 50 nM and 5 nM reduced the replication rate by approximately 99.9%, 95% and 47%, respectively, relative to the untreated, infected cells. PEP004 at dilutions of $1\times10^4$ and $1\times10^5$ reduced the replication rate by approximately 66% and 15%, respectively. Viral load seemed to alter these results slightly, as higher initial inoculums of virus reduced the total inhibition of PEP003 at 500 nM or 50 nM to approximately 97% (t-test; p<0.001) or 88% (t-test; p<0.074), respectively. The control compounds Ingenol (2.8 nM) and TPA (80 nM or 8 nM) reduced HIV-1 replication rates by approximately 35%, 98% and 38%, respectively.

EXAMPLE 6

Enhancement of the Cytomegalovirus Promoter Activity as a Method for Improving Gene Therapy Viruses and viral promoters especially adenovirus and CMV are used to deliver gene therapy in a range of human disease conditions. Gene expression and, hence, therapeutic effect will be enhanced if the promoters driving their transcription can be activated further by an agent.

Human melanoma cells were infected with ten-fold dilutions of adenovirus 5 in culture, treated with dilutions of PEP005, PEP006, PEP008 and PEP010 and adenovirus replication determined 2 days later by immunhistochemical detection of virus-replicating cells. Virus replication (enumerated as the number of stained cells following successive incubations with adenovirus antibody, peroxidase-conjugated protein A and peroxidase substrate) was increased by 344% with 67 ng/mL PEP005, 256% with 295 ng/mL PEP006, 248% with 226 ng/mL PEP008 and 147% with 67.5 ng/mL PEP010.

The CMV promoter is commonly used to activate the transcription of genes in constructs transfected into a variety of cells, due to its strong transcriptional activity in a variety of human cell types. The ability of TPA to increase this activity has been demonstrated in cells undergoing non-productive infection with an adenovirus construct (Christenson et al., 1999), thus raising the possibility of increasing the production of a therapeutic protein encoded by a similar construct.

Human melanoma cells (MM96L; 50,000 per microtiter well) were treated with TPA or dilutions of crude $E.$ $peplus$ sap, infected with a 1/20 dilution of a pool of adenovirus-5 expressing β-galactosidase driven by the CMV promoter. After incubation for 20 hr, the wells were washed with 3× with PBS, 50 μL of chlorophenol red galactoside (GPRG) substrate solution added and the absorbance at 540 nm read after 90 min. The inventors found TPA (100 ng/mL) and crude $E.$ $peplus$ sap (diluted 1 in 10,000) both induced the CMV promoter activity by >3-fold.

EXAMPLE 7

Activation of Innate Immune Responses: Induction of Neutrophil Invasion in Skin

Neutrophils represent about 70% of peripheral white blood cells in humans and play a pivotal role in inflammation and the innate defense against disease (Mollinedo, 1999). Upon activation, neutrophils release superoxide radicals and granules containing a variety of enzymes and other compounds. These secretions are able to destroy invading pathogens, but also result in inflammation and associated tissue damage.

Figure 9A:
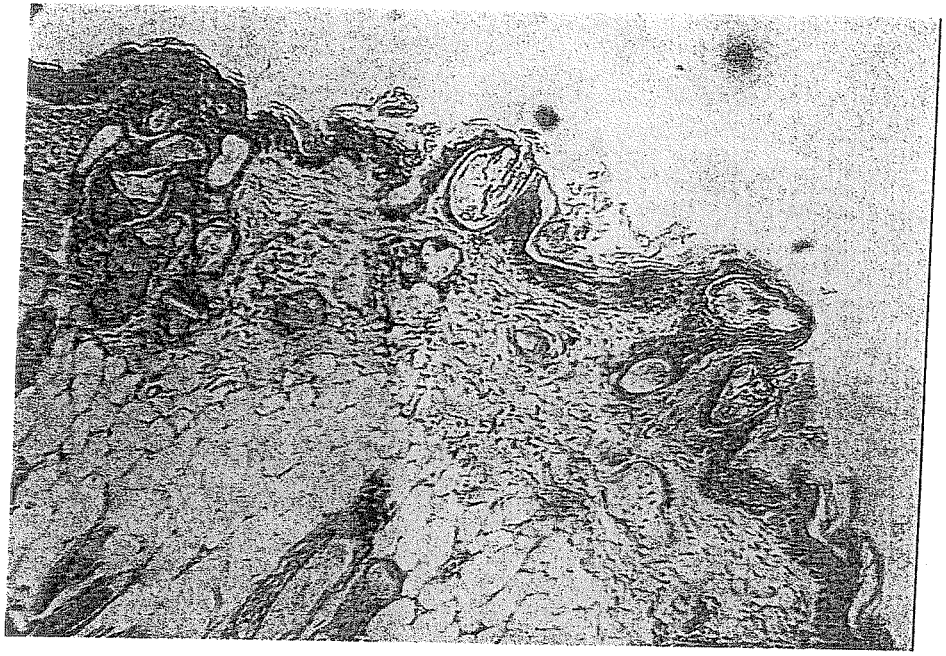
FIG. 9 is a photographic representation showing the recruitment of neutrophils in the skin induced by PEP001 extract. (A) Normal skin of nude mouse. (B) Skin of nude mouse showing infiltration of neutrophils one day after treatment with *E. peplus* sap.
Figure 9B:
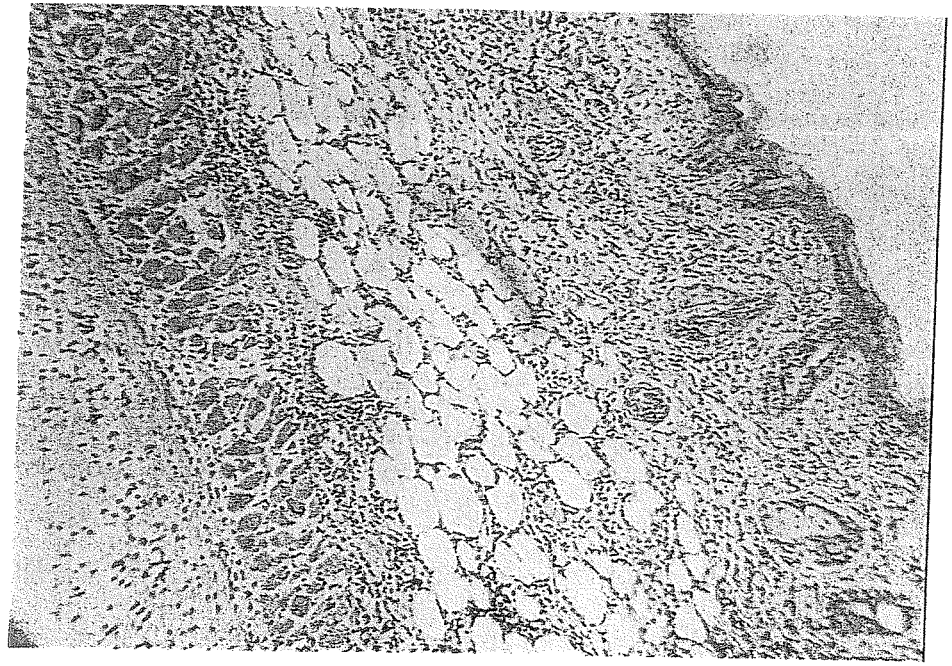

The inventors found that *E. peplus* sap causes accumulation of neutrophils at the site of application, showing that *E. peplus* sap is capable of recruiting neutrophils. A mixture of active diterpenes obtained as an ether extract from *E. peplus* sap was applied (2 μL of 100 mg/mL in ethanol) on the skin of a nu/nu mouse. After 24 hr, the animal was sacrificed and the skin fixed in 10% formalin for sectioning and hematoxylin/eosin staining. As shown in FIGS. 9A and 9B, control skin showed normal skin structure with few infiltrating monocytes. The treated skin showed large numbers of infiltrating neutrophils, characterized by their polymorphic nuclei. There was no evidence of gross damage to the skin.

EXAMPLE 8

Neutrophil Infiltration Activity

Basal cell carcinoma (BCC) is the most common cancer in the Caucasian population, with the highest annual incidence globally having been recorded in Australia (Miller et al., 1994, Marks et al., 1993). New developments have begun looking at treating non-melanoma skin cancer (NMSC) using topical therapies. The essence of this therapy may rely upon the induction of an inflammatory response with infiltration of leucocytes, in particular neutrophils.

To assess whether the compounds of the invention induce neutrophil infiltration, an experiment was designed on C57BL/6J mice. Twenty-four mice were divided into six groups of four mice per group. In three of these groups the mice had a B16 melanoma injected s.c. (2 sites per mouse, $5 \times 10^5$ cells/site), that was left to grow for 8 days to approximate tumor sizes of 5-8 mm in diameter. A single application of one of all three compounds was then applied to the tumor or to normal skin. Each compound was applied on two groups of mice, one with tumor and 1 without tumor. The three compounds were PEP010 (2 μL; 150 mM) in 10 μL of isopropanol gel (isopropyl alcohol 25% (w/w), propyl alcohol 25% (w/w)) (vehicle), PEP009 (2 μL of stock) in 10 μL of vehicle or vehicle alone as a control. One mouse from each group was then sacrificed at either 4 hr, 24 hr, 48 hr or 144 hr post single application of compound and then tissue excised and sections prepared for histology.

Figure 10A:
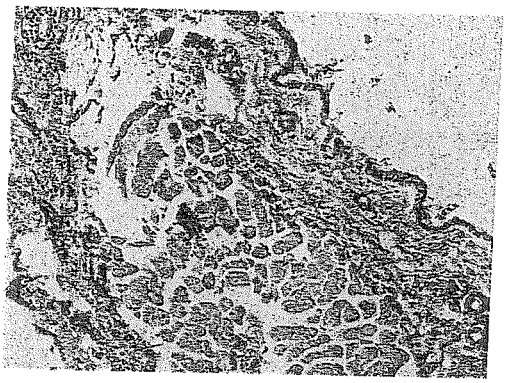
FIG. 10 is a photographic representation showing effect of PEP010 on recruitment of neutrophils in normal skin of nude mouse and skin overlying subcutaneously implanted B16 melanoma. (A) 24 hr treatment, (B) 48 hr treatment.
Figure 10A:
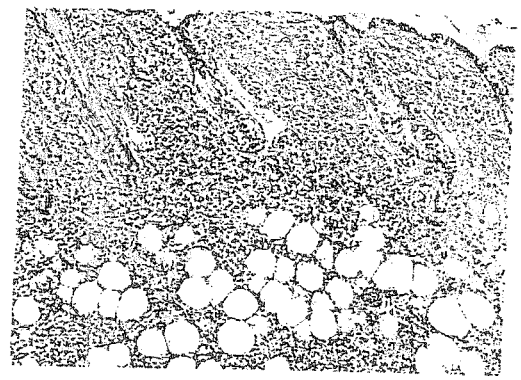
Figure 10A:
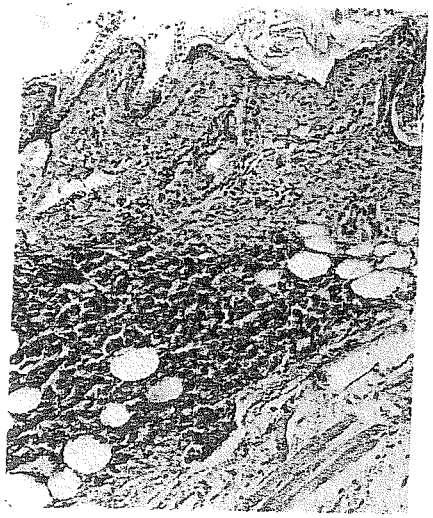
Figure 10A:
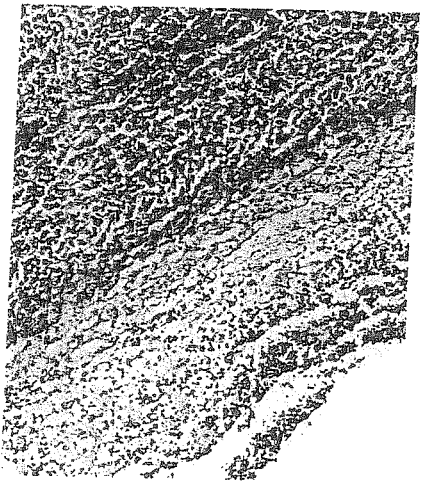
Figure 10B:
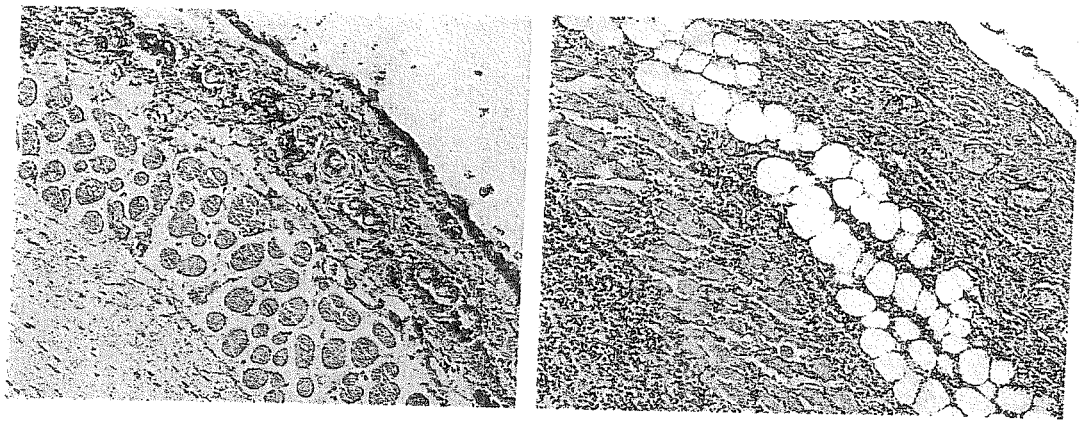
Figure 10B:
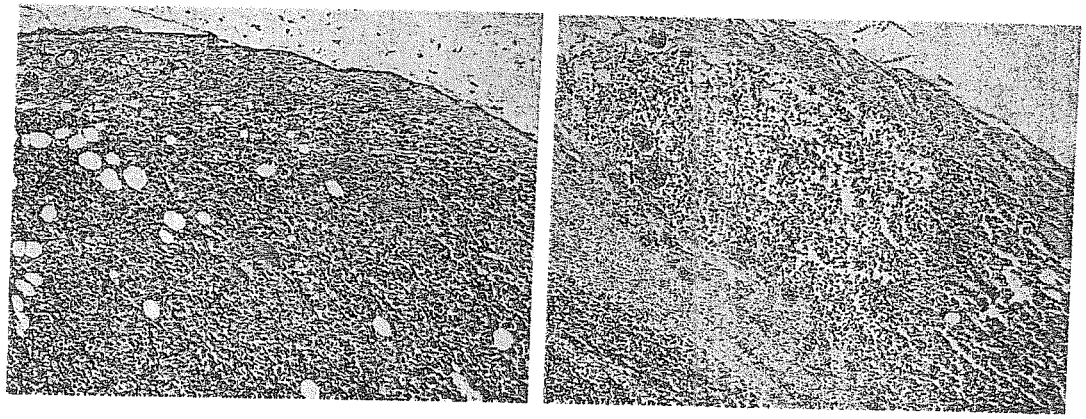

The results at 4 hr show only minimal response with 1+ patchy neutrophils for both PEP010 on B16 tumor and PEP009 on normal skin and 2+ neutrophils present for PEP009 on B16 tumor (Table 2). At 24 hr, there are no neutrophils present in the control groups with vehicle alone but a 4+ neutrophil infiltration with PEP010 and PEP009 application, on both tumor and normal skin (FIGS. 10A and 10B). In addition, 60-85% of the superficial tumor cells were apoptotic or necrotic in the B16 groups. At 48 hr, there was a similar pattern with a 4+ neutrophil presence with PEP010 and PEP009 application while the control groups showed an absence of neutrophils (FIGS. 10A and 10B). Along with the tumor cell necrosis and apoptosis, there is also evidence of some neutrophil breakdown at the 48 hour interval. The 144 hour group showed a lack of neutrophils in the control group and a presence of 2-4+ neutrophils, which were mostly now degenerate in the PEP010 and PEP009 groups. There was extensive necrosis of tumor and skin, and clear signs of granulation tissue and early repair.

This study shows that the PEP010 and PEP009 induce a marked inflammatory infiltrate of neutrophils as compared to vehicle alone and this influx of polymorphonuclear cells may be significant in altering the growth of certain skin cancers.

EXAMPLE 9

Activation of Innate Immune Responses: Induction of a Respiratory Burst in Peripheral Blood Mononuclear Cells Monocytes/macrophages are blood-borne and tissue cells which are usually activated by T lymphocytes and antibodies. Upon activation, they are able to phagocytose pathogens, release superoxide radicals and are an important source of cytokines. Crude *E. peplus* extract was shown to be able to induce the release of superoxide radicals by use of a fluorescence-activated cell sorting (FACS)-based method, in which superoxide radicals are detected by the dye dihydroethidium. In addition, phagocytic activity was activated by *E. peplus*, as shown by increased uptake of nitroblue tetrazolium and adherence to plastic was increased by *E. peplus*; this is believed to indicate activation and differentiation of macrophages.

Figure 11A:
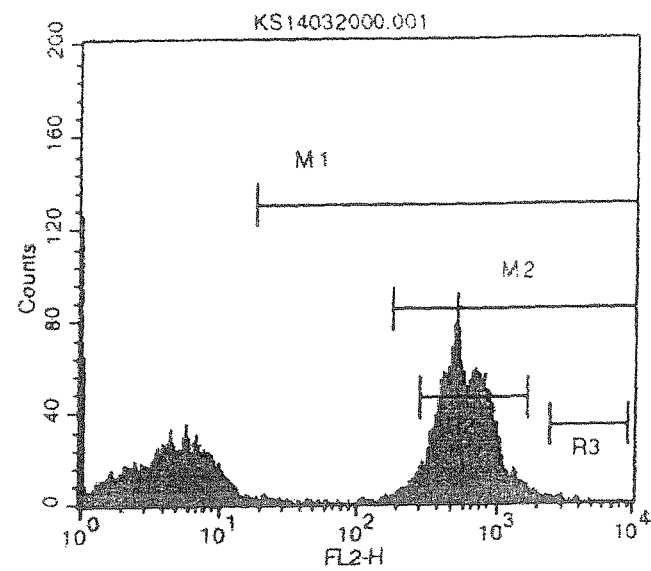
FIG. 11 is a graphical representation comparing the ability of (A) a control and (B) PEP001 to induce the release of superoxide radical, as demonstrated by fluorescence-activated cell sorting.
Figure 11B:
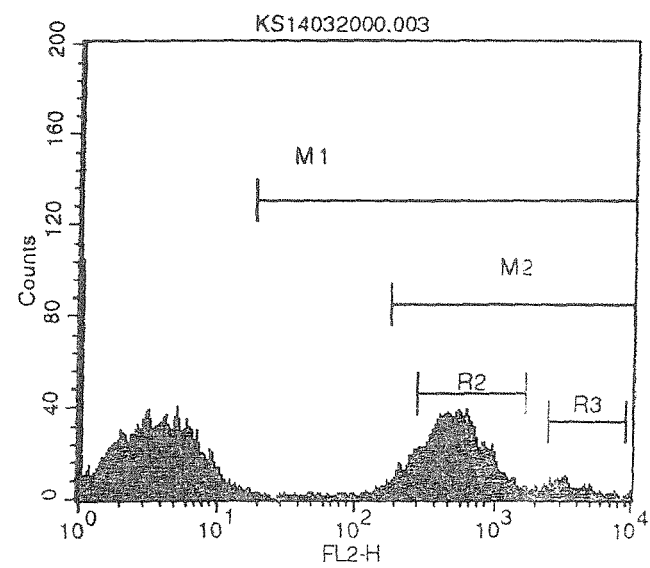

Human peripheral blood mononuclear cells (PBMC) prepared by standard Ficoll separation comprise approximately 5% monocytes. PBMC were incubated with dihydroethidium, a reduced form of the dye which becomes fluorescent when oxidized by a respiratory burst, then treated in 10% FCS-RPMI 1640 at 37° C. for 15 min with crude *E. peplus* extract diluted 1/1000 or 100 ng/mL TPA and analyzed by flow cytometry using conventional methods (Handbook of Flow Cytometry Methods, p. 151). The mean channel numbers for fluorescence were 618 (controls) and 818 (*E. peplus* extract diluted 1/1000). These results, illustrated in FIGS. 11A and 11B, show that the *E. peplus* extract induced intracellular oxidation of the dye, typical of a respiratory burst. Phagocytic activity was determined by a conventional method (Hudson and Hay, Practical Immunology, $3^{rd}$ edition, p. 74). Cells were treated in 10% FCS-RPMI 1640 at 37° C. for 20 min with introblue tetrazolium (NBT) and crude *E. peplus* extract (PEP001) diluted 1/1000 or 100 ng/mL TPA, followed by counting the number of blue-stained cells in a haemocytometer. The average of three fields gave figures of <2% (controls), 10% (TPA) and 8.7% (*E. peplus* sap) cells stained blue. This demonstrates induction of phagocytic activity, part of the normal response to infectious agents, by *E. peplus* sap, as shown by uptake by cells of the blue NBT precipitate.

Experiments were also carried out using 2',7'-dichlorofluorescein diacetate (DCFH-DA) to measure the production of $H_2O_2$. (J P Robinson, Oxidative burst methods, in Handbook of Flow Cytometry Methods, Wiley-Liss Inc, pp 147-149, 1993). $H_2O_2$ oxidizes the non-fluorescent probe (DCFH-DA) to a fluorescent probe that can then be detected by a flow cytometer. Peripheral blood mononuclear cells (PBMC) were extracted from a donor blood sample by lysis of heparinized blood and used in a suspension of $1 \times 10^6$/mL of phosphate buffer, pH 7.3. The cells were then incubated with DCFH-DA (1 μL/mL of 20 mM stock) for 15 minutes to allow it to be taken up and trapped by hydrolysis with cellular esterases. The cells were then stimulated by test compounds for 15 min at 37° C. Controls included in the experiment were unloaded control (cells with no DCFH-DA) and loaded control (cells with DCFH-DA, but no stimulation). These were used to monitor the non-specific oxidation of unstimulated cells. The cells were then analyzed on the flow cytometer (excitation at 488 nm, emission at 525±20 nm), gating each sample for individual cell populations—granulocytes, monocytes and lymphocytes (Table 3).

All compounds except Bryostatin induced a respiratory burst, the effect being strongest in granulocytes and monocytes compared with lymphocytes. Similar results were obtained by measuring the reduction, under the same conditions, of nitroblue tetrazolium, measured as the proportion of purple-stained cells counted under the microscope.

Evidence for the requirement of PKC activation was obtained by addition of bisindolylmaleimide (10 ng/mL or 1 ng/mL) at the same time as PEP005, PEP006, PEP008 and PEP010. This PKC inhibitor blocked the respiratory burst seen with TPA and PEP003.

Phagocytosis with Fluorescent Beads

Phagocytosis by peripheral blood mononuclear cells (PBMCs) was assayed (Steinkamp et al., 1982) using 1 μm Fluoresbrite™ yellow-green fluorescent latex spheres (Polysciences, Inc., Warrington, Pa.). A sample of whole, heparinized blood was treated with drug and 5×10E7 fluorescent latex beads in 10 μL of PBS added per mL of suspension. Cells were incubated and maintained in suspension for 30 min by means of a shaker platform at 37° C. The stimulated and non-stimulated samples were then lysed to isolate PBMCs. The PBMCs were run on the flow cytometer measuring FITC (excitation at 488 nm, emission at 525±20 nm), gated for fluorescence (phagocytosed spheres) and light scatter (cell size).

The data presented in Table 4 indicate that TPA, PEP006, PEP008, PEP003 and PEP005 all stimulate phagocytosis in PBMCs.

EXAMPLE 10

Activation of Innate Antiviral Activity

Many viruses, including alphaviruses, are sensitive to innate antiviral activities, which are often mediated by the activation of interferon α/β responses (Antalis et al., 1998). Such antiviral activities inhibit the ability of cells to support viral replication. For many viral infections, including those caused by Ross River virus, viral replication results in virus-induced cytophathic effect (CPE) or cell death. Treatment of human fibroblast cells with *E. peplus* ingenanes was shown to activate antiviral activity and prevented CPE induced by an alphavirus infection.

Human skin fibroblasts (10e4/well) were seeded in 96 well plate and left overnight to adhere. An extract of *E. peplus* ingenanes was added at 5 μg/mL for 48 hr. An alphavirus (Ross River virus, T48) was then added at a dose of 1, 10 and 100 cell culture ID50 for 6 days (La Linn et al., 1996). The cytopathic effect of the viral infection was assayed using crystal violet staining. Protected cells stain violet, whereas cells which have suffered CPE detach from the plate, leaving the well unstained. Alphavirus-induced CPE was observed in treated cells only at a 100-fold greater dose of virus than was required to induce CPE in untreated cells, indicating that a significant degree of protection was conferred by the *E. peplus* extract.

EXAMPLE 11

Protection Against Intra-Peritoneal Streptococcal Infection: Effect of PEP003 and PEP004 on Systemic Group A Streptococcal Infection in Mice Infection of humans with group A *streptococcus* (*Streptococcus pyogenes*) (GAS) can cause a variety of clinical manifestations including the relatively minor pharyngitis ("trep throat" and impetigo (superficial skin infection) to more severe invasive infections such as toxic shock syndrome and necrotizing fasciitis, both of which, may lead to multisystem organ failure. Lastly, the GAS post-infectious sequelae of rheumatic fever (RF), rheumatic heart disease (RHD) and acute glomerulonephritis (AGN) are a major problem in developing countries and indigenous populations, particularly in Australian Aboriginals. Current treatment for controlling GAS infection is with antibiotic therapy, however, since continual high dose administration of antibiotic is required in cases of repeated episodes of acute RF and the development of RHD, poor compliance is often associated with the persistence of these GAS-associated diseases. The development of a vaccine against GAS infection would prevent GAS-associated diseases including RF and RHD. In the absence of a vaccine, however, the development of new drugs with improved anti-bacterial activity may provide promising therapeutic agents.

The inventors' aim was to test the ability of the PEP003 and PEP004 to systemically protect against GAS infection, in vivo. Mice (n=10) were treated with 50 μL of PEP003 (500 nM), PEP004 (1:100 dilution from stock) or control (PBS/10% acetone), 24 hr prior to and thereafter i.p. challenge with live GAS. Two different strains of mice (Quackenbush and B10.BR) and four different GAS strains (NS-1, PL-1, 88/30 and M1) were used. Mice were monitored for two weeks post-challenge and the percentage survival of mice determined. Percentage survival in Quackenbush mice challenged with PL-1 GAS was 70% (PEP003), 60% (PEP004) and 40% (control) (Table 5). Control mice that had been given the same successive treatment of PEP003 and PEP004 (but not challenged) to rule out any potential adverse side effects of the compounds were then also challenged with PL-1; survival was 40%, 80%, and 20% for PEP003, PEP004 and controls, respectively (Table 6). In the latter experiment, the protective effect of PEP004 approached significance (p=0.06), however, small numbers of mice were used (n=5). In Quackenbush mice challenged with NS-1 GAS, survival was 50% for PEP003 and controls, and 80% for PEP004 (Table 5). In B10.BR mice challenged with M1 GAS, survival was 10% for controls, 30% for PEP003 and 0% for PEP004 (Table 5). In B10.BR mice challenged with 88/30 GAS, survival was 20% for controls, 30% for PEP004 and 0% for PEP003 (Table 5). The data indicate a possible protective effect of PEP004 against systemic GAS challenge in Quackenbush mice. In addition, these data indicate that a weekly treatment regimen of PEP003 and PEP004 prior to GAS challenge may be more effective.

EXAMPLE 12

Anti-*Escherichia coli* Activity of PEP003: Activation of Leucocytes

Blood was collected into a Sodium Heparin tube (Becton Dickinson VACUTAINER) and leucocytes prepared by lysis of red blood cells (Handbook of Flow Cytometry Methods. Robinson J P. Wiley-Liss Inc 1993. Oxidative Burst Methods $H_2O_2$ DCF Assay by Flow cytometry p 147-149). Leucocytes were resuspended and divided equally into two tubes such that each tube contained $7\times10^6$ peripheral blood cells (PBCs). Both tubes were then centrifuged (Beckman, GS-6) at 1000 rpm for 10 minutes. The supernatant was removed and the volume was then adjusted to 1 mL with RPMI 1640 (Gibco BRL, antibiotic free supplemented with 10% v/v fetal bovine serum. 100 μL of PEP003 (to give a final concentration of 23

µg/mL containing 10% acetone was then added to one tube and to the other, 100 pt of PBS/10% Acetone. To each tube, 10 µL *E. coli* (competent cells, XL10-Blue, Stratagene) was also added (to give a ~1/100 dilution of a static culture). Both tubes were vortexed then centrifuged (Beckman, GS-6) at 2500 rpm for 10 minutes. Lids were loosened and the tubes were incubated at 37° C./5% $CO_2$.

Following 16 hr incubation, the tubes were vortexed. To estimate the number of *E. coli*, 50 µL was taken from both tubes as well as the static starter culture (stored at 4° C.), transferred to Eppendorf tubes and centrifuged (Beckman, GS-15R) at 10,000 rpm for 10 minutes. Supernatant (~45 µL) was removed and the pellet resuspended in the remaining ~5 µL. A smear was made on a glass slide using the 5 µL bacterial suspension and stained using Quick Dip (Histo.Labs, Riverstone, Australia), a modified method of the Wright-Giemsa stain, which stains bacteria blue. *E. coli* were counted using a conventional light microscope (×400) with an eyepiece micrometer (100 µm×100 µm). This count was then adjusted to give a total count in the smear (area=$12.5×10^5$ µm$^2$) and expressed as the number of *E. coli* per mL. Another method of measuring growth of *E. coli* was to read the absorbance (595 nm) of the supernatant.

Figure 12:
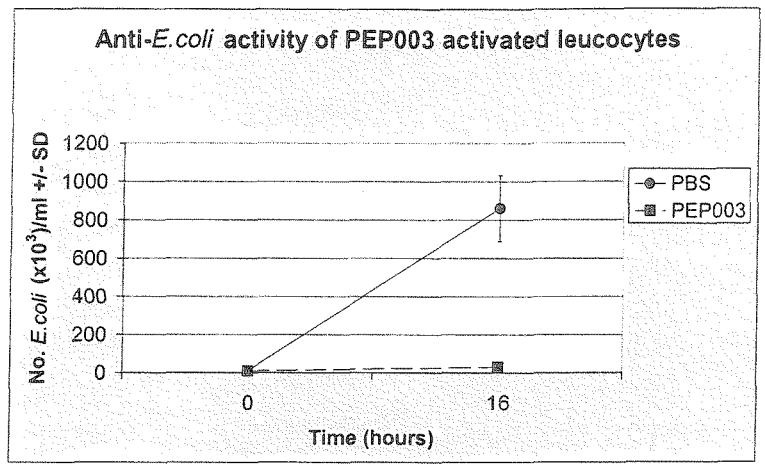
FIG. 12 is a graphical representation showing the effect of pre-treatment of leukocytes with PEP003 on *E. coli* activity (16 hr incubation), relative to PBS control; depicted as numbers of *E. coli* cells/ml media.
Figure 13:
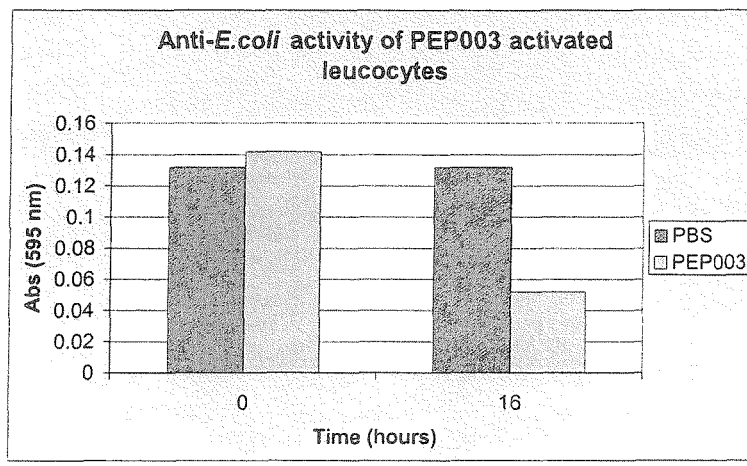
FIG. 13 is a graphical representation showing the effect of pre-treatment of leukocytes with PEP003 on *E. coli* numbers depicted in terms of turbidity.

The results presented in FIGS. 12 and 13 show that treatment of leucocytes with PEP003 results in a significant reduction in bacterial numbers.

EXAMPLE 13

Treatment of Ringworm

Ringworm is a subcutaneous mycosis or dermatophytosis caused by fungi of the species *Trichophyton*, *Microsporum* and *Epidermophyton*, in which the infection is confined to the keratinous structures of the body. A two week old ringworm lesion, determined to be *Trichophyton mentagrophytes* var. *mentagrophytes* by culture, on the volar surface of the forearm of an adult male human was treated with a single topical application of crude *E. peplus* extract and was shown to resolve after seven days. Resolution of such lesions in the absence of treatment does occur, but is considered extremely rare.

EXAMPLE 14

Treatment for Bites of Blood-Sucking Insects

The bites of blood sucking insects such as mosquitoes and sand flies often cause an itchy inflammatory reaction at the site of the bite. Although the extract mechanism of this reaction is poorly understood, mast cells and histamine release are likely components of this reaction (Greaves and Wall, 1996; Horsmanheimo et al., 1996).

In preliminary experiments, the inventors treated human sand fly bites with *E. peplus* extract and found a rapid reduction in the itchy sensation compared to untreated bits at a distant site. Without wishing to be bound by any proposed mechanism, the inventors believe that the *E. peplus* extract may strongly stimulate mast cell exocytosis and histamine release and thereby prevent the slow release over time of these compounds, a feature associated with itchiness.

EXAMPLE 15

Promoter Activation as a Means of Therapy: Effect of PEP003 and PEP004 on Activation of EBV Infected Cell Lines and EBV Positive Burkitt's Lymphoma Cell Lines Initially the effect of PEP003 and PEP004 was tested on the B95-8 cell line (an EBV positive marmoset cell line that is used worldwide as one of the best EBV producers). This cell line was treated with each of these compounds (at different concentrations) for 3 days and 7 days, respectively, and activation of EBV virus production was measured by the appearance of a viral capsid antigen (VCA) on western blots. Also, as a comparison, EBV was activated in this cell line with TPA.

Figure 14:
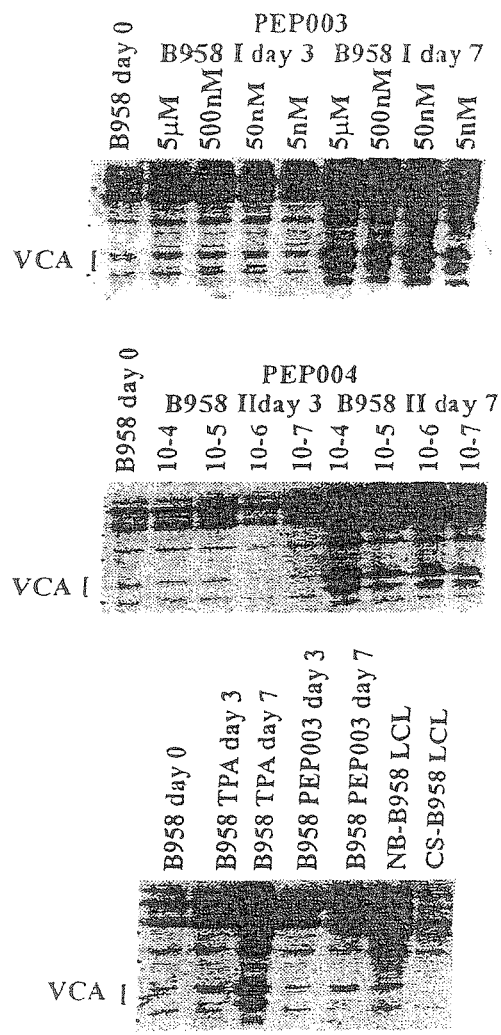
FIG. 14 is a photographic representation showing production of viral capsid antigen (VCA) in B95-8 (EBV+ Marmoset cell line) after treatment with TPA, PEP003 and PEP004 for 3 and 7 days.
Figure 15:
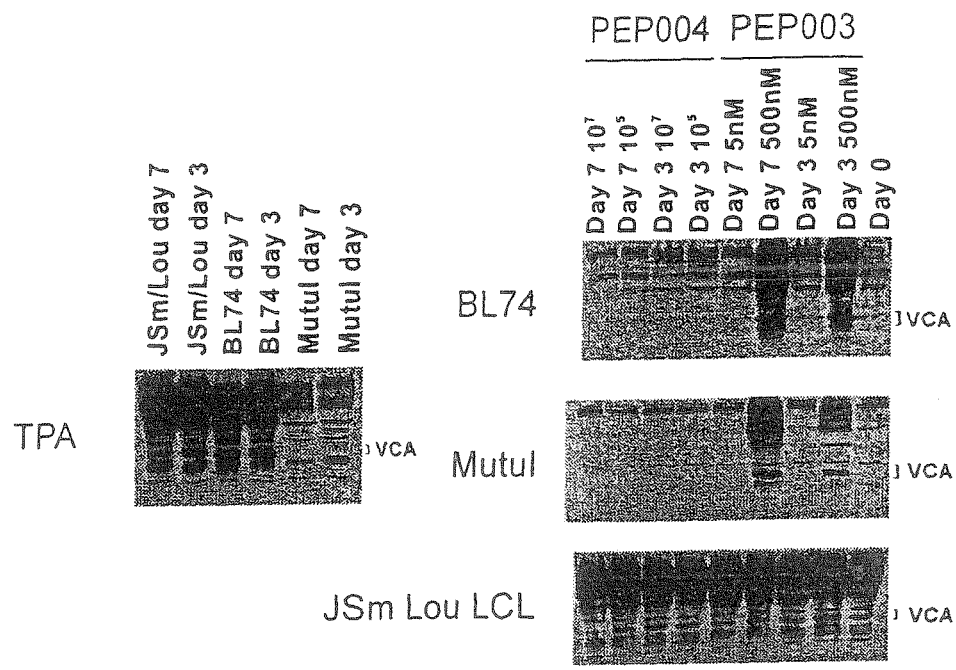
FIG. 15 is a photographic representation showing production of viral capsid antigen (VCA) in BL74 and Mutu I (Burkitts lymphoma cell lines) after treatment with TPA, PEP003 and PEP004 for 3 and 7 days.
Figure 16:
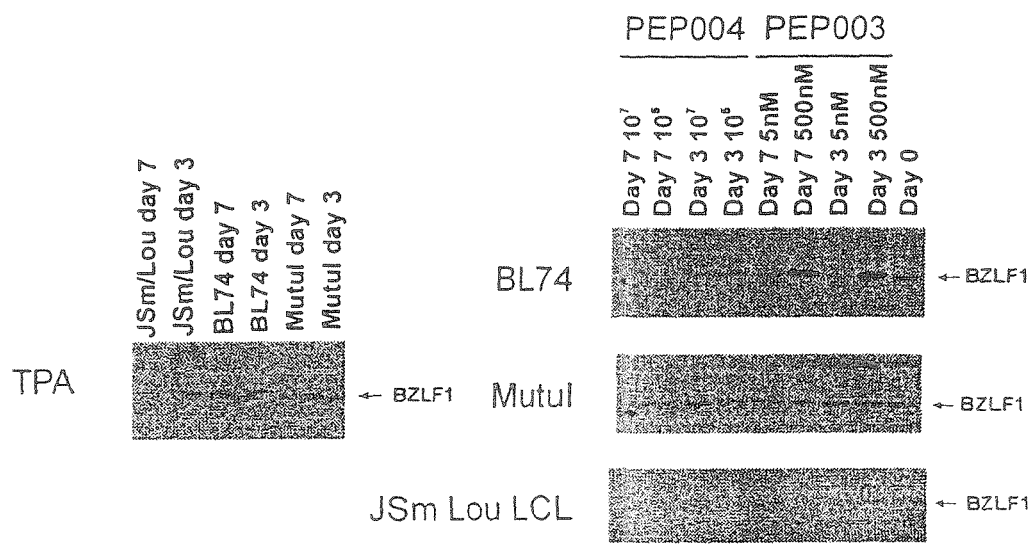
FIG. 16 is a photographic representation showing production of BZLF1 (the initial transactivator of EBV) after treatment with TPA, PEP003 and PEP004 for 3 and 7 days.

To ensure that equal amounts of each sample were analyzed, the gels were stained with Coomassie blue and the loadings were adjusted to make them equal. Analyses of VCA in each of the samples showed that both PEP003 and PEP004 were capable of activating EBV (at all of the concentrations used) to similar levels as using 65 nM TPA (FIG. 14). Next the PEP003 and PEP004 were assayed on two Burkitt's lymphoma cell lines and an LCL. This time only concentrations of $10^{-5}$ and $10^{-7}$ were used. Neither PEP003 and PEP004 had much effect on the LCL (this LCL produces some VCA without and chemical induction and this was not increased by these compounds). PEP004 had no effect on VCA production in any of the cell lines used. However, PEP003 did induce high levels of VCA in both Burkitt's lymphoma cell lines (Mutul and BL74), but only at $10^5$ concentration (FIG. 15). Similar results were obtained when the cell lines were assayed for induction of BZLF1, the initial transactivator of EBV replication (FIG. 16). The results show that PEP003 was capable of activating EBV in Burkitt's lymphoma cell lines, but appeared to have little effect on LCLs.

In conclusion, (1) both TPA and PEP003 can modulate gene expression in EBV transformed tumor cells at the doses used; (2) while PEP003 induced VCA in Mutul cells TPA did not, indicating different modes of action; (3) surprisingly, there was no apparent effect of PEP003 on lymphoblastoid cells, indicating potential for activating latent herpesvirus in tumors without affecting the normal infection.

EXAMPLE 16

Investigation into the Effect of PEP003 on the Ability of Melanoma Cells to Stimulate NK Activity Melanomas and other cancers can be killed by both specific (T cell-mediated) and non-specific (natural killer cell and other mechanisms) arms of the immune response. These killer cells can be generated in vitro by stimulating peripheral blood T cells from selected melanoma patients with melanoma cells derived from the same patient ("autologous"). Natural killer cells can be recognized by their lysis of the natural killer-sensitive cell line K562. It has been theorized that some anti-tumor agents alter the susceptibility of melanomas to immune responses.

Peripheral blood lymphocytes from patient A02, who has a strong specific T cell response to her own melanoma cells (A02-M), were thawed and stimulated by irradiated A02-M pre-treated overnight at 37° C. with (a) PEP003 (2.25 µg/mL; 50 µM); (b) TPA (100 ng/mL); or (c) control solvent/buffer, and washed ×2 before addition to responding lymphocytes (washing ×2 achieves a residual agent dilution of ×100,000). After 10 days of culture, the stimulated cells were harvested and used as effectors against an NK-sensitive cell line (K562) to test for the level of NK activity generated in culture. All determinations were performed in triplicate, at E:T ratios of 45, 15, 5 and 1.7:1. A standard 5 hour $^{51}$Cr release assay was performed. Stimulations were performed in 10% fetal bovine serum/RPMI-1640.

Figure 17:
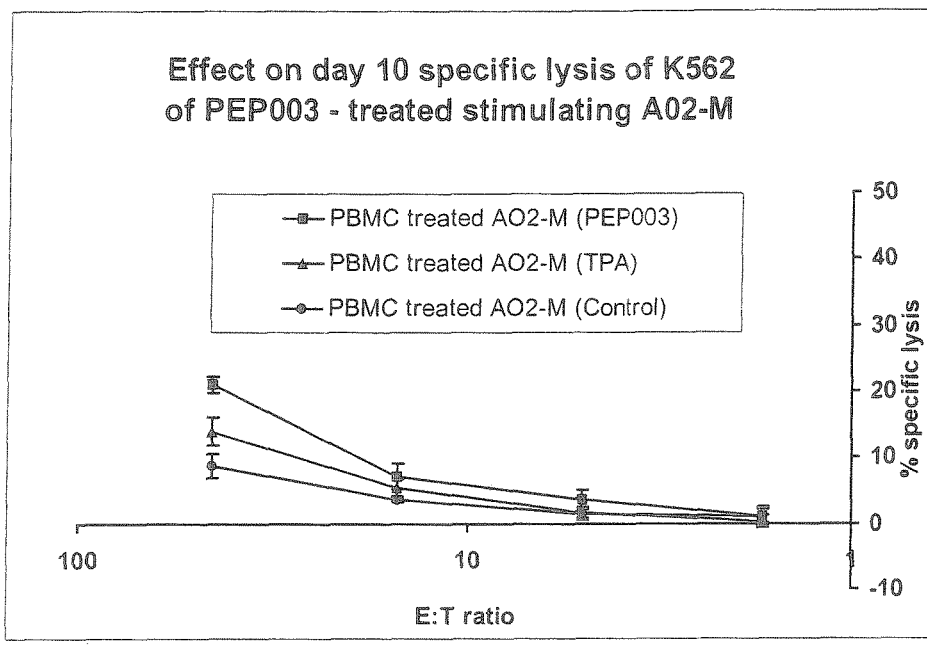
FIG. 17 is a graphical representation showing activation of natural killer cell activity, assayed as % specific lysis of K562 cells (a natural killer—sensitive cell line) after pre-treatment of AO2-M melanoma cells with PEP003 and TPA.

The results presented in Table 7 and FIG. 17 indicate that pre-treatment of melanoma cells with PEP003 significantly increases the lysis of K562 compared to both TPA and the control treatment at the E:T ratio of 45:1 (P<0.01 in both cases), suggesting that PEP003 increases NK activity in A02 cultures.

EXAMPLE 17

Methods for Obtaining a Low-Chlorophyll, Hydrophobic Fraction from E. Peplus and Other Plant Species Standard methods for the isolation of hydrophobic compounds from plants involve alcoholic extraction of the whole plant. This produces an extract containing chlorophyll and other hydrophobic substances from the leaves that interfere with subsequent purification of compounds by solvent extractions and chromatography. This is a particular problem in isolating highly bioactive diterpenes from members of the Euphorbiaceae family, due to co-migration with chlorophyll on silica gel chromatography. Two methods, both of which can be scaled up for economical, commercial production, have been developed to overcome this problem, as described in the present Example and in Example 18.

Fresh E. peplus plants (17 kg) were chopped and soaked in 150 liters of water at 4° C. for 20 hr. The water was pumped through 50 and 100 mesh sieves, filtered through 5 and 2 micron filters and then recirculated through a 100 mm diameter column of Amberlite XAD-16 (1.5 kg, conditioned successively with ethyl acetate, methanol and water) at 4° C. (approximately 1.2 L/min) for 72 hr. Adsorption of bioactivity to the resin was found to be virtually complete within 20 hr.

The resin was then washed successively with water and 50% methanol, then eluted with 1 L of methanol, followed by 2×1 L acetone. The eluates were evaporated and combined to give approximately 7 g of a thick oil. This was shown by HPTLC to be substantially free of chlorophyll and to contain the desired ingenane esters which were then purified as described below.

The ability to extract diterpene esters from chopped plants in water was surprising given their relative hydrophobicity and water insolubility. A variety of manual (cutting with scissors) and mechanical (rotary cutters, motor-driven mulcher) plant maceration methods were successful, as was extraction at room temperature. Adsorption to the XAD-16 could be achieved by stirring the resin with the filtered or unfiltered water extract and then pouring off the latter. Filtration could also be carried out with minimal loss of bioactivity using diatomaceous earth, or membrane filters (220-650 microns). XAD-7 and XAD-4 were as effective as XAD-16.

The hydrophobic adsorbent polyamide (ICN Biomedical Research Products) was also used to trap the diterpenes from water; it had the advantage of allowing the diterpene esters to be selectively eluted with 50-80% methanol, thus separating them from inactive, hydrophobic compounds, which remained on the column.

EXAMPLE 18

Method for Separation of Ingenane Esters from Other Diterpenes

The following method is based upon the surprising discovery that the stems of E. peplus contain approximately 90% of the bioactive diterpenes and significantly less chlorophyll compared with the leaves.

The plants are dried in air, shaken to remove the leaves and the stems compressed and covered with an equal weight of methanol for 24 hr. The solvent is then poured off, evaporated to dryness under reduced pressure and the residue dissolved in methanol for chromatography on Sephadex HL20 as described below. This method is also suitable for isolation of low-chlorophyll fractions from other plant species.

A solution of crude methanol extract from E. peplus in 4 mL 90% ethanol was loaded onto a 25 mm×1000 mm column and eluted with 90% methanol. Fractions (4 mL) were analysed by HPTLC (silica gel, developed with 4:1 toluene:acetone and heated with phosphoric acid at 110 degrees for 15 min). Typically, fractions 54-63 contained jatrophane and pepluane esters and fractions 64-77 the ingenane esters, thus achieving satisfactory separation. Bioactivity, as judged by induction of bipolar morphology in the human melanoma cell line MM96L, was retained, as for example disclosed in PCT/AU98/00656.

This separation was surprising because the polarity of the ingenane esters as judged by HPTLC on silica completely overlapped the range shown by the jatrophane and pepluane esters.

EXAMPLE 19

Process for the Purification of Diterpene Esters from E. Peplus

Crude extracts obtained by the methods according to Examples 17 or 18 above, or by ether extraction of latex, were fractionated by Sephadex HL-20 chromatography (as above). Appropriate fractions from the latter were combined, the methanol evaporated under reduced pressure and the remaining water removed by freeze-drying or by ether extraction. This sample (200 µL of 100 mg/mL in methanol per injection) was fractionated by HPLC on a Phenomenex Luna 250×10 mm C18 column with a Phenomenex guard column in 70-100% methanol at 2 mL/min, with detection at 230 nm. Jatrophane and pepluane esters appeared at 25-42 min, PEP005 at 42-44 min, PEP008 at 46-50 min, and PEP006 at 50-54 min. Similar types of separation have been obtained by HPLC on C3 and C8 columns.

Fractions pooled from repeated runs were evaporated to dryness (rotary evaporater or freeze dryer), and stored in acetone at −20° C. under argon or nitrogen.

EXAMPLE 20

Activation of Leukocytes by Diterpene Esters, for Selective Killing of Human Tumor Cells in Culture Leukocytes obtained by lysis of human peripheral blood were added to 5000 MM96L human melanoma cells or 7000 neonatal foreskin fibroblasts per microtitre well at effector: target ratios of 1000, 100 and 10:1. Ing9 (60 ng/mL) was added and after 48 hr incubation the cultures were washed and labelled with [3H]-thymidine for 2 hr. At 100:1 ratio of effector:target cells, the melanoma cells showed 9% survival with PEP008 whereas the normal fibroblasts had 100% survival. Untreated leukocytes had no effect on cell survival.

These results indicate that the diterpene esters of the invention activate human peripheral blood leukocytes to produce, in a PKC-dependent manner, phagocytosis and a respiratory burst which are potentially lethal to micro-organisms and other cells.

This example shows that drug-activated, PKC-dependent processes can direct tumor-specific killing by cells of the innate immune system.

EXAMPLE 21

Pretreatment of Human Tumor Cells in Culture with Diterpene Esters Potentiates Selective Killing by Untreated Leukocytes The question of whether drug treatment of the target tumor cells causes them to become susceptible to effector cells of the immune system was addressed as follows.

Leukocytes obtained by lysis of human peripheral blood were added to 5000 MM96L human melanoma cells or 7000 neonatal foreskin fibroblasts per microtitre well at effector:target ratios of 1000, 100 and 10:1. The target cells had been treated with 60 ng/mL PEP008 for 20 hr beforehand, and washed and the medium replaced before the leukocytes were added. After 48 hr incubation with the leukocytes the cultures were washed and labelled with [3H]-thymidine for 2 hr. At 100:1 ratio of effector:target cells, the melanoma cells showed 12% survival with PEP008 whereas the normal fibroblasts had 100% survival. Untreated leukocytes had no effect on cell survival.

This result showed that the drugs also act by making tumor cells specifically sensitive to lysis by the immune system.

EXAMPLE 22

Topical Composition A for the Treatment of Conditions Affecting Skin (e.g. Infections, Skin Cancers)

Tinctures: Compounds of the invention were diluted into acetone, ethanol or isopropanol to the same final bioactivity as the *E. peplus* latex as measured by bipolar activity in MM96L human melanoma cells (10 million by units per mL). Samples (2-5 µL) were applied daily for 3 days to the surface of mouse melanoma B16 tumor 3-5 days after implanting s.c. 1 million cells on the flanks of nude mice. Efficacy, defined as 67% or more sites cured, was obtained for *E. peplus* sap, PEP005, PEP008 and a mixture of PEP005, PEP006 and PEP008.

EXAMPLE 23

Topical Composition B for the Treatment of Conditions Affecting Skin (e.g. Infections, Skin Cancers)

Creams and gels: A variety of hydrophobic cream bases was found to be ineffective when used to deliver compounds to the skin as described above for the tinctures. Efficacy was obtained with the use of an isopropanol gel, formulated as described for the tinctures.

The results show that *E. peplus* sap and its terpenoid components activate PKC, with consequent potential to induce a wide range of cellular responses without the high tumor promoting activity of TPA. The carboxypeptidase activity may have application in enhancement of tissue penetration and in antigen processing for optimal immune responses.

Overall, the results indicate that *E. peplus* extract induces a set of cellular responses with affects PKC, cell cycle genes and inflammatory mediators, some but by no means all of which are similar to the action of TPA. In particular, the results indicate that *E. peplus* sap and its terpenoid components are useful in the treatment of a variety of infections and as adjuvants for stimulating immune responses.

EXAMPLE 24

Effect of Saps Derived from Other Members of the Euphorbiaceae Family on MM96L Cells Sap was collected from *Synadenium grantii, Synadenium compactum, Mondenium lugardae, Mondenium guentheri, Endadenium gossweileni*, and *E. peplus* and serially diluted ten-fold up to $10^{-7}$ into sterile 1.5 mL Eppendorf™ tubes using growth medium. Ten-microliter aliquots of each dilution, in the presence or absence of the PKC inhibitor bisindolylmaleimide (1 µg/mL or 10 µg/mL), were added to 5000 MM96L cells per well of a microtitre plate. After 3 days, cells were examined for cytotoxicity or differentiation to a bipolar dendritic phenotype.

The results presented in Table 8 show that the saps of *S. grantii, S. compactum, M lugardae, M. guentheri*, and *E. gossweileni*, like that of *E. peplus*, induce the differentiation of MM96L cells to a bipolar phenotype and that this differentiation is inhibited by the bisindolylmaleimide. This inhibition strongly suggests that the active components of the saps induce cell differentiation by inhibition of PKC activity. The results also show that at higher concentrations ($10^{-4}$ and above), the saps are effective in killing MM96L cells.

EXAMPLE 25

Effect of Saps Derived from Other Members of the Euphorbiaceae Family on JAM Cells The saps of Example 24 were also examined for their cytotoxic effect on the ovarian carcinoma cell line JAM. Ten-microliter aliquots of each dilution of sap, prepared according to Example 24 in the presence or absence of the PKC inhibitor bisindolylmaleimide (10 µg/mL), or in the presence or absence of the PKC phorbol ester binding site ligand phorbol dibutyrate, were added to 5000 JAM cells per well of a microtitre plate. After three days, the cells were fixed with ethanol and the number of cells compared with untreated controls stained with sulfurhodamine B.

Figure 18A:
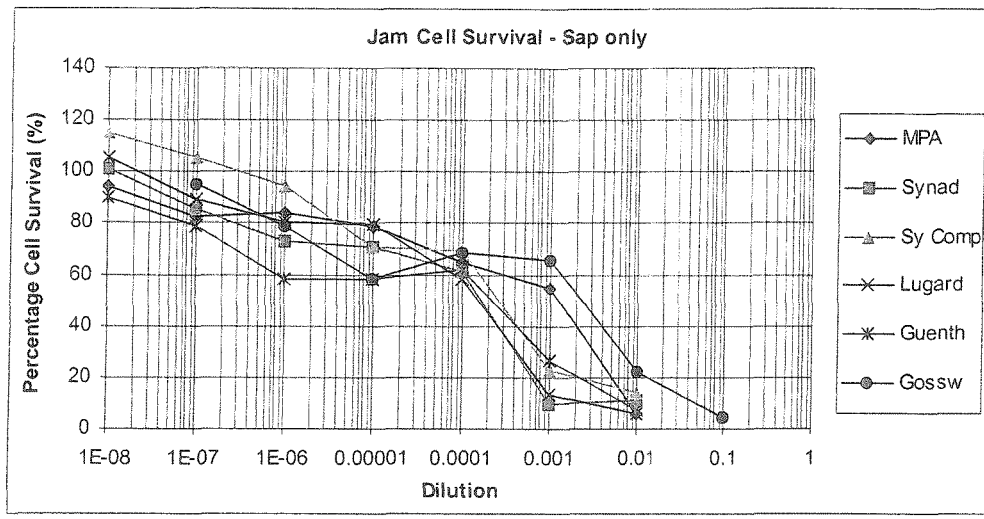
Figure 18B:
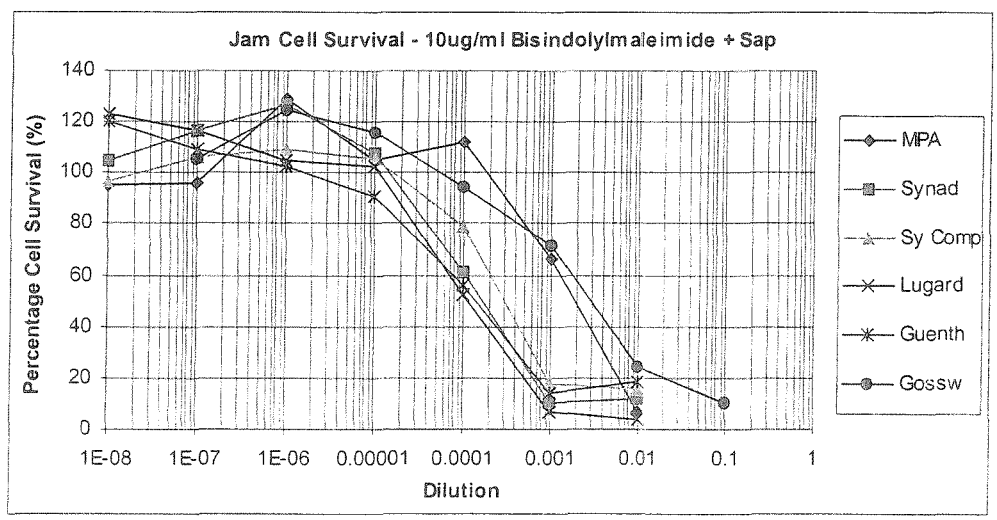
FIG. 18B shows the cytotoxcity of the saps on the Jam cells in the presence of the PKC inhibitor, bisindolymaleimide, and FIG. 18C reveals the cytotoxic effects of saps derived from two Euphorbiaceae on the Jam cells in the presence of phorbol dibutyrate.

The results presented in FIGS. 18A and 18B indicate that, like the sap of *E. peplus*, the saps of *S. grantii, S. compactum, M. lugardae, M. guentheri*, and *E. gossweileni*, at concentrations of $10^{-4}$ and above, are effective in killing JAM cells. These results also show that cytotoxicity is inhibited by bisindolylmaleimide, suggesting that this effect is mediated by modulation of PKC.

Figure 18C:
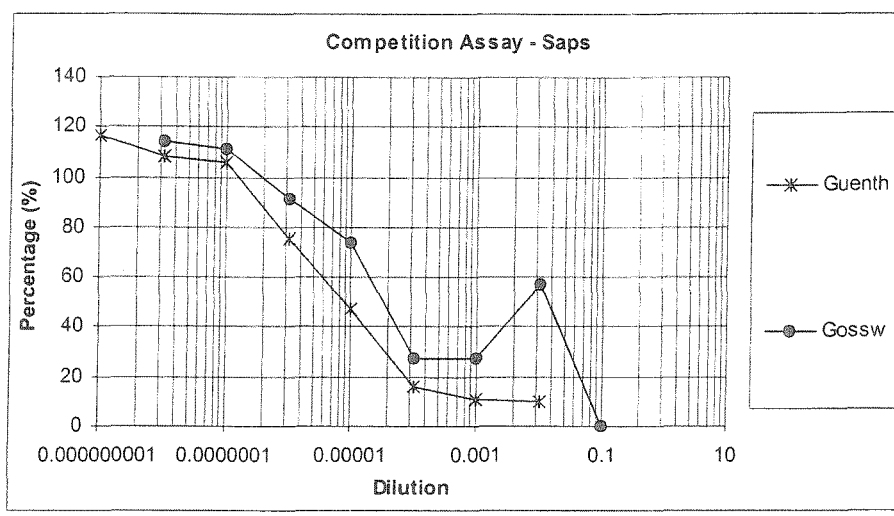

Inspection of FIG. 18C reveals that the cytotoxic effects of saps derived from *M. guentheri* and *E. gossweileni* were blocked in the presence of phorbol dibutyrate, suggesting that the active components of these saps mediate their cytotoxicity by binding to the phorbol ester binding site of PKC.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Antalis et al., *J. Exp. Med.* 187: 1799-1811, 1998.
Christenson et al., *Endothelium* 7: 75-82, 1999.
Elliott et al., *Vaccine* 17: 2009-2019, 1999.
Evans & Osman, *Nature* 250: 348, 1974.

Fatope et al., *J. Med. Chem.* 39: 1005-1008, 1996.
Gonzalez et al., *Melanoma Res.* 9: 599-606, 1999.
Greaves and Wall, *Lancet* 348(9032): 938-940, 1996.
Gundidza and Kufa, *Centr. Afr. J. Med.* 38: 444-447, 1992.
Hecker "Cocarcinogens from Euphorbiaceae and Thymeleaceae" in *"Symposium on Pharmacognosy and Phytochemistry"*, 147-165, (Wagner et al., eds., Springer Verlag, 1970).
Horsmanheimo et al., *J. Allergy Clin. Immunol.* 98: 408-411, 1996.
Imai et al., *Anticancer Res.* 14: 933-936, 1994.
La Linn et al., *J. Gen. Virol.* 77-407-412, 1996.
Marks et al., *Int. J. Cancer* 53(4): 585-590, 1993.
Matsushita et al., *Int. J. Hematol.* 72(1): 20-7, 2000.
Miller et al., *J. Am. Acad. Dermatol.* 30(5): 774-778, 1974.
Mollinedo, *Immunol. Today* 20(12): 535-7, 1999.
Murali-Krishna et al., *Immunity* 8: 177-187, 1998
Oksuz et al., *Phytochemistry* 42: 473-478, 1996.
Starvic and Stolz, *Food Cosmet. Toxicol.* 14: 141, 1976.
Steinkamp et al., *Science* 215: 64-66, 1982.
Tobiume et al., *J. Gen. Virol.* 79: 1363-1371, 1998.

The invention claimed is:

1. A method for the topical treatment of skin cancer in a subject in need thereof, said method comprising topical administration of a therapeutically effective amount of a gel to the skin of the subject, wherein the gel comprises purified ingenol-3-angelate or a pharmaceutically acceptable salt thereof and isopropanol.

2. The method according to claim 1, wherein said subject is a human.

3. The method of claim 1, wherein the therapeutically effective amount of the pharmaceutical composition of purified ingenol-3-angelate or a pharmaceutically acceptable salt thereof is administered daily to the skin of the subject.

4. The method of claim 1, wherein the cancer is basal cell carcinoma.

5. The method of claim 1, wherein the cancer is melanoma.

* * * * *